United States Patent
Wang et al.

(10) Patent No.: US 12,180,539 B2
(45) Date of Patent: *Dec. 31, 2024

(54) APPLICATION OF CAS PROTEIN, METHOD FOR DETECTING TARGET NUCLEIC ACID MOLECULE AND KIT

(71) Applicant: Shanghai Tolo Biotechnology Company Limited, Shanghai (CN)

(72) Inventors: Jin Wang, Shanghai (CN); Qiuxiang Cheng, Shanghai (CN); Shiyuan Li, Shanghai (CN); Xiaoyan Li, Shangai (CN); Linxian Li, Shanghai (CN)

(73) Assignee: Shanghai Tolo Biotechnology Company Limited, Shanghai (CN)

( * ) Notice: Subject to any disclaimer, the term of this patent is extended or adjusted under 35 U.S.C. 154(b) by 1308 days.

This patent is subject to a terminal disclaimer.

(21) Appl. No.: 16/631,157

(22) PCT Filed: Apr. 12, 2018

(86) PCT No.: PCT/CN2018/082769
§ 371 (c)(1),
(2) Date: Jan. 14, 2020

(87) PCT Pub. No.: WO2019/011022
PCT Pub. Date: Jan. 17, 2019

(65) Prior Publication Data
US 2023/0002811 A1  Jan. 5, 2023

(30) Foreign Application Priority Data

Jul. 14, 2017  (CN) .......................... 201710573752.0

(51) Int. Cl.
| | |
|---|---|
| *C12Q 1/6823* | (2018.01) |
| *C12N 9/22* | (2006.01) |
| *C12N 15/113* | (2010.01) |
| *C12Q 1/6886* | (2018.01) |

(52) U.S. Cl.
CPC ............ *C12Q 1/6823* (2013.01); *C12N 9/22* (2013.01); *C12N 15/113* (2013.01); *C12Q 1/6886* (2013.01); *C12N 2310/20* (2017.05)

(58) Field of Classification Search
CPC .... C12Q 1/6823; C12Q 1/6886; C12Q 1/683; C12Q 1/6816; C12Q 2563/107; C12N 9/22; C12N 15/113; C12N 2310/20; Y02A 50/30
See application file for complete search history.

(56) References Cited

U.S. PATENT DOCUMENTS

| | | | |
|---|---|---|---|
| 9,790,490 B2 * | 10/2017 | Zhang .................... | C12N 15/10 |
| 11,584,955 B2 | 2/2023 | Wang et al. | |
| 2012/0058481 A1 | 3/2012 | Ge et al. | |
| 2014/0298547 A1 * | 10/2014 | Sastry-Dent ......... | C12Q 1/6895 800/312 |
| 2016/0177278 A1 | 6/2016 | Wolfe et al. | |
| 2016/0215300 A1 | 7/2016 | May et al. | |
| 2016/0362667 A1 | 12/2016 | Donohoue et al. | |
| 2017/0130238 A1 | 5/2017 | Edwards et al. | |
| 2017/0159073 A1 | 6/2017 | Donohoue et al. | |
| 2017/0175104 A1 | 6/2017 | Doudna et al. | |
| 2017/0198308 A1 | 7/2017 | Qi et al. | |
| 2020/0216551 A1 | 7/2020 | Li et al. | |
| 2020/0254443 A1 | 8/2020 | Zhang et al. | |
| 2021/0381038 A1 | 12/2021 | Li et al. | |
| 2023/0131421 A1 | 4/2023 | Wang et al. | |

FOREIGN PATENT DOCUMENTS

| | | |
|---|---|---|
| CA | 2947904 A1 | 5/2017 |
| CN | 105441440 A | 3/2016 |
| CN | 107488710 A | 12/2017 |
| JP | 2018518183 A | 7/2018 |
| WO | WO-2016/123243 A1 | 8/2016 |
| WO | WO-2017/053762 A1 | 3/2017 |
| WO | WO-2017/070605 A1 | 4/2017 |
| WO | WO-2019/104058 A1 | 5/2019 |

OTHER PUBLICATIONS

Livak, Kenneth J., et al. "Oligonucleotides with fluorescent dyes at opposite ends provide a quenched probe system useful for detecting PCR product and nucleic acid hybridization." Genome Research 4.6 (1995): 357-362 (Year: 1995).*
Abudayyeh, Omar O., et al. "C2c2 is a single-component programmable RNA-guided RNA-targeting CRISPR effector." Science 353. 6299 (Aug. 5, 2016): aaf5573 (Year: 2016).*
Zuo, Xiaolei, Chunhai Fan, and Hong-Yuan Chen. "Biosensing: CRISPR-powered diagnostics." Nature Biomedical Engineering 1.6 (Jun. 13, 2017): 0091 (Year: 2017).*
Gootenberg, J et al., Nucleic acid detection with CRISPR-Cas13a/ C2c2, Science, 356(6336):438-442 (2017).
International Search Report and Written Opinion for PCT/CN2018/ 082769, received by the ISA/CN, 17 pages (Jul. 12, 2018).
Swarts, D. et al., Structural basis for guide RNA processing and seed-dependent DNA targeting and cleavage by CRISPR-Cas12a, Mol Cell., 66(2):223-233 (2017).
Yan, M. et al., CRISPR_Cas12a-Assisted Recombineering in Bacteria, Applied and Environmental Microbiology, 83(17):e00947-17, 13 pages (2017).
Fakruddin, M. et al., Nucleic acid amplification: Alternative methods of polymerase chain reaction, J. Pharm. Bioallied Sci., 5(4):245-252 (2013).
Extended European Search Report mailed on Mar. 22, 2021, for European Application No. 18832456.0, 11 pages.

(Continued)

*Primary Examiner* — Nancy J Leith
*Assistant Examiner* — Kyle T Rega
(74) *Attorney, Agent, or Firm* — Choate, Hall & Stewart LLP; Brenda Herschbach Jarrell; Michael L. Vetter

(57) ABSTRACT

The present invention provides a use of a Cas protein, and a method and a kit for detecting target nucleic acid molecules. The method for detecting target nucleic acid molecules comprises adding a guide RNA, a Cas12a, and a nucleic acid probe into a reaction system containing target nucleic acid molecules to be detected, and detecting it after the reaction is completed.

25 Claims, 30 Drawing Sheets

Specification includes a Sequence Listing.

(56) References Cited

OTHER PUBLICATIONS

Li, S. et al., CRISPR-Cas12a-assisted nucleic acid detection, Cell Discovery, 4(20): 4 pages (2018).
East-Seletsky, A. et al., Two distinct RNase activities of CRISPR-C2c2 enable guide-RNA processing and RNA detection, Nature, 538(7624):270-273 (2016).
Gao, P. et al., Type V CRISPR-Cas Cpf1 endonuclease employs a unique mechanism for crRNA-mediated target DNA recognition, Cell Research, 26(8):901-13 (2016).
Shiyuan, L. et al., Research progress in synthetic biology technology—DNA synthesis, assembly, and genome editing, Journal of Biotechnology, 33(3):343-360 (2017).

* cited by examiner

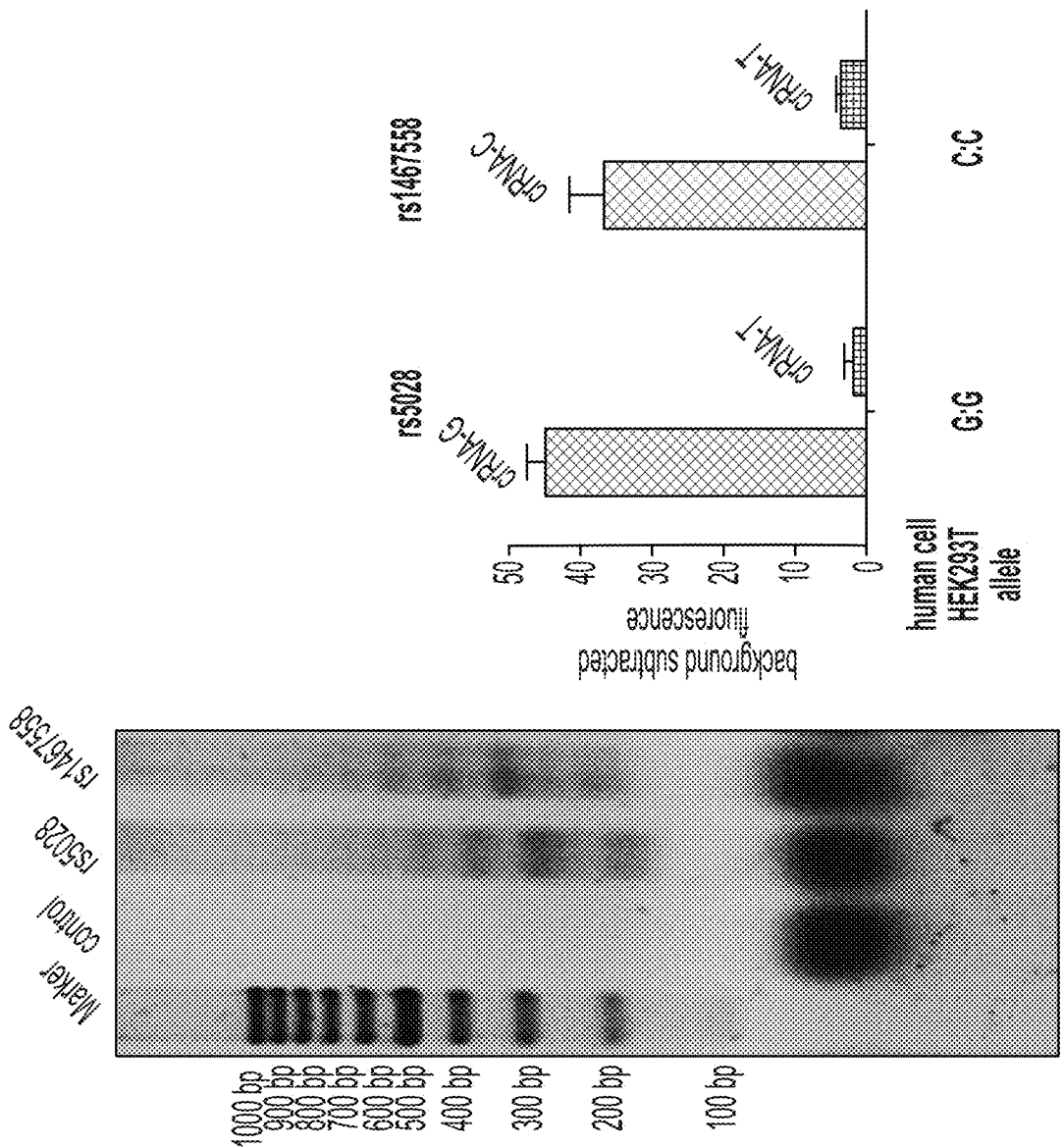

SEQUENCE LISTING

<160> NUMBER OF SEQ ID NOS: 187

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aatgtttcct gatggtccat gtctgttact cgcctgtcaa gtggcgtgac           50

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtcacgccac ttgacaggcg agtaacagac atggaccatc aggaaacatt           50

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtcacgccac ttgacaggcg agtaacagac atggaccatc aggaaacatt           50

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtcacgccac ttgacaggcg agtaacagac atggaccatc aggaaacatt           50

<210> SEQ ID NO 5
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tttctgtttg ttatcgcaac tttctactga attcaagctt tactctagaa agaggagaaa   60
ggatcc                                                              66

<210> SEQ ID NO 6
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 ggatccttc tcctctttct agagtaaagc ttgaattcag tagaaagttg cgataacaaa     60
cagaaa     66

<210> SEQ ID NO 7
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tttctgtttg ttatcgcaac tttctactga attcaagctt tactctagaa agaggagaaa     60
ggatcc     66

<210> SEQ ID NO 8
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8 ggatccttc tcctctttct agagtaaagc ttgaattcag tagaaagttg cgataacaaa     60
cagaaa     66

<210> SEQ ID NO 9
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tttctgtttg ttatcgcaac tttctactga attcaagctt tactctagaa agaggagaaa     60
ggatcc     66

<210> SEQ ID NO 10
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10 ggatccttc tcctctttct agagtaaagc ttgaattcag tagaaagttg cgataacaaa     60
cagaaa     66

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtcacgccac ttgacaggcg agtaacagac atggaccatc aggtttcatt     50

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 12
gtcacgccac ttgacaggcg agtaacagac atggaccatc aggccccatt        50

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 13
gtcacgccac ttgacaggcg agtaacagac atggaccatc aggggggcatt       50

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 14
aatgaaacct gatggtccat gtctgttact cgcctgtcaa gtggcgtgac        50

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 15
aatggggcct gatggtccat gtctgttact cgcctgtcaa gtggcgtgac        50

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 16 aatgcccect gatggtccat gtctgttact cgcctgtcaa gtggcgtgac        50

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 17
acaaacagaa a                                                  11

```
<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cgataacaaa cagaaa                                                      16

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aagttgcgat aacaaacaga aa                                               22

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
agtagaaagt tgcgataaca aacagaaa                                         28

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gaattcagta gaaagttgcg ataacaaaca gaaa                                  34

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gaattcagta gaaagttgcg ataa                                             24

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
agtagaaagt tgcgataa                                                    18
```

```
<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aagttgcgat aa                                                           12

<210> SEQ ID NO 25
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25 cgataa                                                                   6

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(25)
<223> OTHER INFORMATION: a, c, g, or t

<400> SEQUENCE: 26
nnnnnnnnnn nnnnnnnnnn nnnnn                                             25

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(25)
<223> OTHER INFORMATION: a, c, g, or t

<400> SEQUENCE: 27
nnnnnnnnnn nnnnnnnnnn nnnnn                                             25

<210> SEQ ID NO 28
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggatcctttc tcctctttct agagtaaagc ttgaattcag tagaaagttg cgataacaaa       60
cagaaa                                                                  66

<210> SEQ ID NO 29
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 29
cacaattcca cacaacatac gagccgga                                          28

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tgtagccgta gttaggccac cacttca                                           27

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
agttttgtta tcgcaacttt ctactgaatt c                                      31

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
agttttgata tcgcaacttt ctactgaatt c                                      31

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
agttttgtaa tcgcaacttt ctactgaatt c                                      31

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
agttttgttt tcgcaacttt ctactgaatt c                                      31

<210> SEQ ID NO 35
<211> LENGTH: 31
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 35
agttttgtta acgcaactttt ctactgaatt c                               31

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
agttttgtta tggcaacttt ctactgaatt c                                31

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
agttttgtta tcccaacttt ctactgaatt c                                31

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
agttttgtta tcggaacttt ctactgaatt c                                31

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
agttttgtta tcgctacttt ctactgaatt c                                31

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
agttttgtta tcgcatcttt ctactgaatt c                                31

<210> SEQ ID NO 41
<211> LENGTH: 31
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 41
agttttgtta tcgcaagttt ctactgaatt c                                    31

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aaaagttatc gcaactttct actgaattc                                       29

<210> SEQ ID NO 43
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
agttttgtta tcgcaacatt ctactgaatt cggtcatag                            39

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
agttttgtta tcgcaactat ctactgaatt cggtcatag                            39

<210> SEQ ID NO 45
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
agttttgtta tcgcaactta ctactgaatt cggtcatag                            39

<210> SEQ ID NO 46
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
agttttgtta tcgcaacttt gtactgaatt cggtcatag                            39

<210> SEQ ID NO 47
<211> LENGTH: 39
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 47
agttttgtta tcgcaacttt caactgaatt cggtcatag                              39

<210> SEQ ID NO 48
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
agttttgtta tcgcaacttt cttctgaatt cggtcatag                              39

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
agttttgtta tcgcaacttt ctagtgaatt cggtcatag                              39

<210> SEQ ID NO 50
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
agttttgtta tcgcaacttt ctacagaatt cggtcatag                              39

<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
agtttagtta tcgcaacttt ctactgaatt c                                      31

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
agttatgtta tcgcaacttt ctactgaatt c                                      31

<210> SEQ ID NO 53
<211> LENGTH: 31
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 53
agtattgtta tcgcaacttt ctactgaatt c                                        31

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
agttgtcgtt cctcaactcc ggcgtttc                                            28

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tcgacgccaa taccgtcttt ttcagtgg                                            28

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ctgcctttgc ttctacctttt gcctgt                                             26

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ttgcttctac ctttgcctgt tctgg                                               25

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ttttctggct ggggatggcc gatgg                                               25

<210> SEQ ID NO 59
<211> LENGTH: 50
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 59
agcaataaca ctaatattga ttccttcaga tatggactcc tttcatagta                50

<210> SEQ ID NO 60
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ttgattcctt cagatatgga ctcctttcat agtataacg                            39

<210> SEQ ID NO 61
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tgagcatcgt tattcttacg cgttgtcatt gaaagag                              37

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
agcctgggca acgagtgaaa ctctg                                           25

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
acaggaggga caaaggccta agtgtcc                                         27

<210> SEQ ID NO 64
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
catcatagga ttgggaaaag gacatttcag tcattcag                             38

<210> SEQ ID NO 65
<211> LENGTH: 48
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 65
agagtccttc tttctcaatt tttcagaata atttagtact ttgggtac         48

<210> SEQ ID NO 66
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cagtactgaa aaaacctgcc tatcaataaa agccctagac                  40

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gcttcaccgg ctacctttgc tcct                                   24

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ttcacctgca ggccccgcag g                                      21

<210> SEQ ID NO 69
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cctgactttc aactctgtct ccttcctctt tttacagta                   39

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tgctgtgact gcttgtagat ggccatgg                               28

<210> SEQ ID NO 71
<211> LENGTH: 36
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 71
agtttccaga cctcagtgca caagatactt ttctac                                  36

<210> SEQ ID NO 72
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
acctcagtgc acaagatact tttctacgtc atccac                                  36

<210> SEQ ID NO 73
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
agctccagtg gatggaagat ctttgagatc cag                                     33

<210> SEQ ID NO 74
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
agtcaaagag attcatgcct gggactttaa tcacatttat                              40

<210> SEQ ID NO 75
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
atgcctggga ctttaatcac atttatcgga agg                                     33

<210> SEQ ID NO 76
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
caaatctgtc tccacctctc agctcacctt g                                       31

<210> SEQ ID NO 77
<211> LENGTH: 34
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 77
ttcttgaacc caaactcacc tggcatttaa actg                                      34

<210> SEQ ID NO 78
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
aaactcacct ggcatttaaa ctgactctgt aag                                       33

<210> SEQ ID NO 79
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
aaactcacct ggcatttaaa ctgtctctgt aag                                       33

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tgccgaggct gagttcagct actctcc                                              27

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
acacagcacc gtgggtcaga ccttgc                                               26

<210> SEQ ID NO 82
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tgggtcagac tttgccggtg agagtc                                               26

<210> SEQ ID NO 83
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 83
tgggtcagac tttgctggtg agagtc                                              26

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
agcagtggcc atgtgatgct gatgatg                                             27

<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ccccggctct gttggctttg agaattg                                             27

<210> SEQ ID NO 86
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ctctgttggc tttgagaatt gcctgtctgt gtc                                      33

<210> SEQ ID NO 87
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ctctgttggc tttgagaatt gtctgtctgt gtc                                      33

<210> SEQ ID NO 88
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
accgatacct ggcagcccctt ggatg                                              25

<210> SEQ ID NO 89
<211> LENGTH: 12
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, g, or t

<400> SEQUENCE: 89
nnnnnnnnnn nn                                                           12

<210> SEQ ID NO 90
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gaaattaata cgactcacta taggg                                             25

<210> SEQ ID NO 91
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gaattcagta gaaagttgcg ataaatctac aacagtagaa attccctata gtgagtcgta       60
ttaatttc                                                                68

<210> SEQ ID NO 92
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
agaaagttgc gataaatcta caacagtaga aattccctat agtgagtcgt attaatttc        59

<210> SEQ ID NO 93
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tagaaagttg cgataaatct acaacagtag aaattcccta gtgagtcg tattaatttc         60

<210> SEQ ID NO 94
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 94
gtagaaagtt gcgataaatc tacaacagta gaaattccct atagtgagtc gtattaattt    60
c                                                                   61

<210> SEQ ID NO 95
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
agtagaaagt tgcgataaat ctacaacagt agaaattccc tatagtgagt cgtattaatt    60
tc                                                                  62

<210> SEQ ID NO 96
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gagtaacaga catggaccat cagatctaca acagtagaaa ttccctatag tgagtcgtat    60
taatttc                                                             67

<210> SEQ ID NO 97
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gacatggacc atcaggaaac attatctaca acagtagaaa ttccctatag tgagtcgtat    60
taatttc                                                             67

<210> SEQ ID NO 98
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
aggcgagtaa cagacatgga ccaatctaca acagtagaaa ttccctatag tgagtcgtat    60
taatttc                                                             67

<210> SEQ ID NO 99
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tgacaggcga gtaacagaca tggatctaca acagtagaaa ttccctatag tgagtcgtat    60
taatttc    67

<210> SEQ ID NO 100
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
agacatggac catcagatct acaacagtag aaattcccta tagtgagtcg tattaatttc    60

<210> SEQ ID NO 101
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
acagacatgg accatcagat ctacaacagt agaaattccc tatagtgagt cgtattaatt    60
tc    62

<210> SEQ ID NO 102
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
taacagacat ggaccatcag atctacaaca gtagaaattc cctatagtga gtcgtattaa    60
tttc    64

<210> SEQ ID NO 103
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gacatggacc atcaggaaac attccctata gtgagtcgta ttaatttc    48

<210> SEQ ID NO 104
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
aggcgagtaa cagacatgga ccaccctata gtgagtcgta ttaatttc    48

<210> SEQ ID NO 105
<211> LENGTH: 48

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tgacaggcga gtaacagaca tggccctata gtgagtcgta ttaatttc                    48

<210> SEQ ID NO 106
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
cctcttccca gaacaggatc tacaacagta gaaattccct atagtgagtc gtattaattt       60
c                                                                      61

<210> SEQ ID NO 107
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
cctcttccca gcacaggatc tacaacagta gaaattccct atagtgagtc gtattaattt       60
c                                                                      61

<210> SEQ ID NO 108
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
ctgaagcgtt atactatatc tacaacagta gaaattccct atagtgagtc gtattaattt       60
c                                                                      61

<210> SEQ ID NO 109
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ctgaagcgtt gtactatatc tacaacagta gaaattccct atagtgagtc gtattaattt       60
c                                                                      61

<210> SEQ ID NO 110
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 110
ttttatctga atgattatct acaacagtag aaattcccta tagtgagtcg tattaatttc    60

<210> SEQ ID NO 111
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ttttatctga atgactatct acaacagtag aaattcccta tagtgagtcg tattaatttc    60

<210> SEQ ID NO 112
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
aaaaaagagt gagtaccatc tacaacagta gaaattccct atagtgagtc gtattaattt    60
c                                                                   61

<210> SEQ ID NO 113
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
aaaaaagagt gggtaccatc tacaacagta gaaattccct atagtgagtc gtattaattt    60
c                                                                   61

<210> SEQ ID NO 114
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ggtagaaggt ccaggagatc tacaacagta gaaattccct atagtgagtc gtattaattt    60
c                                                                   61

<210> SEQ ID NO 115
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ggtagaaggt ctaggagatc tacaacagta gaaattccct atagtgagtc gtattaattt    60
c                                                                   61

<210> SEQ ID NO 116

```
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gggcagggga gtactgatct acaacagtag aaattcccta tagtgagtcg tattaatttc      60

<210> SEQ ID NO 117
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gggcagggga ctactgatct acaacagtag aaattcccta tagtgagtcg tattaatttc      60

<210> SEQ ID NO 118
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
tcagtggatg atgtaatcta caacagtaga aattccctat agtgagtcgt attaatttc       59

<210> SEQ ID NO 119
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tcagtggatg acgtaatcta caacagtaga aattccctat agtgagtcgt attaatttc       59

<210> SEQ ID NO 120
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ggaaattctc cttccgaatc tacaacagta gaaattccct atagtgagtc gtattaattt      60
c                                                                     61

<210> SEQ ID NO 121
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ggaaattctc cttccaaatc tacaacagta gaaattccct atagtgagtc gtattaattt      60
c                                                                     61
```

<210> SEQ ID NO 122
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
tcttacagag tcagttatct acaacagtag aaattcccta tagtgagtcg tattaatttc     60

<210> SEQ ID NO 123
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tcttacagag ccagttatct acaacagtag aaattcccta tagtgagtcg tattaatttc     60

<210> SEQ ID NO 124
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gtcttacaga gacagttatc tacaacagta gaaattccct atagtgagtc gtattaattt     60
c                                                                    61

<210> SEQ ID NO 125
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ctggactctc accggatcta caacagtaga aattccctat agtgagtcgt attaatttc      59

<210> SEQ ID NO 126
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ctggactctc accagatcta caacagtaga aattccctat agtgagtcgt attaatttc      59

<210> SEQ ID NO 127
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
cacagacagg caattctatc tacaacagta gaaattccct atagtgagtc gtattaattt    60
c                                                                   61

<210> SEQ ID NO 128
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
cacagacaga caattctatc tacaacagta gaaattccct atagtgagtc gtattaattt    60
c                                                                   61

<210> SEQ ID NO 129
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tcgcgcttgt cgcgcagacg aatgatctac aacagtagaa attccctata gtgagtcgta    60
ttaatttc                                                            68

<210> SEQ ID NO 130
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
catggtgcgt ttctggcc                                                 18

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
cggcgttttg ttcttgttca                                               20

<210> SEQ ID NO 132
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
acaactcacg cagacgtttc gcaaccttca ccaatgtgac cg                      42

<210> SEQ ID NO 133
<211> LENGTH: 41

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gttcctcaac tccggcgttt ccgatgccgc cttcatagtg g                         41

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
cagaatttca tattcgaact                                                 20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gacggcaaag aagaccactt                                                 20

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
cgacggcaaa gaagacca                                                   18

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
agcctgccag gtgagtac                                                   18

<210> SEQ ID NO 138
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
cgggtggatc ggcgttttgt tcactatgaa ggcggcatca                           40

<210> SEQ ID NO 139
<211> LENGTH: 40
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 139
gtattggcgt cgaagtggcg ttcgctgcgg aatgttgttg                           40

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ttgttcagat attcaacgaa cg                                              22

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gtggaacgat ggcttccagg                                                 20

<210> SEQ ID NO 142
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
cagctgtaga ccataagcc                                                  19

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gtggctgagc atcgttat                                                   18

<210> SEQ ID NO 144
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
actatgaaag gagtccatat ctgaaggaat tcaggtagtg gtttggga                  48

<210> SEQ ID NO 145
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 145
gcttcagcct actgcaaatc ctacgcgttg tcattgaaag                           40

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
tcaatattag tgttattgct tg                                             22

<210> SEQ ID NO 147
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
tggtggaaga tttggacagg ac                                             22

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gctggaaagg tcaagggac                                                 19

<210> SEQ ID NO 149
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ggggtttgtt gcacagtcc                                                 19

<210> SEQ ID NO 150
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
caaaggtaga agcaaaggca ggaggtttgc ccaaggtcac acag                     44

<210> SEQ ID NO 151
<211> LENGTH: 41
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 151
ctgggaagag ggagggctca gtgttgccac actttcactg g                          41

<210> SEQ ID NO 152
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
gtgagcgggt ggggtgct                                                    18

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
tctaagtctt ccagcacggg atc                                              23

<210> SEQ ID NO 154
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
atatgaaatt ctggcgaaac gtctgcgtga gttg                                  34

<210> SEQ ID NO 155
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
aaacgtctgc gtgagttgtc gttcctcaac tcc                                   33

<210> SEQ ID NO 156
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
acttcgacgc caataccgtc tttttcagtg gag                                   33

<210> SEQ ID NO 157
<211> LENGTH: 59
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 157
atctgagaag tggcacttat cgcaactttc tactgaggtc atagctgttt cctgtgtga      59

<210> SEQ ID NO 158
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gtcctctaga cccctatagt gagtcgtatt aatttcatga ttacgaattc gagctcggt      59

<210> SEQ ID NO 159
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
ccactttcca ggtggcaaag cccgttgagc ttctcaaatc tgagaagtgg cacttatc       58

<210> SEQ ID NO 160
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
tggaaagtgg ccattggcac acccgttgaa aaattctgtc ctctagaccc ctatagtga      59

<210> SEQ ID NO 161
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
gaaattaata cgactcacta taggg                                           25

<210> SEQ ID NO 162
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tcagtagaaa gttgcgataa gtgc                                            24

<210> SEQ ID NO 163
<211> LENGTH: 23
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 163
aacagacatg gaccatcagg gtg    23

<210> SEQ ID NO 164
<211> LENGTH: 66
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 164
tttctgtttg ttatcgcaac tttctactga attcaagctt tactctagaa agaggagaaa    60
ggatcc    66

<210> SEQ ID NO 165
<211> LENGTH: 66
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 165
ggatcctttc tcctctttct agagtaaagc ttgaattcag tagaaagttg cgataacaaa    60
cagaaa    66

<210> SEQ ID NO 166
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 166
gtcacgccac ttgacaggcg agtaacagac atggaccatc aggaaacatt    50

<210> SEQ ID NO 167
<211> LENGTH: 66
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 167
ggatcctttc tcctctttct agagtaaagc ttgaattcag tagaaagttg cgataacaaa    60
cagaaa    66

<210> SEQ ID NO 168
<211> LENGTH: 66
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 168
tttctgtttg ttatcgcaac tttctactga attcaagctt tactctagaa agaggagaaa    60
ggatcc    66

<210> SEQ ID NO 169
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
cctgatggtc catgtctgtt ggtcatagct gtttcctgtg tg                       42

<210> SEQ ID NO 170
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
tggaccatca gggtgccact tctcagattt gagaag                              36

<210> SEQ ID NO 171
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gaaattaata cgactcacta taggg                                          25

<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
aacagacatg gaccatcagg gtg                                            23

<210> SEQ ID NO 173
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
aatgttccct gatggtccat gtctgttact cgcctgtcaa gtggcgtgac                50

<210> SEQ ID NO 174
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gtcacgccac ttgacaggcg agtaacagac atggaccatc agggaacatt                50

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 175
gtgaacgttc ccttagcact                                                     20

<210> SEQ ID NO 176
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 176
gggagggcag aactagtcc                                                      19

<210> SEQ ID NO 177
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 177
cgccacttga caggcgagta actgccactt attgggtcag c                             41

<210> SEQ ID NO 178
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 178
gcgtgttccc cagagtgact tagcagcttc ctcctcctt                                39

<210> SEQ ID NO 179
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 179
aggaaacatt aacgtactga tg                                                  22

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 180 ttcctttat ttcccttcag c                                                    21

```
<210> SEQ ID NO 181
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
gtcacgccac ttgacaggcg agtaacagac atggaccatc agggaacatt              50

<210> SEQ ID NO 182
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
aatgttccct gatggtccat gtctgttact cgcctgtcaa gtggcgtgac              50

<210> SEQ ID NO 183
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183
gtctagagga cagaattttt caacgggtgt gccaatggcc actttccagg tggcaaagcc   60
cgttgagctt ctcaaatctg agaagtggca ccctgatggt ccatgtctgt t           111

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
cctgatggtc catgtctgtt                                               20

<210> SEQ ID NO 185
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
gtcacgccac ttgacaggcg agtaacagac atggaccatc agggaacatt              50

<210> SEQ ID NO 186
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
gtcacgccac ttgacaggcg agtaacagac atggaccatc agggaacatt              50
```

<210> SEQ ID NO 187
<211> LENGTH: 1129
<212> TYPE: PRT
<213> ORGANISM: Alicyclobacillus acidoterrestris

<400> SEQUENCE: 187

```
Met Ala Val Lys Ser Ile Lys Val Lys Leu Arg Leu Asp Asp Met Pro
1               5                   10                  15

Glu Ile Arg Ala Gly Leu Trp Lys Leu His Lys Glu Val Asn Ala Gly
            20                  25                  30

Val Arg Tyr Tyr Thr Glu Trp Leu Ser Leu Leu Arg Gln Glu Asn Leu
        35                  40                  45

Tyr Arg Arg Ser Pro Asn Gly Asp Gly Glu Gln Glu Cys Asp Lys Thr
    50                  55                  60

Ala Glu Glu Cys Lys Ala Glu Leu Leu Glu Arg Leu Arg Ala Arg Gln
65                  70                  75                  80

Val Glu Asn Gly His Arg Gly Pro Ala Gly Ser Asp Asp Glu Leu Leu
                85                  90                  95

Gln Leu Ala Arg Gln Leu Tyr Glu Leu Leu Val Pro Gln Ala Ile Gly
            100                 105                 110

Ala Lys Gly Asp Ala Gln Gln Ile Ala Arg Lys Phe Leu Ser Pro Leu
        115                 120                 125

Ala Asp Lys Asp Ala Val Gly Gly Leu Gly Ile Ala Lys Ala Gly Asn
    130                 135                 140

Lys Pro Arg Trp Val Arg Met Arg Glu Ala Gly Glu Pro Gly Trp Glu
145                 150                 155                 160

Glu Glu Lys Glu Lys Ala Glu Thr Arg Lys Ser Ala Asp Arg Thr Ala
                165                 170                 175

Asp Val Leu Arg Ala Leu Ala Asp Phe Gly Leu Lys Pro Leu Met Arg
            180                 185                 190

Val Tyr Thr Asp Ser Glu Met Ser Ser Val Glu Trp Lys Pro Leu Arg
        195                 200                 205

Lys Gly Gln Ala Val Arg Thr Trp Asp Arg Asp Met Phe Gln Gln Ala
    210                 215                 220

Ile Glu Arg Met Met Ser Trp Glu Ser Trp Asn Gln Arg Val Gly Gln
225                 230                 235                 240

Glu Tyr Ala Lys Leu Val Glu Gln Lys Asn Arg Phe Glu Gln Lys Asn
                245                 250                 255

Phe Val Gly Gln Glu His Leu Val His Leu Val Asn Gln Leu Gln Gln
            260                 265                 270

Asp Met Lys Glu Ala Ser Pro Gly Leu Glu Ser Lys Glu Gln Thr Ala
        275                 280                 285

His Tyr Val Thr Gly Arg Ala Leu Arg Gly Ser Asp Lys Val Phe Glu
    290                 295                 300

Lys Trp Gly Lys Leu Ala Pro Asp Ala Pro Phe Asp Leu Tyr Asp Ala
305                 310                 315                 320

Glu Ile Lys Asn Val Gln Arg Arg Asn Thr Arg Arg Phe Gly Ser His
                325                 330                 335

Asp Leu Phe Ala Lys Leu Ala Glu Pro Glu Tyr Gln Ala Leu Trp Arg
            340                 345                 350

Glu Asp Ala Ser Phe Leu Thr Arg Tyr Ala Val Tyr Asn Ser Ile Leu
        355                 360                 365

Arg Lys Leu Asn His Ala Lys Met Phe Ala Thr Phe Thr Leu Pro Asp
    370                 375                 380
```

-continued

```
Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Arg Arg His
                405                 410                 415

Ala Ile Arg Phe His Lys Leu Leu Lys Val Glu Asn Gly Val Ala Arg
                420                 425                 430

Glu Val Asp Asp Val Thr Val Pro Ile Ser Met Ser Glu Gln Leu Asp
                435                 440                 445

Asn Leu Leu Pro Arg Asp Pro Asn Glu Pro Ile Ala Leu Tyr Phe Arg
        450                 455                 460

Asp Tyr Gly Ala Glu Gln His Phe Thr Gly Phe Gly Gly Ala Lys
465                 470                 475                 480

Ile Gln Cys Arg Arg Asp Gln Leu Ala His Met His Arg Arg Arg Gly
                485                 490                 495

Ala Arg Asp Val Tyr Leu Asn Val Ser Val Arg Val Gln Ser Gln Ser
                500                 505                 510

Glu Ala Arg Gly Glu Arg Arg Pro Pro Tyr Ala Ala Val Phe Arg Leu
        515                 520                 525

Val Gly Asp Asn His Arg Ala Phe Val His Phe Asp Lys Leu Ser Asp
        530                 535                 540

Tyr Leu Ala Glu His Pro Asp Asp Gly Lys Leu Gly Ser Gly Leu
545                 550                 555                 560

Leu Ser Gly Leu Arg Val Met Ser Val Asp Leu Gly Leu Arg Thr Ser
                565                 570                 575

Ala Ser Ile Ser Val Phe Arg Val Ala Arg Lys Asp Glu Leu Lys Pro
                580                 585                 590

Asn Ser Lys Gly Arg Val Pro Phe Phe Phe Pro Ile Lys Gly Asn Asp
        595                 600                 605

Asn Leu Val Ala Val His Glu Arg Ser Gln Leu Leu Lys Leu Pro Gly
        610                 615                 620

Glu Thr Glu Ser Lys Asp Leu Arg Ala Ile Arg Glu Glu Arg Gln Arg
625                 630                 635                 640

Thr Leu Arg Gln Leu Arg Thr Gln Leu Ala Tyr Leu Arg Leu Leu Val
                645                 650                 655

Arg Cys Gly Ser Glu Asp Val Gly Arg Arg Glu Arg Ser Trp Ala Lys
                660                 665                 670

Leu Ile Glu Gln Pro Val Asp Ala Ala Asn His Met Thr Pro Asp Trp
        675                 680                 685

Arg Glu Ala Phe Glu Asn Glu Leu Gln Lys Leu Lys Ser Leu His Gly
        690                 695                 700

Ile Cys Ser Asp Lys Glu Trp Met Asp Ala Val Tyr Glu Ser Val Arg
705                 710                 715                 720

Arg Val Trp Arg His Met Gly Lys Gln Val Arg Asp Trp Arg Lys Asp
                725                 730                 735

Val Arg Ser Gly Glu Arg Pro Lys Ile Arg Gly Tyr Ala Lys Asp Val
                740                 745                 750

Val Gly Gly Asn Ser Ile Glu Gln Ile Glu Tyr Leu Glu Arg Gln Tyr
        755                 760                 765

Lys Phe Leu Lys Ser Trp Ser Phe Gly Lys Val Ser Gly Gln Val
        770                 775                 780

Ile Arg Ala Glu Lys Gly Ser Arg Phe Ala Ile Thr Leu Arg Glu His
785                 790                 795                 800
```

-continued

```
Ile Asp His Ala Lys Glu Asp Arg Leu Lys Leu Ala Asp Arg Ile
            805                 810                 815

Ile Met Glu Ala Leu Gly Tyr Val Tyr Ala Leu Asp Glu Arg Gly Lys
            820                 825                 830

Gly Lys Trp Val Ala Lys Tyr Pro Pro Cys Gln Leu Ile Leu Leu Glu
            835                 840                 845

Glu Leu Ser Glu Tyr Gln Phe Asn Asn Asp Arg Pro Pro Ser Glu Asn
    850                 855                 860

Asn Gln Leu Met Gln Trp Ser His Arg Gly Val Phe Gln Glu Leu Ile
865                 870                 875                 880

Asn Gln Ala Gln Val His Asp Leu Leu Val Gly Thr Met Tyr Ala Ala
            885                 890                 895

Phe Ser Ser Arg Phe Asp Ala Arg Thr Gly Ala Pro Gly Ile Arg Cys
            900                 905                 910

Arg Arg Val Pro Ala Arg Cys Thr Gln Glu His Asn Pro Glu Pro Phe
        915                 920                 925

Pro Trp Trp Leu Asn Lys Phe Val Val Glu His Thr Leu Asp Ala Cys
        930                 935                 940

Pro Leu Arg Ala Asp Asp Leu Ile Pro Thr Gly Glu Gly Glu Ile Phe
945                 950                 955                 960

Val Ser Pro Phe Ser Ala Glu Glu Gly Asp Phe His Gln Ile His Ala
            965                 970                 975

Asp Leu Asn Ala Ala Gln Asn Leu Gln Gln Arg Leu Trp Ser Asp Phe
            980                 985                 990

Asp Ile Ser Gln Ile Arg Leu Arg  Cys Asp Trp Gly Glu  Val Asp Gly
            995                 1000                1005

Glu Leu  Val Leu Ile Pro Arg  Leu Thr Gly Lys Arg  Thr Ala Asp
    1010                1015                1020

Ser Tyr  Ser Asn Lys Val Phe  Tyr Thr Asn Thr Gly  Val Thr Tyr
    1025                1030                1035

Tyr Glu  Arg Glu Arg Gly Lys  Lys Arg Arg Lys Val  Phe Ala Gln
    1040                1045                1050

Glu Lys  Leu Ser Glu Glu Glu  Ala Glu Leu Leu Val  Glu Ala Asp
    1055                1060                1065

Glu Ala  Arg Glu Lys Ser Val  Val Leu Met Arg Asp  Pro Ser Gly
    1070                1075                1080

Ile Ile  Asn Arg Gly Asn Trp  Thr Arg Gln Lys Glu  Phe Trp Ser
    1085                1090                1095

Met Val  Asn Gln Arg Ile Glu  Gly Tyr Leu Val Lys  Gln Ile Arg
    1100                1105                1110

Ser Arg  Val Pro Leu Gln Asp  Ser Ala Cys Glu Asn  Thr Gly Asp
    1115                1120                1125

Ile
```

APPLICATION OF CAS PROTEIN, METHOD FOR DETECTING TARGET NUCLEIC ACID MOLECULE AND KIT

SEQUENCE LISTING

The instant application contains a Sequence Listing which has been submitted electronically in ASCII format and is hereby incorporated by reference in its entirety. Said ASCII copy, created on May 6, 2020, is named 2013065-0286_SL.txt and is 56,958 bytes in size.

TECHNICAL FIELD

The present invention belongs to the field of biotechnology, and in particular, the present invention relates to a method for the detection of target nucleic acid molecules.

BACKGROUND

Specific detection method of nucleic acids has important values in applications such as pathogen detection, genetic disease detection and the like. For pathogen detections, because each pathogenic microorganism has its unique characteristic nucleic acid sequences, the detection of nucleic acid molecules for specific species can be developed, also known as nucleic acid diagnostics (NADs), plays an important role in the field of food safety, environmental microbial pollution detection, human pathogen infections and the like. In another aspect, the NAD methods can also detect single nucleotide polymorphisms (SNPs) in human beings or other species. Understanding the relationship between genetic variation and biological function at the genomic level may provide anew perspective for modern molecular biology, among which SNPs are closely related to biological function, evolution, disease and the like, thus the development of techniques for detection and analysis of SNPs is particularly important.

So far, several NAD methods have been established, most of which are created for the detection of specific DNA molecules and some of which are for RNA molecules. Usually, DNA molecules are very stable and detection samples can be from a series of complex biological samples, while RNA molecules can be easily degraded and should be treated with care. In 1970s, restriction endonuclease digestion detection methods were developed, and then by the development of methods for detection of specific nucleic acid molecules such as Southern, Northern and dot hybridization. In 1985 when the PCR method became a routine experimental method, it led to exponential progress in molecular biology. The detection of specific nucleic acid molecules currently established usually requires two steps, the first step being target nucleic acid amplification and the second step being target nucleic acid detection. PCR technique is the first established and currently most commonly used amplification method. Based on the PCR method, fluorescence labelled probes are introduced to facilitate realtime detection of the amplification of target (named as Realtime PCR), which is a rapid and highly sensitive detection method and can be used for quantitative analysis. Besides of PCR amplification method, many alternative methods have been created, such as the ligase chain reaction, the branched DNA amplification, NASBA, SDA, transcription-mediated amplification, loop-mediated isothermal amplification (LAMP), rolling circle amplification (RCA), Recombinase Polymerase Amplification (RPA) and the like. The advantage of these alternative methods lies in the isothermal characteristic, that's to say that the reaction can be simply accomplished at one temperature, without the need for thermal cycling instruments for PCR. In addition to real-time PCR, which can directly complete amplification and detection, among nucleic acid detection methods, FISH hybridization technology (Fluorescence in situ hybridization), the most commonly used detection method, hybridizes in situ with complementary target sequences by labeling molecular probes. In addition, detection methods such as next-generation sequencing technologies and Oxford Nanopore sequencing technologies have also been developed, but these methods usually require expensive experimental equipment.

The detection of SNPs first also needs to be amplified by PCR and other methods to obtain enough amounts of fragments containing SNP site regions for further detection. Common approaches include primer extension, hybridization, ligation and enzymatic cleavage. After completing the above methods, you need to use specific methods for detection, such as mass spectrometry detection, fluorescence detection, chemiluminescence detection, etc.

Although many detection methods have been developed as described above for nucleic acid detection, in some cases, faster, simpler and cheaper detection is still an important development direction, such as rapid detection of pathogens in the wild, rapid detection of drug-sensitive SNPs, etc. In 2016, Collins et al. developed a rapid and inexpensive method for detecting Zika virus based on the characteristics of CRISPR-Cas9 that specifically recognizes and cleaves target sequences. In 2017, Zhang Feng et al. took advantage of the collateral effect of CRISPR-Cas13a to build a rapid nucleic acid detection method. "Collateral effect", i.e., Cas13a binds to specific target RNA and then randomly cleaves other non-target RNAs (here, the RNA molecule is designed as an RNA fluorescence reporter system), combined with isothermal amplification technology RPA to achieve rapid target RNA detection; and Zhang Feng team called this detection method as SHERLOCK (Specific High Sensitivity Enzymatic Reporter UnLOCKing). The SHERLOCK method involves the binding of RNA templates, so if you need to detect DNA, DNA should be first transcribed to RNA for detection; in view of the instability of RNA, this method will undoubtedly increase the difficulty of operation.

In 2015, Zhang Feng et al. discovered a new CRISPR-associated protein endonuclease Cas12a (formerly known as Cpf1), which is an RNA-guided specific DNA endonuclease like the commonly used Cas9 protein; but compared with Cas9, Cas12a has its own characteristics, such as the need for crRNA to guide the specific cleavage of double-stranded DNA and produce cohesive ends.

SUMMARY OF THE INVENTION

The object of the present invention is to provide a method for detecting target nucleic acid molecules.

Another object of the present invention is to provide a use of a Cas protein in a method for detecting target nucleic acid molecules.

In a first aspect of the invention, provided is a kit, comprising a guide RNA, a Cas protein, a nucleic acid probe and a buffer.

provided is a method for detecting target nucleic acid molecules, which comprises adding a guide RNA, a Cas protein, a nucleic acid probe and a buffer into the reaction system containing the target nucleic acid molecules to be detected, and then detecting the target nucleic acid molecules (especially by detection of the fluorescence intensity).

Preferably, the Cas protein is Cas12a or a Cas protein having an activity similar to the collateral single-stranded DNA cleavage activity of Cas12a.

Preferably, the Cas protein is Cas12a.

The Cas12a is preferably one of FnCas12a, AsCas12a, LbCas12a, Lb5Cas12a, HkCas12a, OsCas12a, TsCas12a, BbCas12a, BoCas12a or Lb4Cas12a.

Preferably, the Cas12a is LbCas12a.

Preferably, the guide RNA refers to an RNA that directs the Cas protein to specifically bind to the target DNA.

In another preferred embodiment, the nucleic acid probe is a single-stranded DNA; the single-stranded DNA is preferably a fluorescently labelled single-stranded DNA; and the single-stranded DNA is preferably a fluorescent probe labelled with a fluorescent group HEX at the 5' end and a quenching group BHQ1 at the 3' end.

In another preferred embodiment, the detection method of the nucleic acid probe is preferably a fluorescence detection method; and the fluorescence detection method is preferably by using a microplate reader or a fluorescence spectrophotometer.

Preferably, the target nucleic acid molecules to be detected in the reaction system of the target nucleic acid molecules to be detected are obtained after amplification.

Preferably, the detection method of the present invention can detects pathogenic microorganisms, gene mutations or specific target DNA.

In another preferred embodiment, the Cas protein comprises Cas12b (C2c1).

In a second aspect of the invention, provided is a use of a Cas protein in a method for detecting target nucleic acid molecules, or for preparing a preparation for the detection of target nucleic acid molecules.

In another preferred embodiment, when the target DNA, the guide RNA and the Cas protein form a ternary complex, the complex cleaves other single-stranded DNA molecules in the system.

Preferably, the guide RNA refers to an RNA that directs the Cas protein to specifically bind to the target DNA.

In a third aspect of the invention, provided is a kit comprising a guide RNA, a Cas protein and a nucleic acid probe.

In another preferred embodiment, the kit further comprises a buffer.

In a fourth aspect of the invention, provided is a detection system for detecting target nucleic acid molecules, comprising:
  (a) a Cas protein, which is Cas12a or a Cas protein having an activity similar to the collateral single-stranded DNA cleavage activity of Cas12a;
  (b) a guide RNA, which directs the Cas protein to specifically bind to target nucleic acid molecules; and
  (c) a nucleic acid probe, which is a single-stranded DNA;
  Wherein the target nucleic acid molecule is a target DNA.

In another preferred embodiment, the detection system further comprises (d) a buffer.

In another preferred embodiment, the detection system further comprises target nucleic acid molecules to be detected.

In another preferred embodiment, the concentration of the target nucleic acid molecules to be detected in the detection system is from 1 to 100 copies/μL or $10^{15}$ copies/μL, preferably from 1 to 10 copies/μL, more preferably from 1 to 5 copies/μL.

In another preferred embodiment, in the detection system, the molar ratio of the nucleic acid probe to the target nucleic acid molecule is from $10^3$:1 to $10^{14}$:1, preferably from $10^4$:1 to $10^7$:1.

In another preferred embodiment, the detection site of the target nucleic acid molecule is located at positions 1-12 downstream of the PAM sequence of the guide RNA.

In another preferred embodiment, the length of the guide RNA is 15-30 nt, preferably 15-18 nt.

In another preferred embodiment, the target DNA comprises cDNA.

In another preferred embodiment, the target DNA is selected from the group consisting of: single-stranded DNA, double-stranded DNA, or a combination thereof.

In another preferred embodiment, the nucleic acid probe has a fluorescent group and a quenching group.

In another preferred embodiment, the fluorescent group and the quenching group are each independently located at the 5' end, the 3' end, and the middle of the nucleic acid probe.

In another preferred embodiment, the length of the nucleic acid probe is from 3 to 300 nt, preferably from 5 to 100 nt, more preferably from 6 to 50 nt, and most preferably from 8 to 20 nt.

In another preferred embodiment, the target nucleic acid molecules comprise target nucleic acid molecules derived from a species selected from the group consisting of: a plant, an animal, an insect, a microorganism, a virus, or a combination thereof.

In another preferred embodiment, the target DNA is a artificially synthesized or a naturally occurring DNA.

In another preferred embodiment, the target DNA comprises a wild-type or a mutant DNA.

In another preferred embodiment, the target DNA comprises DNA obtained by RNA reverse transcription or amplification, such as cDNA and the like.

In another preferred embodiment, the Cas12a is selected from the group consisting of: FnCas12a, AsCas12a, LbCas12a, Lb5Cas12a, HkCas12a, OsCas12a, TsCas12a, BbCas12a, BoCas12a, Lb4Cas12a or a combination thereof more preferably, the Cas12a is LbCas12a.

In another preferred embodiment, the Cas protein having an activity similar to the collateral single-stranded DNA cleavage activity of Cas12a is selected from the group consisting of: Cas12b (i.e., C2c1).

In another preferred embodiment, the Cas12b protein is selected from the group consisting of: AacCas12b (*Alicyclobacillus acidoterrestris*), Aac2Cas12b (*Alicyclobacillus acidiphilus*), AkCas12b (*Alicyclobacillus kakegawensis*), AmCas12b (*Alicyclobacillus macrosporangiidus*), AhCas12b (*Alicyclobacillus herbarius*), and AcCas12b (*Alicyclobacillus contaminans*).

In another preferred embodiment, the nucleic acid probe comprises a single-stranded DNA with a detectable label.

In another preferred embodiment, the single-stranded DNA is a single-stranded DNA labelled with fluorescence and biotin.

In another preferred embodiment, the single-stranded DNA is a single-stranded DNA labelled with fluorescence.

In another preferred embodiment, the single-stranded DNA is a fluorescent probe labelled with a fluorescent group HEX at the 5' end and a quenching group BHQ1 at the 3' end.

In a fifth aspect of the invention, provided is a kit for detecting target nucleic acid molecules, comprising:
  i) a first container and a Cas protein located in the first container, wherein the Cas protein is Cas12a or a Cas protein having an activity similar to the collateral single-stranded DNA cleavage activity of Cas12a;

ii) optionally a second container and a guide RNA located in the second container, wherein the guide RNA directs the Cas protein to specifically bind to the target nucleic acid molecules;

iii) a third container and a nucleic acid probe located in the third container;

iv) optionally a fourth container and a buffer located in the fourth container;

Wherein the target nucleic acid molecule is a target DNA.

In another preferred embodiment, any two, three, or four (or all) of the first, second, third, and fourth container may be the same or different container.

In another preferred embodiment, the nucleic acid probe has a fluorescent group and a quenching group.

In a sixth aspect of the invention, provided is a method for detecting whether target nucleic acid molecules are present in a sample, characterized by comprising the steps of:

(a) providing a detection system for detecting target nucleic acid molecules according to the fourth aspect of the invention, and the detection system further contains a sample to be detected; and (b) detecting whether the nucleic acid probe in the detection system is cleaved by the Cas protein, wherein the cleavage is a trans-cleavage of the collateral single-stranded DNA;

Wherein, if the nucleic acid probe is cleaved by the Cas protein, it indicates that the target nucleic acid molecule is present in the sample; and if the nucleic acid probe is not cleaved by the Cas protein, it indicates that the target nucleic acid molecule is not present in the sample.

In another preferred embodiment, the sample to be detected comprises an unamplified sample and an amplified (or nucleic acid amplified) sample.

In another preferred embodiment, the sample to be detected is a sample obtained by amplification.

In another preferred embodiment, the nucleic acid amplification method is selected from the group consisting of: PCR amplification, LAMP amplification, RPA amplification, ligase chain reaction, branched DNA amplification, NASBA, SDA, transcription-mediated amplification, rolling circle amplification, HDA, SPIA, NEAR, TMA and SMAP2.

In another preferred embodiment, the PCR comprises high temperature PCR, normal temperature PCR, and low temperature PCR.

In another preferred embodiment, the method is for detecting whether there is an SNP, a point mutation, a deletion, and/or an insertion for nucleic acids at a target site.

In another preferred embodiment, when the PAM sequence is absent at the upstream or downstream of the target site (in the range of from −20 nt to +20 nt, preferably in the range of from −15 nt to +15 nt, and more preferably in the range of from −10 nt to +10 nt), nucleic acid amplification was carried out using primers introduced with PAM.

In another preferred embodiment, the primer introduced with PAM has a structure of formula I from 5' to 3':

wherein,

P1 is a 5' segment sequence complementary or non-complementary to the sequence of the target nucleic acid molecule at the 5' end;

P2 is a PAM sequence; and

P3 is a 3' segment sequence complementary to the sequence of the target nucleic acid molecule at the 3' end.

In another preferred embodiment, the PAM primer specifically binds upstream or downstream of the target nucleic acid molecule.

In another preferred embodiment, P1 has a length of 0 to 20 nt.

In another preferred embodiment, P3 has a length of 5 to 20 nt.

In another preferred embodiment, the PAM primer has a length of 18 to 50 nt, preferably 20 to 35 nt.

In another preferred embodiment, the complementation comprises full complementation and partial complementation.

In another preferred embodiment, at least one primer with a PAM sequence is used in the nucleic acid amplification.

In another preferred embodiment, when the PAM sequence is present at the upstream or downstream of the target site (in the range of from −20 nt to +20 nt, preferably in the range of from −15 nt to +15 nt, and more preferably in the range of from −10 nt to +10 nt), primers with or without a PAM sequence can be used, and the amplified amplification product contains the PAM sequence.

In another preferred embodiment, the detection in step (b) comprises a fluorescence detection method.

In another preferred embodiment, a microplate reader or a fluorescence spectrophotometer is used in the fluorescence detection method.

In a seventh aspect of the invention, provided is a use of a Cas protein for the preparation of a detection reagent or kit for detecting target nucleic acid molecules based on a collateral single-stranded DNA cleavage, wherein the Cas protein is Cas12a or a Cas protein having an activity similar to the collateral single-stranded DNA cleavage activity of Cas12a.

In another preferred embodiment, the Cas12a is selected from the group consisting of: FnCas12a, AsCas12a, LbCas12a, Lb5Cas12a, HkCas12a, OsCas12a, TsCas12a, BbCas12a, BoCas12a, Lb4Cas12a or a combination thereof; more preferably, the Cas12a is LbCas12a.

In another preferred embodiment, the Cas protein having an activity similar to the collateral single-stranded DNA cleavage activity of Cas is selected from the group consisting of: Cas12b (or C2c1).

In another preferred embodiment, the Cas12b protein is selected from the group consisting of: AacCas12b.

It should be understood that within the scope of the present invention, the various technical features of the present invention above and the various technical features specifically described hereinafter (as in the Examples) may be combined with each other to constitute a new or preferred technical solution. Due to space limitations, it is not repeated here.

DESCRIPTION OF FIGURE

FIG. 20 shows the detection of the genotypes of human HEK293T cells through the combination detection of LAMP and HOLMES. (A) The electrophoretogram of SNP detection template corresponding to human HEK293T amplified by LAMP. Negative control: The sample was sterilized water, and the amplification result was detected with rs5082 amplification primers. rs5082: The sample was the total genomic DNA from human HEK293T cells, and the amplification result was detected with rs5082 amplification primers. rs1467558: The sample was the genomic DNA from human HEK293T cells, and the amplification result was detected with rs1467558 amplification primers. (B) Detection of the LAMP amplification product with HOLMES detection system. Two crRNAs, crRNA-G and crRNA-T were used for detection of the rs5082 site (Sequence Listing 5), respectively, and two crRNAs, crRNA-C and crRNA-T were used for detection of the rs1467558 site (Sequence Listing 5), respectively.

DETAILED DESCRIPTION

Figure 1A:
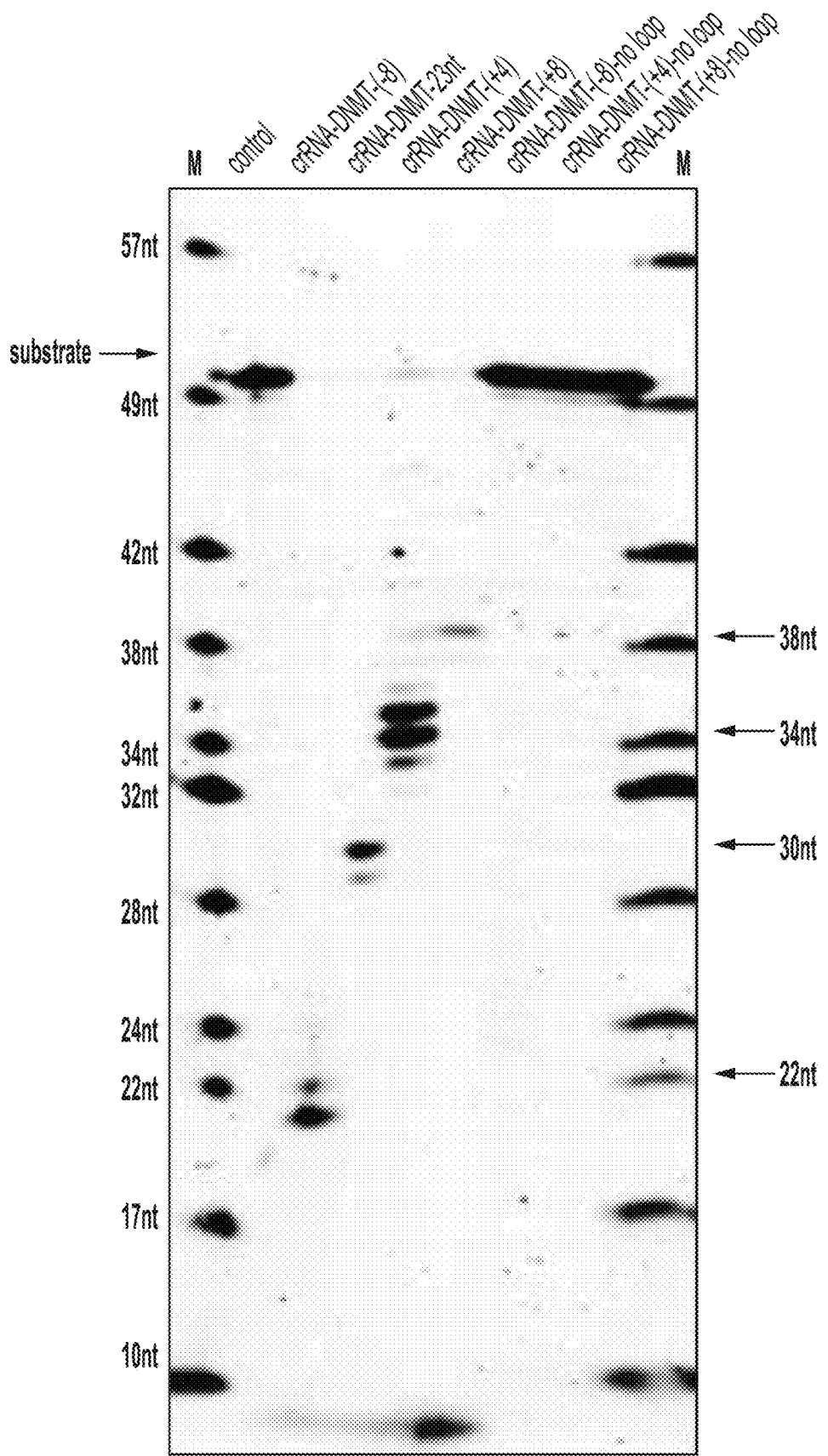
FIG. 1 shows the cis-cleavage characteristics of the Cas12a cleaving target single-stranded DNA.
FIGS. 1C and 1D discloses SEQ ID NOS 3 and 3, respectively, in order of appearance.

In order to make the aim, technical solution and advantages of the Examples of the present invention clearer, the technical solutions in the embodiments of the present invention will be clearly and completely described in conjunction with the drawings in the Examples of the present invention. Obviously, the Examples described herein are not all of the Examples of the present invention. All other Examples obtained by those skilled in the art based on the Examples of the present invention without creative efforts are within the scope of the present invention.

By extensively and intensively studies, the present inventors have developed a technical solution for target nucleic acid detection, by studying the cleavage properties of Cas enzymes such as Cas12a and Cas12b enzymes. The experimental results show that the above technical solutions are successfully used to rapidly detect nucleic acids. For example, identification of whether the water contains a certain concentration of microorganisms such as *Escherichia coli* and rapid identification of SNP genotypes are accomplished. On this basis, the present invention has been completed.

The Terms

The term "guide RNA" refers to an RNA that directs the Cas protein to specifically bind to a target DNA sequence.

The term "crRNA" refers to CRISPR RNA, which is a short RNA that directs Cas12a to bind to a target DNA sequence.

The term "CRISPR" refers to clustered regular interspaced short palindromic repeats, which are the immune systems of many prokaryotes.

The term "Cas protein" refers to a CRISPR-associated protein which is a related protein in the CRISPR system.

The term "Cas12a" (formerly "Cpf1") refers to a crRNA-dependent endonuclease, which is an enzyme of type V-A in the CRISPR system classification.

The terms "Cas12b", and "C2c1" are used interchangeably and refer to a crRNA-dependent endonuclease, which is an enzyme of type V-B in the CRISPR system classification.

The term "LAMP" is a loop-mediated isothermal amplification technique and is a thermostatic nucleic acid amplification technique suitable for gene diagnosis.

The term "PAM" refers to a protospacer-adjacent motif, which is required for Cas12a cleavage. The PAM of FnCas12a is the sequence TTN, the PAM of LbCas12a is the sequence TTTN, and the PAM of AacCas12b is the sequence TTN.

The present invention provides a method for detecting target nucleic acid molecules, which comprises adding a guide RNA, a Cas protein, a nucleic acid probe and a buffer into the reaction system containing the target nucleic acid molecules to be detected, and then detecting the fluorescence intensity thereof.

The Cas protein is Cas12a or Cas12b.

The Cas12a is preferably one of FnCas12a, AsCas12a, LbCas12a, Lb5Cas12a, HkCas12a, OsCas12a, TsCas12a, BbCas12a, BoCas12a or Lb4Cas12a; the Cas12a is preferably LbCas12a.

The Cas12b is preferably AacCas12b, Aac2Cas12b, AkCas12b, AmCas12b, AhCas12b, and AcCas12b.

The guide RNA refers to an RNA that directs the Cas protein to specifically target a DNA sequence.

The target nucleic acid molecules to be detected in the reaction system containing the target nucleic acid molecules to be detected are obtained after amplification.

The detection method detects pathogenic microorganisms, gene mutations or specific target DNA.

The present invention provides a use of a Cas protein in a method for detecting target nucleic acid molecules.

When the target DNA, the guide RNA and the Cas protein form a ternary complex, the complex cleaves other single-stranded DNA molecules in the system.

The guide RNA refers to an RNA that directs the Cas protein to specifically target a DNA sequence.

The invention also provides a kit, comprising a guide RNA, a Cas protein and a nucleic acid probe. Furthermore, the kit of the invention may further comprise a buffer.

The present invention provides a detection method for rapidly detecting target nucleic acid molecules with high specificity. Once the target DNA (single or double stranded), the crRNA, and the Cas12a protein form a ternary complex, the complex cleaves other single-stranded DNA molecules in the system. In the method, the target DNA (a DNA sequence to be detected) is targeted by the designed crRNA; and crRNA and Cas12a protein are added to the detection system. When the target DNA is present, Cas12a, the crRNA and the target DNA form a ternary complex, and the complex cleaves the single-stranded DNA with fluorescent signal label (the fluorescent group and the quenching group are respectively labelled to the two ends, and the fluorescent group can be luminescent after the DNA is cleaved) using its collateral cleavage activity, thereby emitting fluorescence. Therefore, by detecting the fluorescence, it is possible to know whether or not the target DNA molecule is contained in the system to be detected. The method of the present invention allows rapid detection of whether a sample contains a specific DNA sequence. By combining with PCR technology, the sensitivity of the detection method can be greatly improved. The nucleic acid probe in the present invention is preferably a fluorescent probe.

HOLMES Condition Test

The invention provides the application of Cas12 enzyme based on Cas12a, Cas12b and the like in nucleic acid detection. The following describes Cas12a as an example.

Figure 7:
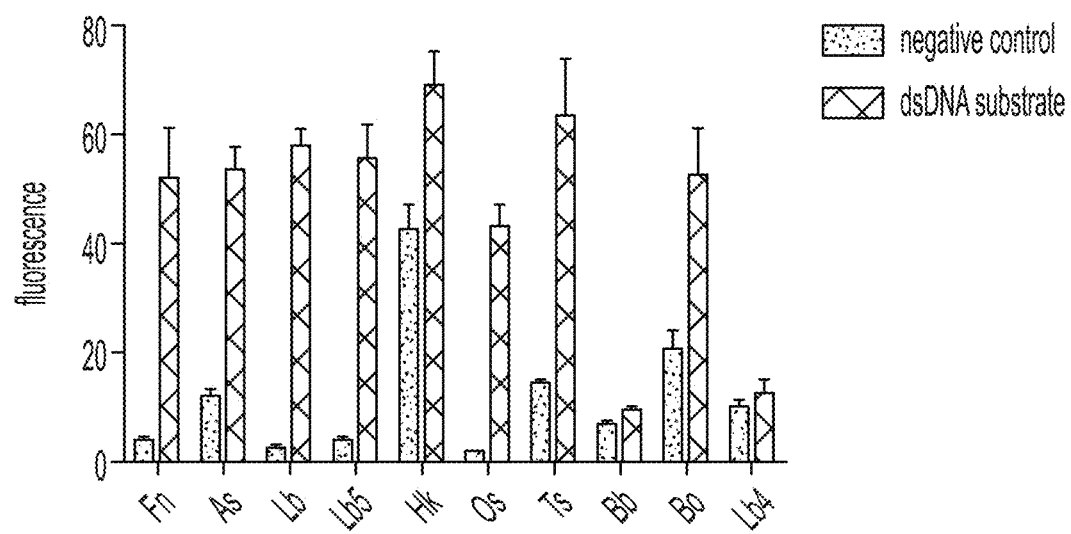
FIG. 7 shows different Cas12a uses specific double-stranded DNA substrates and single-stranded DNA (HEX-N12-BHQ1) as the fluorescent detection probe to obtain the fluorescence value. The negative control group does not add specific substrates. No specific substrate added was employed as the negative control group.

Selection of Cas12a: According to the study, Cas12a has the activity of trans cleavage, ie, once the target DNA, crRNA and Cas12a protein form a ternary complex, other single-stranded DNA (collateral single-stranded DNA) in the system will be cleaved. A specific DNA detection method was designed based on this principle. Firstly, the collateral DNA was designed as a fluorescent probe consisting of a random sequence with a length of 12 nt, and labelled with the fluorescent group HEX at the 5'-terminal end and labelled with the quenching group BHQ1 (HEX-N12-BHQ1) at the 3'-terminal end. When the system contains the target DNA fragment, a ternary complex of the target DNA, crRNA and Cas12a protein will be formed. At this time, the probe is cleaved, and the fluorescence emitted from the HEX fluorescent group can be detected by the fluorescence detector (excitation at 535 nM, and emission at 556 nM). Secondly, 10 different Cas12a were tested, and the target sequence was double-stranded DNA, as shown in FIG. 7. It can be seen that the complex composed of the target double-stranded DNA and each Cas12a protein can achieve trans cleavage activity.

Figure 8:
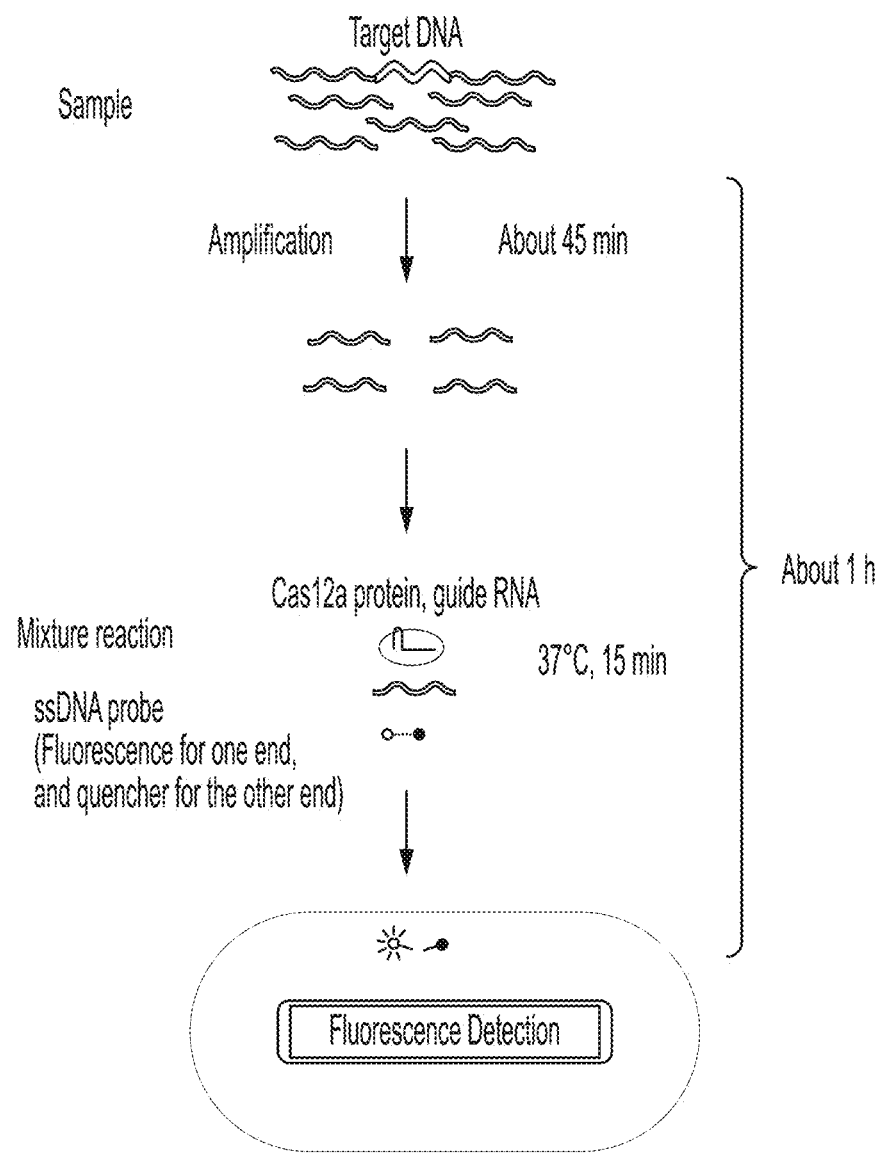
FIG. 8 shows schematic of target DNA detection by the HOLMES method based on target DNA amplification and Cas12a trans-cleavage activity against collateral single-stranded DNA.
Figure 9A:
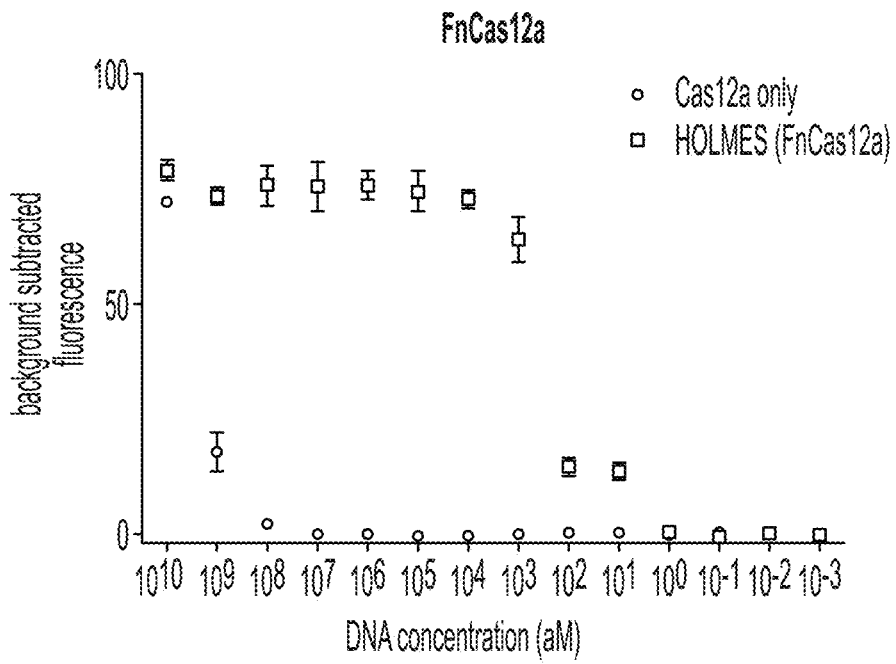
FIG. 9 shows sensitivity test of target DNA by direct use of FnCas12a or LbCas12a, or in combination of the HOLMES method.
Figure 9B:
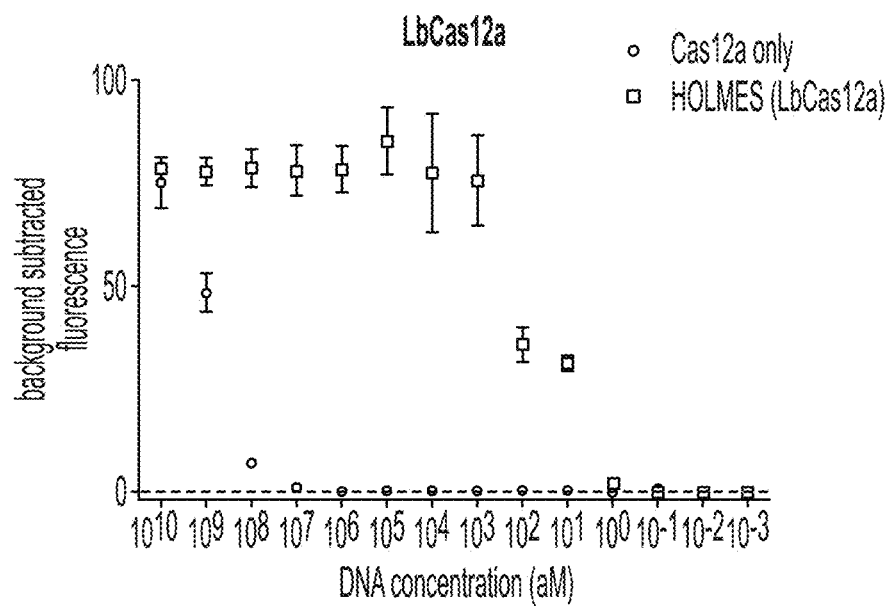

HOLMES Response Sensitivity: Next, the sensitivities of FnCas12a and LbCas12a response to target DNA were tested. That is, the lowest concentration of target DNA that can respond was examined. As shown in FIG. 9, when the test target was directly added, the target DNA with concentration above 0.1 nM was able to respond, and the response was significant at a concentration above 1 nM. If the PCR technique is combined (i.e. HOLMES method), as shown in FIG. 8, i.e. the target fragment is first amplified by PCR and then subjected to Cas12a cleavage reaction, the response sensitivity can be as low as 10 aM, as shown in FIG. 9.

SNP test: Next, whether the HOLMES method can detect the SNP genotype was tested. T1 was used as the target sequence, and mutations were introduced in the PAM or single point mutation was introduced in the target sequence at position of 1-18. And the difference between the non-mutated sequence and the mutant sequences was compared for the crRNAs of different lengths.

Figure 10A:
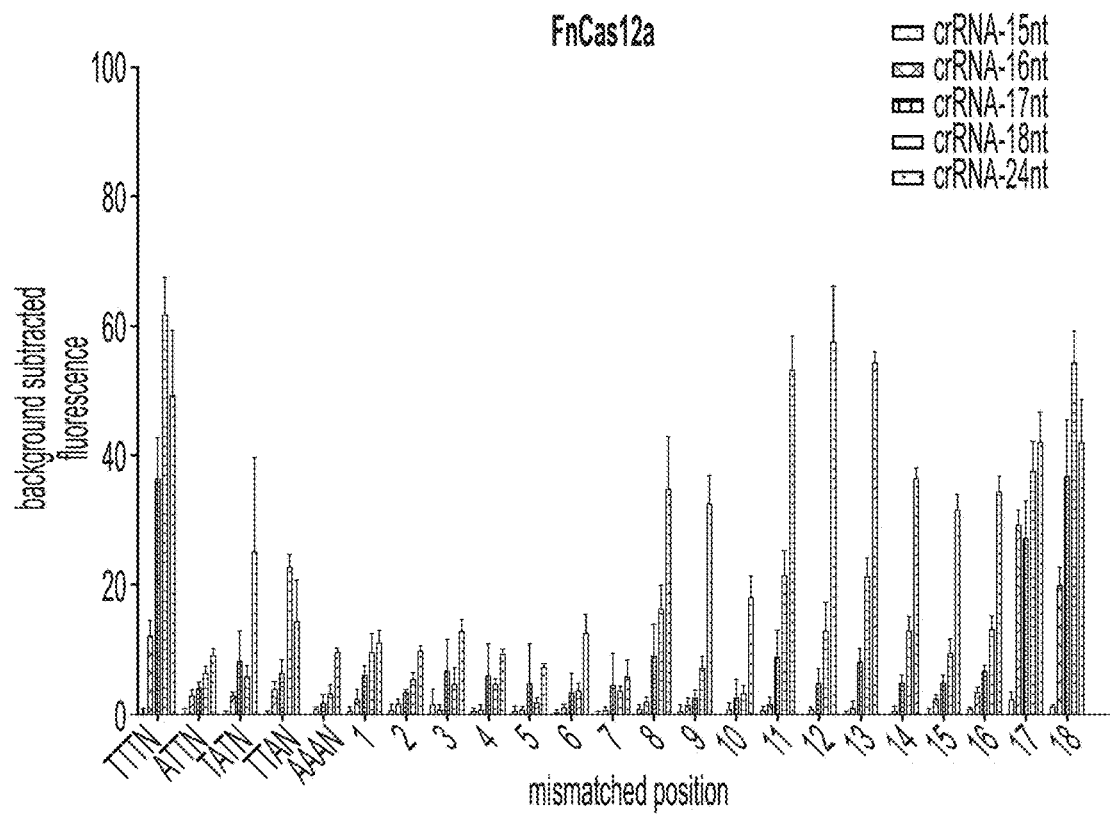
FIG. 10 shows fluorescence detection value of the HOLMES method using crRNAs with different lengths of the guide sequence combined with FnCas12a or LbCas12a on target sequences with different single point mutations.
Figure 10B:
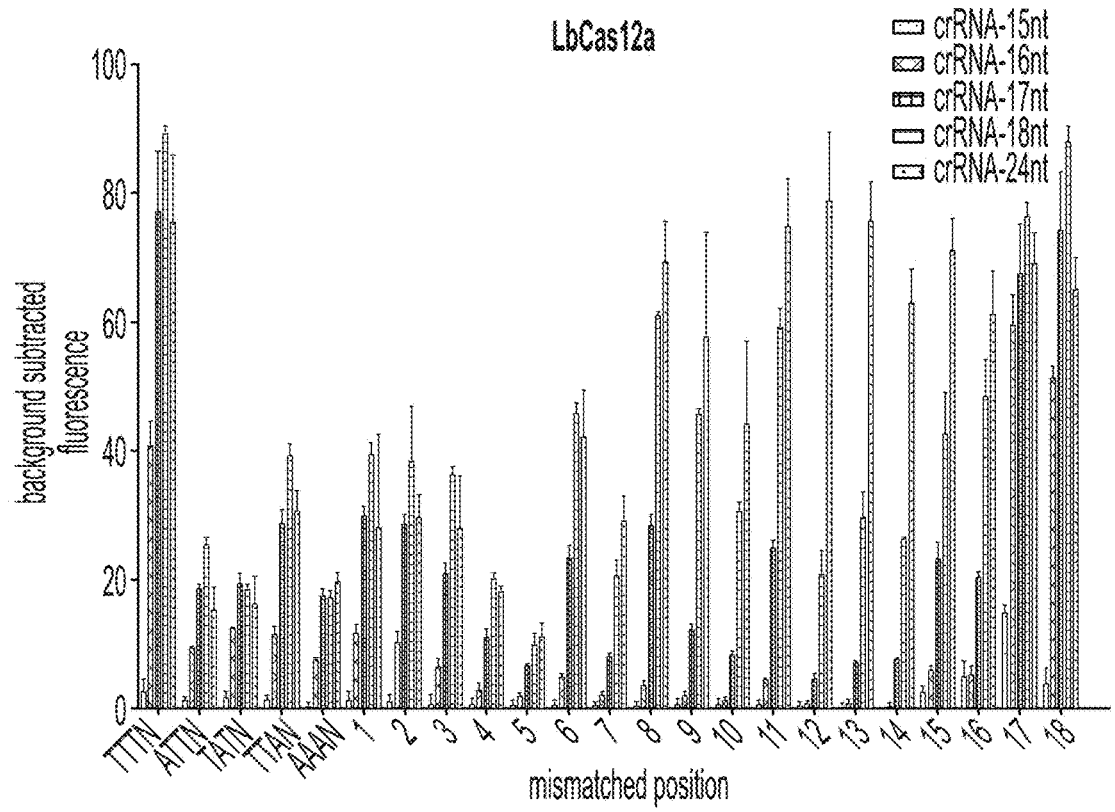

As shown in FIG. 10, when the target complementary sequence is a 24 nt crRNA (crRNA-24 nt), the single point mutations at position of 8-18 are not significantly different from the wild type. When there is any mutation in the PAM and there is any point mutation at position of 1-7, there is a significant drop on the fluorescence value. When the crRNA was truncated and the length of the paired target sequence was 18 nt, the fluorescence value of the target sequence mutated at position 8-16 nt was significantly lower than that of the target sequence with a length of 24 nt. When the length was shortened to 16 nt or 17 nt, the decrease of fluorescence value of the target sequence after mutation was more obvious. When the length was shortened to 15 nt, the fluorescence values of the target sequence and the mutation are weak for the target sequence, but still strong for other target sequences, which can be used for detection. Taken together, 15 nt, 16 nt and 17 nt crRNAs are most suitable for detection of SNPs.

In the present invention, Cas12a cleaves single-stranded DNA. A programmed cleavage mode wherein Cas12a cleaves single-stranded DNA independent of PAM sequence is called cis cleavage; and once a ternary complex Cas12a/crRNA/target DNA is formed, it shows the activity of trans-cleavage, that is, the activity of cleavage of any non-target single-stranded DNA in the system.

Using the characteristics of Cas12a, a method for specifically detecting nucleic acid molecules has been developed, which is called HOLMES (one Hour Low-cost Multipurpose Efficient Simple assay). As the name of the technology, it is characterized as a fast (1 hour), low cost, multi-purpose, efficient, and simple method. The method can be used in the fields of rapid pathogen detection, SNP detection and the like.

Nucleic Acid Detection Based on Collateral Cleavage Activity

The invention also provides a method of nucleic acid detection based on the collateral cleavage activity of a Cas12 enzyme, including Cas12a or Cas12b.

Preferably, the detection of the invention can be performed on SNPs, in particular by PCR amplification followed by detection.

Figure 18:
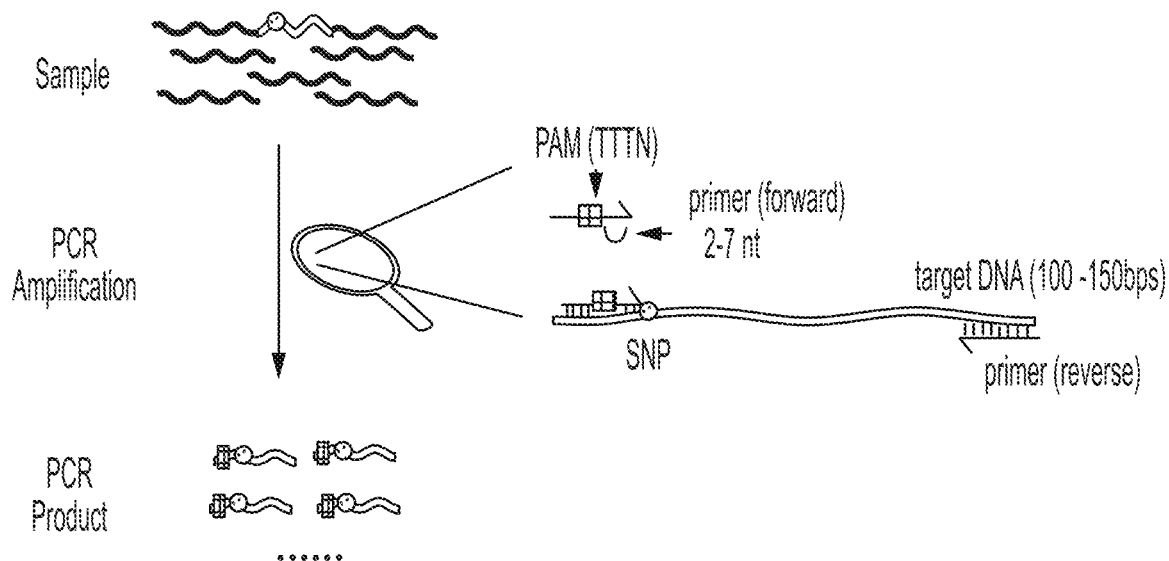
FIG. 18 shows a scheme for primers design in one Example of the present invention, which could be used for HOLMES detection of SNP in any site.

Referring to FIG. 18, the design of the primers is given.

Case 1. When there is a PAM site near the SNP site, the synthesized crRNA based on the guide sequence designed according to the PAM site can be used for HOLMES detection. When the HOLMES method is used for detection, the background signal is relatively low; for the same guide sequence, the signal difference between different SNP templates is relatively large.

Case 2. When there is no PAM site near the SNP site, or there is no suitable PAM site, the introduction of the PAM site can be performed according to the above experimental protocol.

A typical procedure comprises designing a primer near the SNP site, carrying a PAM site on the primer, and the 3' end sequence at the PAM site needs to be paired with the template DNA. There is no special requirements for the primer at the other end, and it only needs to be paired with the template DNA and can be subjected to PCR amplification. As shown in FIG. 18, the PAM site was successfully introduced after PCR amplification.

Referring to FIG. 10, in the present invention, when designing for the introduction of a PAM, usually the SNP site is located at the position of the first 16 bases of from 5' end of the crRNA guide sequence, preferably 1-14, more preferably 1-12, more preferably 1-11 or 1-10, and most preferably 1-8 or 1-7.

The main advantages of the invention are:
(1) Fast: When the test conditions are ready, it takes only about 1 hour from getting the sample to getting the test result.
(2) Low cost: There are no special materials or enzymes required in the experiment, and the amount of materials and reagents involved is small. It can be used for testing and analysis of trace amounts.
(3) Efficient: The method of the present invention has extremely high sensitivity and can detect DNA at a concentration of 10 aM.
(4) Multi-purpose: It can detect different nucleic acid samples, including DNA samples and RNA samples.
(5) Simple: There are no special complicated steps. If the kit is ready and the program is set, only the steps of simply adding the sample and the like are needed.

The invention is further illustrated below in conjunction with specific Examples. It should be understood that the Examples are provided to illustrate the present invention, but are not intended to limit the scope of the invention. The experimental methods in the following Examples which do not specify the specific conditions are usually in accordance with conventional conditions, such as conditions described in Sambrook et al., Molecular Cloning: Laboratory Manual (New York: Cold Spring Harbor Laboratory Press, 1989), or in accordance with the conditions recommended by the manufacturer. Unless otherwise stated, percentages and parts are by weight.

The experimental materials involved in the present invention can be obtained commercially unless otherwise specified.

Materials

1. The RNase inhibitor was purchased from TaKaRa. The high-fidelity DNA polymerase KOD FX was purchased from ToYoBo. The primers (oligonucleotides) were synthesized by Shanghai Sangon Biotech. The T7 RNA polymerase was purchased from Thermo. The RNA purification and concentration kit (RNA Clean & Concentrator™-5) was purchased from Zymo Research. Wizard® SV Gel and PCR Clean-Up System was purchased from Promega. The media (e.g. Tryptone, Yeast Extract, etc.) were purchased from OXOID.

2. Medium formula: liquid LB (1% Tryptone, 0.5% Yeast extract, 1% NaCl). When formulating solid LB, only 2% agar should be added to the liquid LB.

Example 1. Detection of Detectable Single-Stranded DNA Target by Cas12a Proteins (FAM-Labelled Probe)

Single-stranded DNA (target-T1-R) was used as the target sequence to test the response values of different Cas12a proteins for detection thereof.

1. Preparation of crRNA: First, T7-crRNA-F and synthetic oligonucleotides of T7-T1-24-R, as shown in table 5, were annealed to prepare the template for transcription. Specifically, 4 µM of paired oligonucleotides were annealed in 1×PCR buffer (Transgen. Biotech.) with a volume of 50-µL, following the annealing program: initial denaturation at 95° C. for 5 min, then cooling down from 95° C. to 20° C. using thermocycler (decrease by 1° C. per min). crRNA was synthesized using T7 high-yield transcription kit, and the reaction was performed at 37° C. overnight (about 16 h). Then, RNA is purified using RNA purification and concentration kits, quantitated with NanoDrop 2000C (Thermo Fisher Scientific), diluted to a concentration of 10 µM and stored at −80° C. in a refrigerator.

2. Cas12a reaction: In a 20-µL reaction system was added with 0.5 µM crRNA purified from step 1, 0.25 µM Cas12a, 0.01 µM target single-stranded DNA (target-T1-R), 0.01 µM nucleic acid probe (N25-5' FAM), NEB buffer 3.1, and 0.5 µL of RNA enzyme inhibitor. For blank control reaction, all other components were added except single-stranded DNA target sequence. The reaction was carried out at 37° C. for 15 min, and then stopped at 98° C. for 2 min.

Figure 11A:
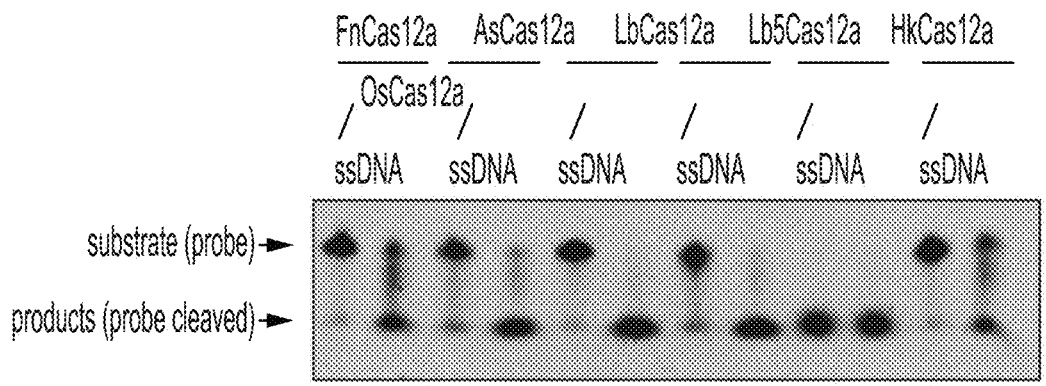
FIG. 11 shows using FAM-labeled fluorescent probes, 10 Cas12a proteins were selected to test whether the FAM-labeled single-stranded DNA probe is trans-cleaved after adding the target single-stranded DNA.
Figure 11B:
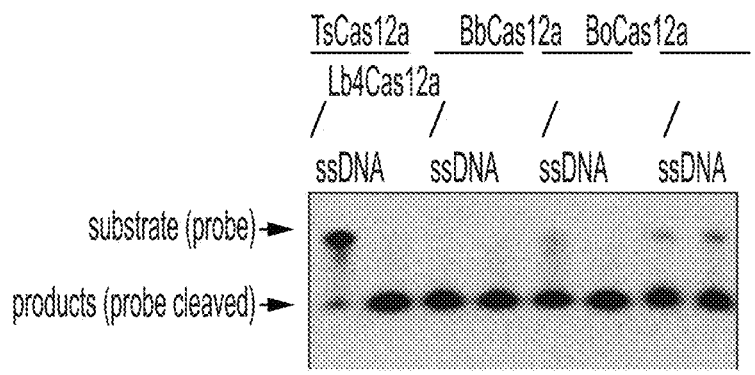

3. Fluorescence detection: Electrophoresis was carried out with urea-polyacrylamide gel electrophoresis (Urea-PAGE) and then detection was carried out with the fluorescence luminescence imager. As shown in FIG. 11, different Cas12as showed distinct target defection effects. For example, HkCas12a and the like cleaved the probe even without target single-stranded DNA being added. However, LbCas12a and the like cleaved the probe only with target single-stranded DNA being added, and were good Cas12a protein candidates.

Example 2. Detection of Detectable Single-Stranded DNA Target by Cas12a Proteins (Dural HEX & BHQ1-Labelled Probes)

Single-stranded DNA (target-T1-R) was used as the target sequence to test the response values of different Cas proteins for detection thereof.

1. Preparation of crRNA: First, T7-crRNA-F and synthetic oligonucleotides of T7-T1-24-R (Table 5) were annealed and used to prepare the template for transcription. Specifically, 4 µM of paired oligonucleotides were annealed in 1×PCR buffer (Transgen Biotech) with a volume of 50-µL, following the annealing procedure: initial denaturation at 95° C. for 5 min, and then cooling down from 95° C. to 20° C. using thermocycler (decrease by 1° C. per min). crRNA was synthesized using T7 high-yield transcription kit, and the reaction was performed at 37° C. overnight (about 16 h). Then, RNA was purified with an RNA purification and concentration kit, quantitated with NanoDrop 2000C, diluted to a concentration of 10 µM and stored at −80° C. in a refrigerator.

2. Cas12a reaction: In a 20-µL reaction system was added with 0.5 µM crRNA purified from step 1, 0.25 µM Cas12a, 0.01 µM target single-stranded DNA (target-T1-R), 0.5 µM fluorescent probe (HEX-N12-BHQ1. i.e. 12 nt single-stranded DNA labelled with HEX at the 5' end and BHQ1 at the 3' end), NEB buffer 3.1, and 0.5 µL of RNA enzyme inhibitor. For control reaction, all other components were added except single-stranded DNA target sequence. The reaction was carried out at 37° C. for 15 min, and then stopped at 98° C. for 2 min.

Figure 12:
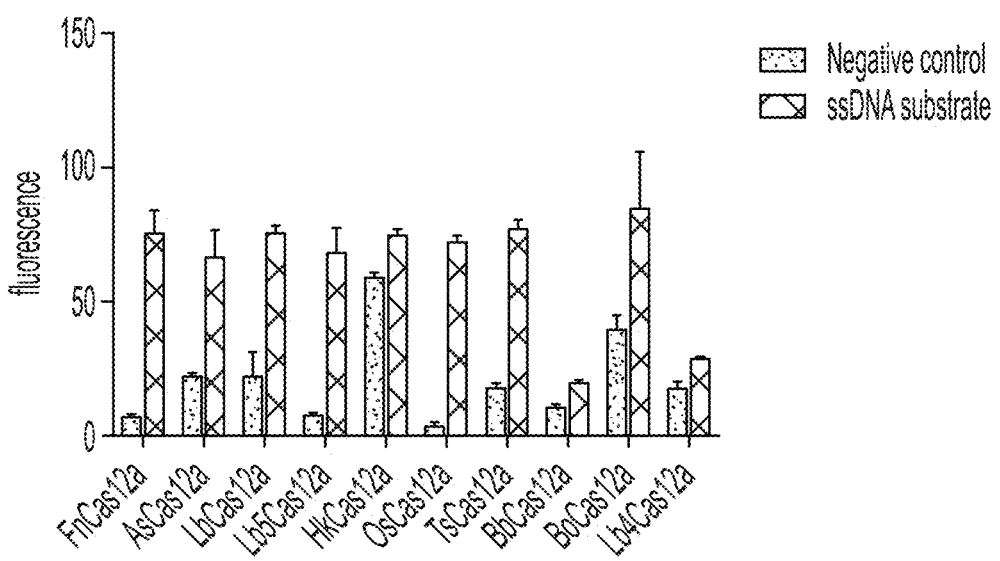
FIG. 12 shows using HEX-N12-BHQ1 as a probe, 10 Cas12a proteins were selected to test the fluorescence value after adding the target single-stranded DNA.

3. Fluorescence detection: 20 µL, of inactivated reaction liquid was added into the 96-well plate and then detected with a microplate reader with the excitation at 535 nm and emission at 556 nm. As shown in FIG. 12, different Cas12as showed distinct target defection effects. For example, HkCas12a and the like cleaved the probe even without target single-stranded DNA being added. However, FnCas12a and the like cleaved the probe only with target single-stranded DNA being added, and were good Cas12a protein candidates.

Example 3. Detection of Detectable Double-Stranded DNA Target by Cas12a Proteins Double-stranded DNA (target-T1) was used as the target sequence to test the response values of different Cas proteins for detection thereof.

1. Preparation of crRNA: First, T7-crRNA-F and synthetic oligonucleotides of T7-T1-24-R (Table 5) were annealed to prepare the template for transcription. Specifically, 4 µM of paired oligonucleotides were annealed in 1×PCR buffer (Transgen Biotech) with a volume of 50-µL, following the annealing procedure: initial denaturation at 95° C. for 5 min, and then cooling down from 95° C. to 20° C. using thermocycler (decrease by 1° C. per min). crRNA was synthesized using T7 high-yield transcription kit, and the reaction was performed at 37° C. overnight (about 16 h). Then, RNA was purified with an RNA purification and concentration kit, quantitated with NanoDrop 2000C, diluted to a concentration of 10 µM and stored at −80° C. in a refrigerator.

2. Cas12a reaction: In a 20-µL reaction system was added with 0.5 µM crRNA purified from step 1, 0.25 µM Cas12a, 0.01 µM target double-stranded DNA (target-T1, obtained from annealing of primer target-T1-F and primer target-T1-R), 0.5 µM fluorescent probe (HEX-N12-BHQ1), NEB buffer 3.1, and 0.5 µL of RNA enzyme inhibitor. The reaction was carried out at 37° C. for 15 min, and then stopped at 98° C. for 2 min.

3. Fluorescence detection: 20 µL, of inactivated reaction liquid was added into the 96-well plate and then detected with a microplate reader with the excitation at 535 nm and emission at 556 nm. As shown in FIG. 7, different Cas12as showed distinct target defection effects. Whereas LbCas12a and the like cleaved the probe only with target double-stranded DNA being added, and were good Cas12a protein candidates.

Example 4. Testing of Targets at Different Concentrations by FnCas12a and LbCas12a Target-T1 DNA was used as target DNA, then subjected to gradient dilution into different concentrations to test the sensitivity of FnCas12a or LbCas12a response to it. To enhance the sensitivity, PCR amplification step was added.

1. Preparation of crRNA: First, T7-crRNA-F and synthetic oligonucleotides of T7-T1-24-R (Table 5) were annealed to prepare the template for transcription. Specifically, 4 µM of paired oligonucleotides were annealed in 1×PCR buffer (Transgen Biotech) with a volume of 50-µL, following the annealing procedure: initial denaturation at 95° C. for 5 min, and then cooling down from 95° C. to 20° C. using thermocycler (decrease by 1° C. per min). crRNA was synthesized using T7 high-yield transcription kit, and the reaction was performed at 37° C. overnight (about 16 h). The RNA was purified with an RNA purification and concentration kit, quantitated with NanoDrop 2000C, diluted to a concentration of 10 µM and stored at −80° C. in a refrigerator.

2. PCR amplification (optional): Plasmid (pUC18-T1) that contained the target-T1 target, as the template, was subjected to gradient dilution and PCR reaction. The total volume of each reaction system was 20 μL, 0.25 μM of primers of M13F-47 and M13R-48 ware used (Table 4), and high-fidelity enzyme KOD FX (ToYoBo) was used for PCR reaction. The PCR reaction procedure was at 95° C. for 2 min, followed by 35 cycles of 98° C. for 10 s, 60° C. for 15 s and 68° C. for 10 s. After PCR was completed, the PCR purification products were directly used for Cas12a reaction.

3. Cas12a reaction: In a 20-μL reaction system was added with 0.5 μM crRNA purified from step 1, 0.25 μM FnCas12a or LbCas12a, 1 μL of PCR products (or target DNA directly diluted to different concentrations), 0.5 μM fluorescent probe (HEX-N12-BHQ1), NEB buffer 3.1, and 0.5 μL of RNA enzyme inhibitor. The reaction was carried out at 37° C. for 15 min, and then stopped at 98° C. for 2 min.

4. Fluorescence detection: 20 μL of inactivated reaction liquid was added into the 96-well plate and then detected with a microplate reader with the excitation at 535 nm and emission at 556 nm. As shown in FIG. 9, target DNA at or above 0.1 nM was able to response when the test targets were directly added, and response was significant when the concentration was above 1 nM. However, combined with PCR technology, i.e., first PCR amplification of fragments of interest and then Cas12a cleavage reaction, the response sensitivity could be as low as 10 aM.

Example 5. Testing of Single-Point Mutation Target by FnCas12a and LbCas12a

Target-T1 DNA was used as the target and mutated in the PAM region and position 1-18, respectively. Several crRNAs of different lengths were tested for response values to the wild type and single-point mutated targets.

1. Preparation of crRNA: First, T7-crRNA-F was annealed with synthetic oligonucleotides of T7-T1-24-R, T7-T1-15-R, T7-T1-16-R, T7-T1-17-R and T7-T1-18-R (Table 5), respectively, to prepare templates for transcription. Specifically, 4 μM of paired oligonucleotides were annealed in 1×PCR buffer (Transgen Biotech) with a volume of 50-μL, following the annealing procedure: initial denaturation at 95° C. for 5 min, and then cooling down from 95° C. to 20° C. using thermocycler (decrease by 1° C. per min). crRNA was synthesized using T7 high-yield transcription kit, and the reaction was performed at 37° C. overnight (about 16 h). The RNA was purified with an RNA purification and concentration kit, quantitated with NanoDrop 2000C, diluted to a concentration of 10 μM and stored at −80° C. in a refrigerator.

2. PCR amplification: Plasmid (pUC18-T1) that contained the target-T1 target was used as the template. The total volume of each reaction system was 20 μL, 0.25 μM primers of M13R-48 and each mutant primer for Target-T1-F were used (Table 4), and high-fidelity enzyme KOD FX (ToYoBo) was used for PCR reaction. The PCR reaction procedure was at 95° C. for 2 min, followed by 35 cycles of 98° C. for 10 s, 60° C. for 15 s and 68° C. for 10 s. After PCR was completed, they were directly used for Cas12a reaction.

3. Cas12a reaction: In a 20-μL reaction system was added with 0.5 μM crRNA purified from step 1, 0.25 μM FnCas12a or LbCas12a, 1 μL of PCR products, 0.5 μM fluorescent probe (HEX-N12-BHQ1), NEB buffer 3.1, and 0.5 μL of RNA enzyme inhibitor. The reaction was carried out at 37° C. for 15 min, and then stopped at 98° C. for 2 min.

4. Fluorescence detection: 20 μL of inactivated reaction liquid was added into the 96-well plate and then detected with a microplate reader with the excitation at 535 nm and emission at 556 nm. As shown in FIG. 10, when the target complementary sequence was 24 nt crRNA (crRNA-24 nt), no significant difference was observed between single-point mutated target with mutation at position 8-18 and the wild type, and after mutation within PAM and at position 1-7, the fluorescence value was obviously decreased. When crRNAs were truncated and the paired target sequence length was 18 nt, the fluorescence value of the mutation at position 8-16 nt was remarkably lower than that at 24 nt. At 16 nt or 17 nt, the fluorescence value of the mutated target sequence was decreased more remarkably. At 15 nt, the fluorescence value of both the target sequences and the mutants was very weak. However, the strength thereof could be still high for other target sequences, which could be used for detection. To sum up, crRNAs of 15 nt, 16 nt and 17 nt were the most suitable for detection of SNP.

Example 6. Testing of Microorganisms Such as *E. coli* in Environmental Water

The *E. coli* gyrB gene was selected as the detection target to indirectly test the concentration of microorganisms such as *E. coli* in the water. *E. coli* MG1655 was used as the positive control to determine the content of microorganisms in the environmental water such as polluted water and running water.

1. Preparation of crRNA: First, T7-crRNA-F and synthetic oligonucleotides of T7-crRNA-gyrB (Table 5) were annealed to prepare the template for transcription. Specifically, 4 μM of paired oligonucleotides were annealed in 1×PCR buffer (Transgen Biotech) with a volume of 50-μL, following the annealing procedure: initial denaturation at 95° C. for 5 min, and then cooling down from 95° C. to 20° C. using thermocycler (decrease by 1° C. per min). crRNA was synthesized using T7 high-yield transcription kit, and the reaction was performed at 37° C. overnight (about 16 h). The RNA was purified with an RNA purification and concentration kit, quantitated with NanoDrop 2000C, diluted to a concentration of 10 μM and stored at −80° C. in a refrigerator.

2. PCR amplification: The positive control sample was *E. coli* MG1655 which was cultured till the $OD_{600}$ reached about 0.5, then subjected to 10 times gradient dilution and used as the template. Samples were taken from environmental water, including running water and environmental mud water. The total volume of each reaction system was 20 μL, 0.25 μM primers of gyrB-F and gyrB-R were used (Table 4), and high-fidelity enzyme KOD FX (ToYoBo) was used for PCR reaction. The PCR reaction procedure was at 95° C. for 2 min, followed by 35 cycles of 98° C. for 10 s, 60° C. for 15 s and 68° C. for 10 s. After PCR amplification, the PCR products were directly used for Cas12a reaction.

3. Cas12a reaction: In a 20-μL reaction system was added with 0.5 μM crRNA purified from step 1, 0.25 μM LbCas12a, 1 μL of PCR products, 0.5 μM fluorescent probe (HEX-N12-BHQ1), NEB buffer 3.1, and 0.5 μL of RNA enzyme inhibitor. The reaction was carried out at 37° C. for 15 min, and then stopped at 98° C. for 2 min.

Figure 13A:
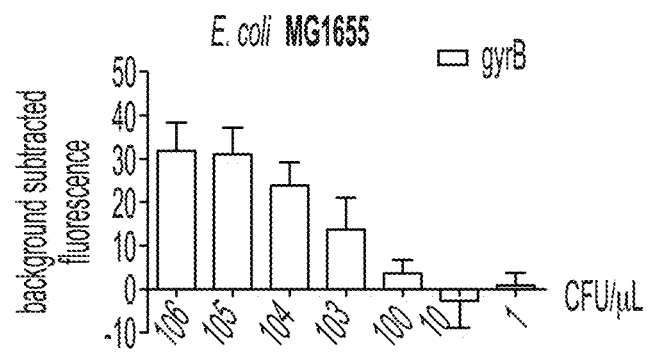
FIG. 13. (A) Single-stranded DNA fluorescent probes labeled with HEX and BHQ1 at both ends show HOLMES detection values using the gyrB gene fragment as the target sequence and different concentrations of pure cultured *E. coli* MG1655 as the positive control template. It is shown that as the concentration of *E. coli* MG1655 decreases, its fluorescence response value gradually decreases. (B) Detection values of environmental water samples in different locations.
Figure 13B:
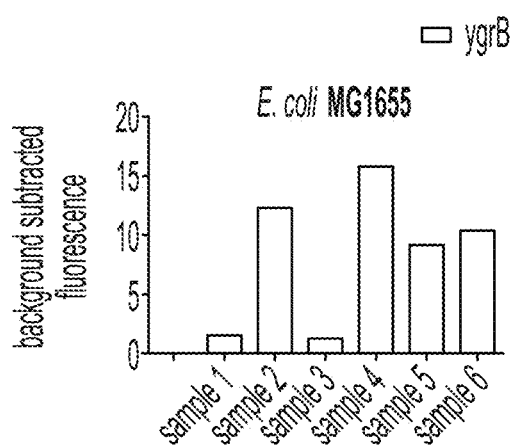
Figure 14A:
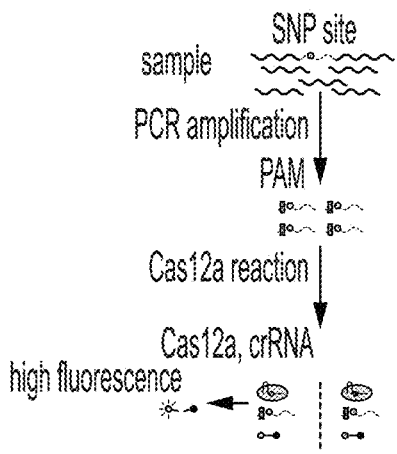
FIG. 14 shows schematic diagram of the HOLMES method for detecting SNPs, and the fluorescence detection values of 5 SNP sites.
Figure 14B:
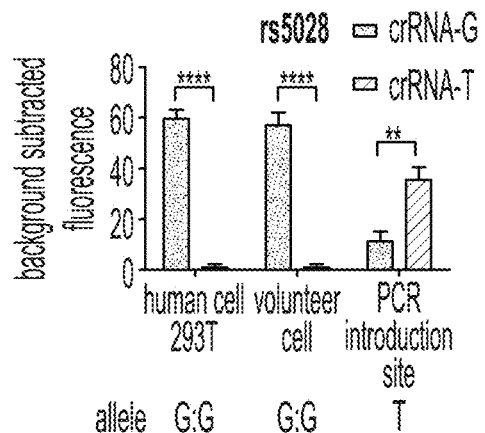
Figure 14C:
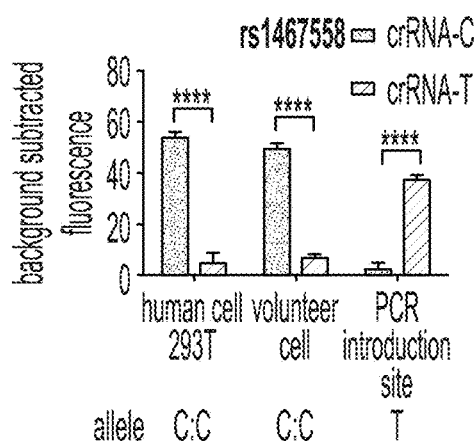
Figure 14D:
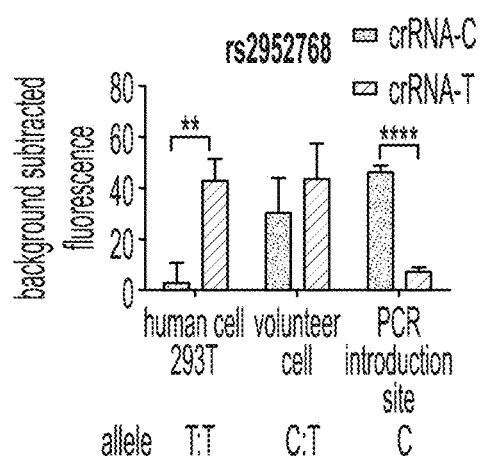
Figure 14E:
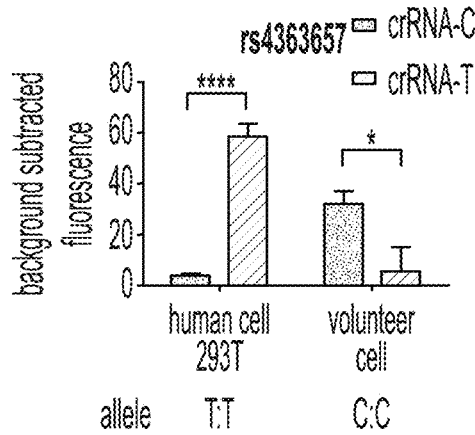
Figure 14F:
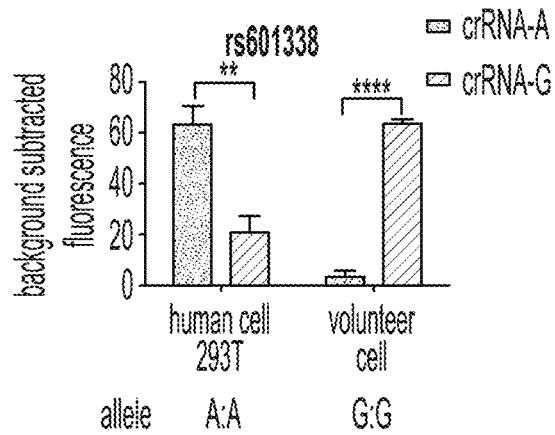

4. Fluorescence detection: 20 μL of inactivated reaction liquid was added into the 96-well plate and then detected with a microplate reader with the excitation at 535 nm and emission at 556 nm. As shown in FIG. 13, the fluorescence response values were gradually lowered with the decrease of the concentration of E. coli MG1655. Among these, microorganisms were obviously detected in samples 2, 4, 5 and 6.

Example 7. Testing of Human SNP

Five sites of human SNP were selected for SNP testing, including rs5082, rs1467558, rs2952768, rs4363657 and rs601338, to test the feasibility of the HOLMES method.

1. Preparation of crRNA: First, T7-crRNA-F and synthetic oligonucleotides (Table 5) were annealed to prepare the template for transcription. Specifically, 4 µM of paired oligonucleotides were annealed in 1×PCR buffer (Transgen Biotech) with a volume of 50-µL, following the annealing procedure: initial denaturation at 95° C. for 5 min, and then cooling down from 95° C. to 20° C. using thermocycler (decrease by 1° C. per min). crRNA was synthesized using T7 high-yield transcription kit, and the reaction was performed at 37° C. overnight (about 16 h). The RNA was purified with RNA Clean & Concentrator™-5 (Zymo Research), quantitated with NanoDrop 2000C, diluted to a concentration of 10 µM and stored at −80° C. in a refrigerator.

2. PCR amplification: The total volume of reaction system was 20 µL, 0.25 µM primers were used (Table 4), 1 ng of human genome (HEK293T) or directly scraped oral mucous epithelium was used as the template, and the high-fidelity polymerase KOD FX (ToYoBo) was used for PCR reaction. The PCR reaction procedure was at 95° C. for 2 min, followed by 35 cycles of 98° C. for 10 s, 60° C. for 15 s and 68° C. for 10 s. After PCR was completed, they were directly used for Cas12a reaction (Primers, such as 1-rs5082-F-T, 2-rs1467558-F-T and 3-rs2952768-R-C were directly introduced into respective mutated products of SNP).

3. Cas12a reaction: In a 20-µL reaction system was added with 1 µM respective crRNA, 0.5 LbCas12a, 1 µL of PCR products, and 0.5 µM fluorescent probe (HEX-N12-BHQ1). The reaction was carried out at 37° C. for 15 min, and then stopped at 98° C. for 2 min.

4. Fluorescence detection: 20 µL of inactivated reaction liquid was added into the 96-well plate and then detected with a microplate reader with the excitation at 535 nm and emission at 556 nm. As shown in FIG. 14, only with the crRNA corresponding to respective target sequences, higher fluorescence response values were generated, and if one-point mutation occurred, the response value thereof would be largely reduced. The corresponding SNP genotype could be determined based on the fluorescence value, and these results were confirmed by sequencing results.

Example 8. Testing of Cancer-Related Genes

TP53 gene was selected for testing gene. TP53 gene contains a nonsense mutation in human T24 cells, which results in the inactivation of this gene. Cells with gene at this site being normal (HEK293T), individual gene and mutated cell T24 were tested.

1. Preparation of crRNA: First, T7-crRNA-F was annealed with synthetic oligonucleotides of T7-crRNA-34-TP53-T24-C-16 nt and T7-crRNA-34-TP53-T24-G-16 nt (Table 5) to prepare the template for transcription. Specifically, 4 µM of paired oligonucleotides were annealed in 1×PCR buffer (Transgen Biotech) with a volume of 50-µL, following the annealing procedure: initial denaturation at 95° C. for 5 min, and then cooling down from 95° C. to 20° C. using thermocycler (decrease by 1° C. per min). The crRNA was synthesized using T7 high-yield transcription kit, and the reaction was performed at 37° C. overnight (about 16 h). The RNA was purified with RNA Clean & Concentrator™-5 (Zymo Research), quantitated with NanoDrop 2000C, diluted to a concentration of 10 µM and stored at −80° C. in a refrigerator.

2. PCR amplification: The total volume of reaction system was 20 µL, 0.25 µM primers of 34-TP53-T24-F and 34-TP53-T24-R were used (Table 4), 1 ng of human genome (HEK293T, T24) or directly scraped oral mucous epithelium was used as the template, and the high-fidelity polymerase KOD FX (ToYoBo) was used for PCR reaction. The PCR reaction procedure was at 95° C. for 2 min, followed by 35 cycles of 98° C. for 10 s, 60° C. for 15 s and 68° C. for 10 s. After PCR was completed, they were directly used for Cas12a reaction.

3. Cas12a reaction: In a 20-µL reaction system was added with 1 µM respective crRNA, 0.5 µM LbCas12a, 1 µL of PCR products, and 0.5 µM fluorescent probe (HEX-N12-BHQ1). The reaction was carried out at 37° C. for 15 min, and then stopped at 98° C. for 2 min.

Figure 15:
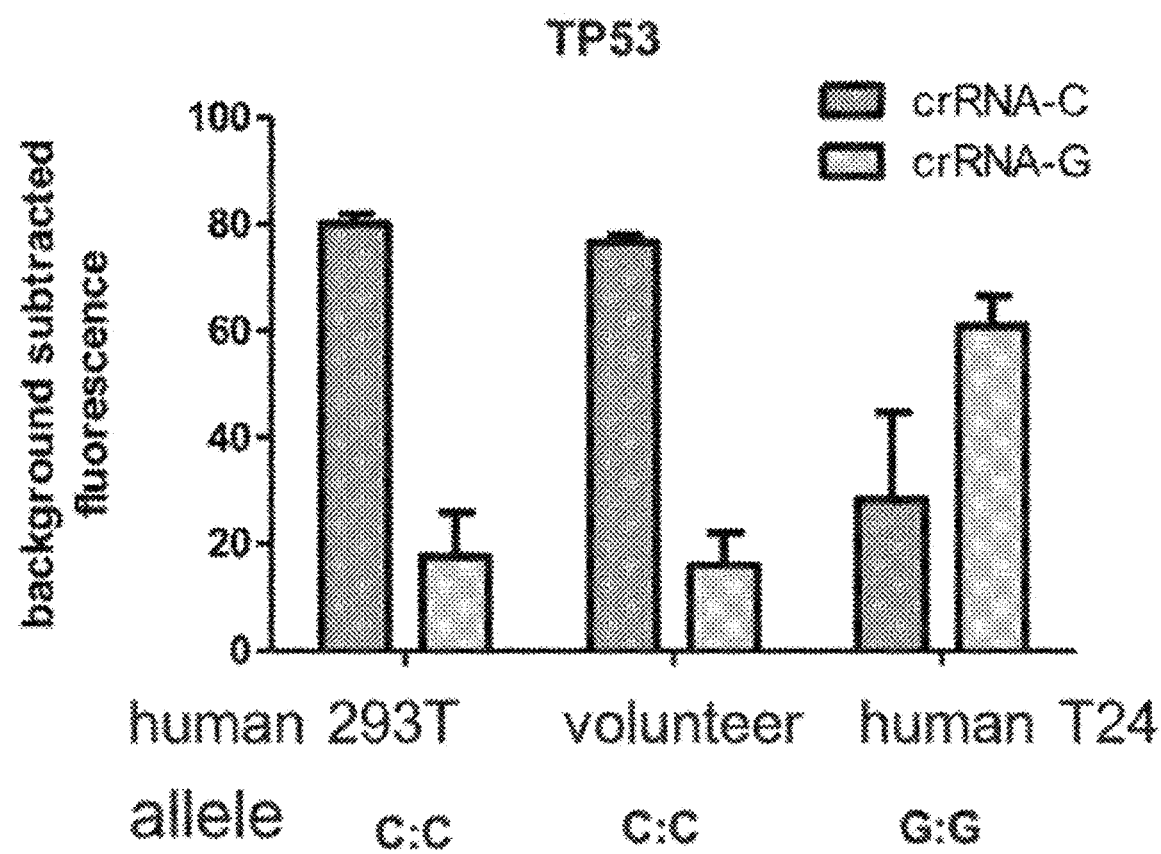
FIG. 15 shows the fluorescence detection values in key sites when using HOLMES method for detecting TP53 gene (a cancer-related gene).
Figure 16A:
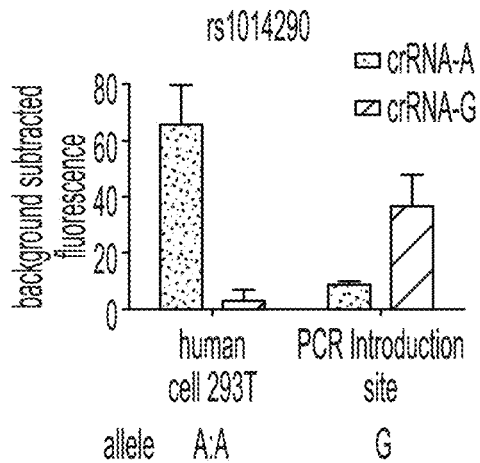
FIG. 16 shows the detection values of 5 SNP sites (gout related) by using HOLMES method.
Figure 16B:
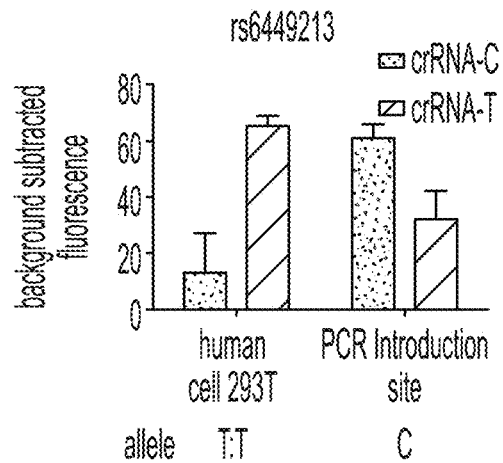
Figure 16C:
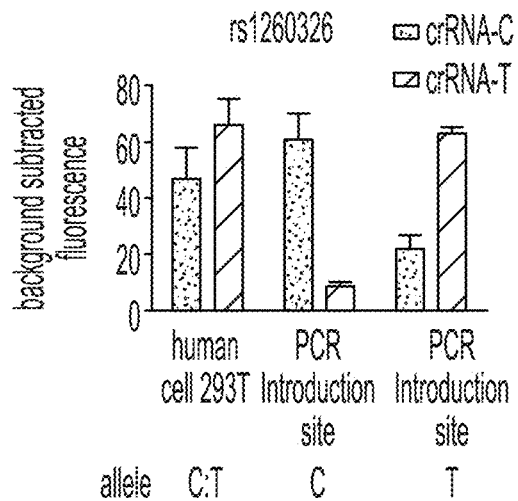
Figure 16D:
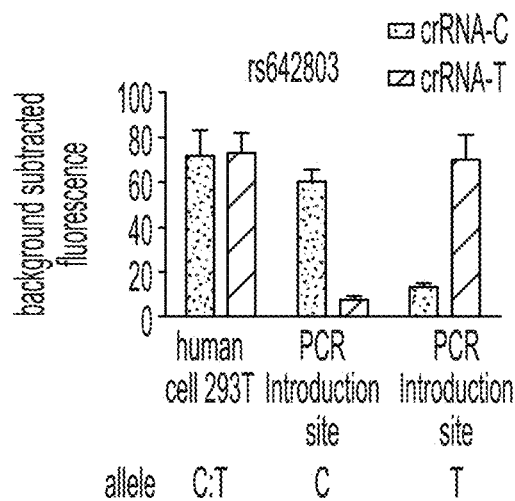
Figure 16E:
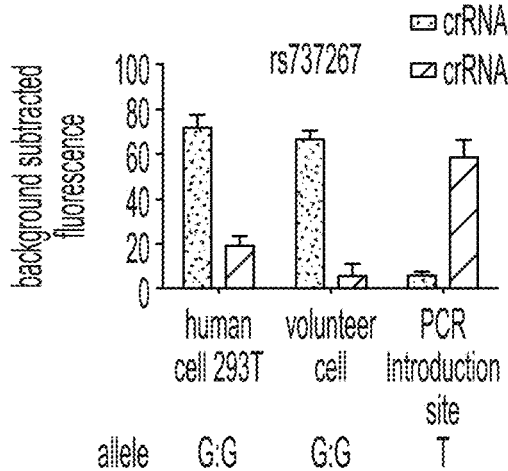

4. Fluorescence detection: 20 µL of inactivated reaction liquid was added into the 96-well plate and then detected with a microplate reader with the excitation at 535 nm and emission at 556 nm. As shown in FIG. 15, when value of crRNA-C detected by using TP53 gene being normal at this site as the template was obviously higher than that of crRNA-G, crRNA-G of the mutated cell T24 was obviously increased.

Example 9. Testing of Human SNPs (Gout Related Genes)

Five sites of human SNP were selected for SNP testing, which are related to risk of gout, including rs1014290, rs6449213, rs737267, rs1260326 and rs642803, to test the HOLMES method.

1. Preparation of crRNA: First, T7-crRNA-F and synthetic oligonucleotides (Table 5) were annealed to prepare the template for transcription. Specifically, 4 µM of paired oligonucleotides were annealed in 1×PCR buffer (Transgen Biotech) with a volume of 50-µL, following the annealing procedure: initial denaturation at 95° C. for 5 min, and then cooling down from 95° C. to 20° C. using thermocycler (decrease by 1° C. per min). crRNA was synthesized using T7 high-yield transcription kit, and the reaction was performed at 37° C. overnight (about 16 h). The RNA was purified with RNA Clean & Concentrator™-5 (Zymo Research), quantitated with NanoDrop 2000C, diluted to a concentration of 10 µM and stored at −80° C. in a refrigerator.

2. PCR amplification: The total volume of reaction system was 20 µL, 0.25 µM primers were used (Table 4), 1 ng of human genome (HEK293T) or directly scraped oral mucous epithelium was used as the template, and the high-fidelity polymerase KOD FX (ToYoBo) was used for PCR reaction. The PCR reaction procedure was at 95° C. for 2 min, followed by 35 cycles of 98° C. for 10 s, 60° C. for 15 s and 68° C. for 10 s. After PCR was completed, they were directly used for Cas12a reaction. (Primers, such as 1-rs5082-F-T, 2-rs1467558-F-T and 3-rs2952768-R-C were directly introduced into respective mutated products of SNP).

3. Cas12a reaction: In a 20-µL reaction system was added with 1 µM respective crRNA, 0.5 µM LbCas12a, 1 µL of PCR products, and 0.5 µM fluorescent probe (HEX-N12-BHQ1). The reaction was carried out at 37° C. for 15 min, and then stopped at 98° C. for 2 min.

4. Fluorescence detection: 20 µL of inactivated reaction liquid was added into the 96-well plate and then detected with a microplate reader with the excitation at 535 nm and emission at 556 nm. As shown in FIG. 16, only with the crRNA corresponding to respective target sequences, higher fluorescence response values were generated, and if one-point mutation occurred, the response value would be largely reduced. The corresponding SNP genotype could be determined based on the fluorescence value, and the these results were confirmed by sequencing results.

Example 10. Testing of the Volunteers' Clinic Samples with Kit SNPs (Gout Related Genes)

Premix was added into the 96-well plate to make a kit, then the genomic DNA of 21 volunteers was added to test the rs1014290 site, which is related to gout risk.

1. Preparation of kit: First, T7-crRNA-F and synthetic oligonucleotides (Table 5) were annealed to prepare the template for transcription. Specifically, 4 µM of paired oligonucleotides were annealed in 1×PCR buffer (Transgen Biotech) with a volume of 50-µL, following the annealing procedure: initial denaturation at 95° C. for 5 min, and then cooling down from 95° C. to 20° C. using thermocycler (decrease by 1° C. per min). crRNA was synthetized using T7 high-yield transcription kit, and the reaction was performed at 37° C. overnight (about 16 h). The RNA was purified with RNA Clean & Concentrator™-5 RNA (Zymo Research), quantitated with NanoDrop 2000C, and diluted to a concentration of 10 µM.

2. Premix of PCR reagents in the 96-well plate: Reagents required for PCR were added into the 19-µL system, using primers of 41-rs1014290-F and 41-rs1014290-R.

3. Premix in the 96-well plate for fluorescence detection: 1 µM crRNA, 0.5 µM LbCas12a was added into the 19-µL system and 0.5 µM fluorescent probe (HEX-N12-BHQ1) was added into the 96-well plate.

4. PCR amplification: The volunteers' genomic DNA was added into above premixed PCR 96-well plate for PCR reaction, and the PCR reaction procedure was at 95° C. for 2 min, followed by 35 cycles of 98° C. for 10 s, 60° C. for 15 s and 68° C. for 10 s.

5. Cas12a reaction: 1 µL of PCR reaction liquid was added into the premixed 96-well plate for fluorescence detection and reaction was performed at 37° C. for 15 min and then stopped at 98° C. for 2 min.

Figure 17:
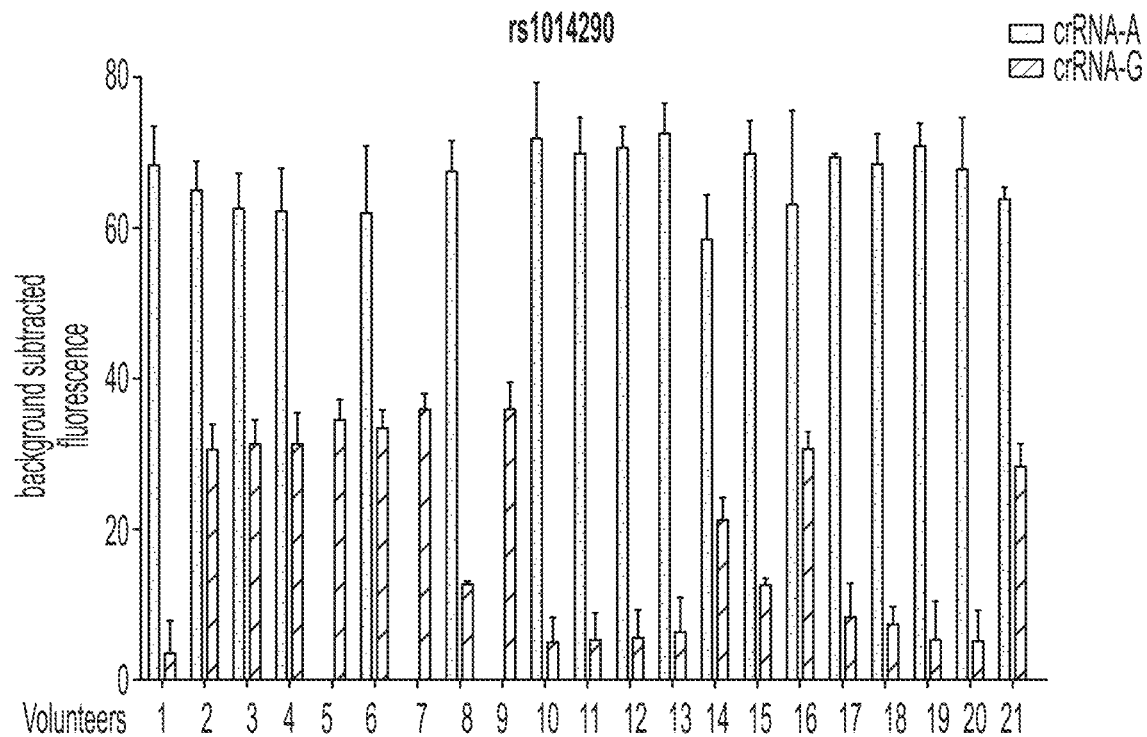
FIG. 17 shows the detection values of 1 SNP site (gout related) by using HOLMES method, with samples from 21 volunteers.

6. Fluorescence detection: Detection was performed by a microplate reader with the excitation at 535 nm and emission at 556 nm. As shown in FIG. 17, population with A: A genotype had higher gout risk, so, those except volunteer 5, 7 and 9 who had either A: G or G: G genotypes shall pay more attention to gout risk.

Example 11. Detection of Microorganisms Such as E. coli in Environmental Water by LAMP in Combination with Cas Protein E. coli gyrB gene was chosen as the detection target to indirectly test the presence and absence of microorganisms such as E. coli in water.

1. Preparation of crRNA: First, T7-crRNA-F and synthetic oligonucleotides of T7-crRNA-gyrB (Table 5) were annealed to prepare the template for transcription. Specifically, 4 µM of paired oligonucleotides were annealed in 1× Taq DNA polymerase reaction buffer (Transgen Biotech) with a volume of 50-µL, following the annealing procedure: initial denaturation at 95° C. for 5 min, and then cooling down from 95° C. to 20° C. using thermocycler (decrease by 1° C. per min). crRNA was synthetized using T7 high-yield transcription kit, and the reaction was performed at 37° C. overnight (about 16 h). Then, the RNA was purified with an RNA purification and concentration kit, quantitated with NanoDrop 2000C, finally diluted to a concentration of 10 µM and stored at −80° C. in a refrigerator for later use.

2. LAMP amplification: Sterilized water and liquid polluted with E. coli was taken as the negative control and sample to be detected, respectively. The total volume of each reaction system was 25 µL, 1.6 µM LAMP-FIP and LAMP-BIP primers, 0.2 µM LAMP-F3 and LAMP-B3 primers, and 0.4 µM LAMP-LoopF and LAMP-LoopB primers were used, and WarmStart® LAMP Kit (NEB) was used for LAMP reaction. LAMP reaction procedure was at 65° C. for 30 min. After LAMP was completed, reaction was quenched at 80° C. for 10 min, which were directly used for Cas12a reaction.

3. Cas12a reaction: In a 20-µL reaction system was added with 0.5 µM crRNA purified from Step 1, 0.25 µM Cas12a, 1 µL of LAMP products, 0.5 µM fluorescent probe (HEX-N12-BHQ1), NEB buffer 3.1 and 0.5 µL of RNA enzyme inhibitor. The reaction was carried out at 37° C. for 15 min.

Figures 19A, 19B:
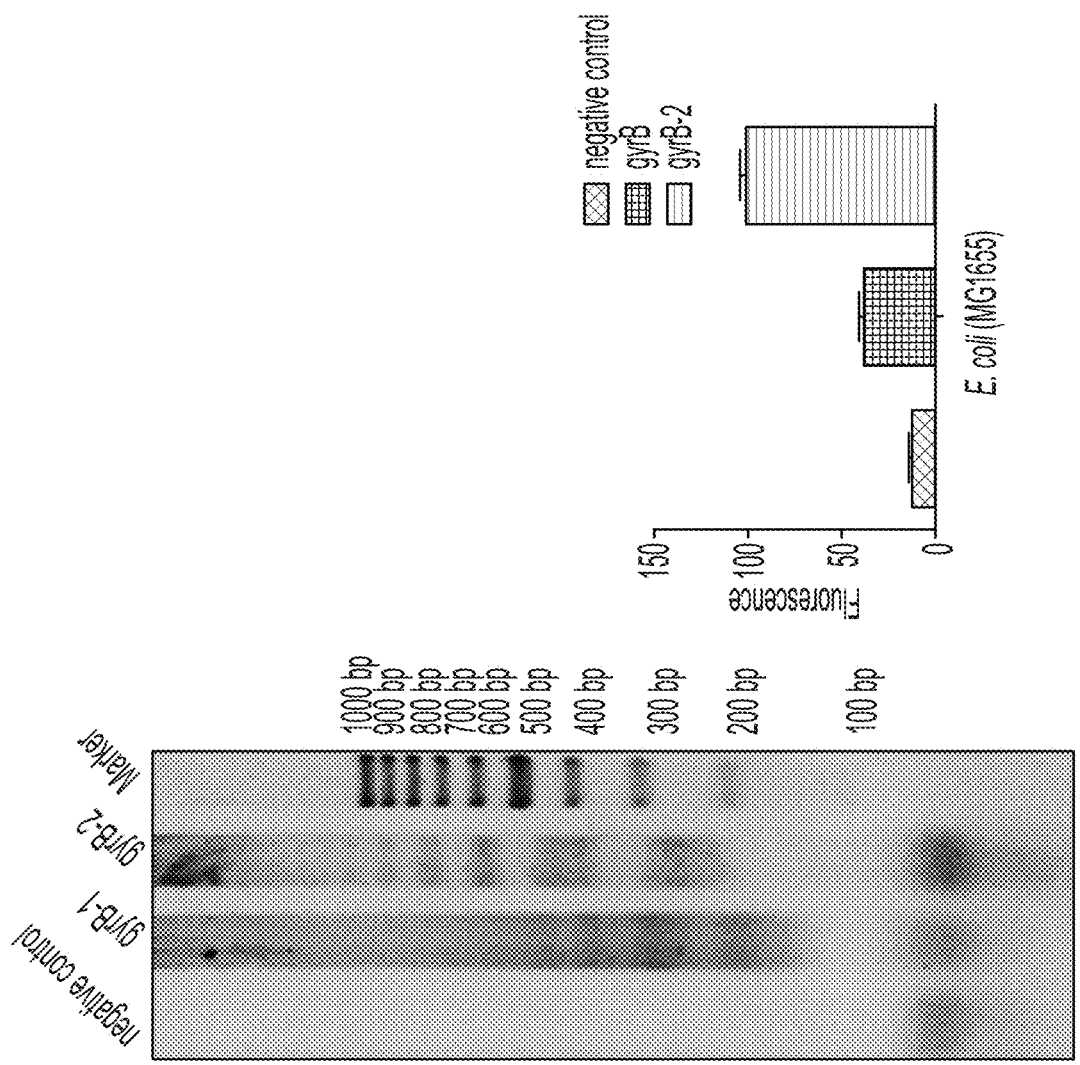
FIG. 19 shows the detection of *E. coli* with the combination of LAMP and HOLMES in the system. (A) The electrophoretogram of the *E. coli* gyrB gene amplified by LAMP. Two groups of primers (i.e. gyrB-1 and gyrB-2) were used to amplify the gyrB gene, which is the informative gene of *E. coli*. (B) Detection of the LAMP amplification products with HOLMES detection system. Negative control: The sample was sterilized water, and the gyrB gene was amplified or the result thereof was detected with gyrB-1 amplification primers. gyrB-1: The sample was the *E. coli* to be detected, and gyrB gene was amplified or the result thereof was detected with the first group of gyrB gene amplification primers. gyrB-2: The sample was the *E. coli* to be detected, and gyrB gene was amplified or the result thereof was detected with the second group of gyrB gene amplification primers.

4. Fluorescence detection: 20 µL of inactivated reaction liquid was added into a 96-well plate and detected with a microplate reader with the excitation at 535 nm and emission at 556 nm. The result is shown in FIG. 19.

Example 12. Detection of SNP with LAMP Amplification in Combination with Cas Protein 1. Preparation of crRNA: T7-crRNA-F and synthetic oligonucleotides of T7-crRNA-rs5082-T/T7-crRNA-rs5082-G/T7-crRNA-rs1467558-T/T7-crRNA-rs1467558-C (Table 5) were annealed to prepare the template for transcription. Specifically, 4 µM of paired oligonucleotides were annealed in 1× Taq DNA polymerase reaction buffer (Transgen Biotech) with a volume of 50-µL, following the annealing procedure: initial denaturation at 95° C. for 5 min, and then cooling down from 95° C. to 20° C. using thermocycler (decrease by 1° C. per min). crRNA was synthetized using T7 high-yield transcription kit, and the reaction was performed at 37° C. overnight (about 16 h). Then, the RNA was purified with an RNA purification and concentration kit, quantitated with NanoDrop 2000C, finally diluted to a concentration of 10 µM and stored at −80° C. in a refrigerator for later use.

2. LAMP amplification: Human genomic HEK293T was used as the sample. The total volume of each reaction system was 25 µL 1.6 µM LAMP-FIP and LAMP-BIP primers, 0.2 µM LAMP-F3 and LAMP-B3 primers, and 0.4 µMLAMP-LoopF and LAMP-LoopB primers were used, and WarmStart® LAMP Kit (NEB) was used for LAMP reaction. LAMP reaction procedure was at 65° C. for 30 min. After LAMP was completed, the reaction was quenched at 80° C. for 10 min, which were directly used for Cas12a reaction.

3. Cas12a reaction: In a 20-µL reaction system was added with 0.5 µM crRNA purified from Step 1, 0.25 µM Cas12a, 1 µL of LAMP products, 0.5 µM fluorescent probe (HEX-N12-BHQ1), NEB buffer 3.1 and 0.5 µL of RNA enzyme inhibitor. The reaction was carried out at 37° C. for 15 min.

4. Fluorescence detection: 20 µL of inactivated reaction liquid was added into a 96-well plate and detected with a microplate reader with the excitation at 535 nm and emission at 556 nm. The result is shown in FIG. 20.

Example 13. Detection of Microorganisms Such as E. coli in Environmental Water by RPA Amplification in Combination with Cas Protein E. coli gyrB gene was chosen as the detection target to indirectly test the presence and absence of microorganisms such as E. coli in water.

1. Preparation of crRNA: T7-crRNA-F and synthetic oligonucleotides of T7-crRNA-gyrB (Table 5) were annealed to prepare the template for transcription. Specifically, 4 μM of paired oligonucleotides were annealed in 1×PCR buffer (Transgen Biotech) with a volume of 50-μL, following the annealing procedure: initial denaturation at 95° C. for 5 min, and then cooling down from 95° C. to 20° C. using thermocycler (decrease by 1° C. per min). crRNA was synthesized using T7 high-yield transcription kit, and the reaction was performed at 37° C. overnight (about 16 h). Then, the RNA was purified with an RNA purification and concentration kit, quantitated with NanoDrop 2000C, finally diluted to a concentration of 10 μM and stored at −80° C. in a refrigerator for later use.

2. RPA amplification: Sterilized water and liquid polluted with E. coli was taken as the negative control and sample to be detected, respectively. The total volume of each reaction system was 25 μL, 0.5 μM RPA-gyrB-F (or RPA-gyrB-F2) and RPA-gyrB-R2 were used as primer, and TwistAmp® Basic Kit (TwistDX) was used for RPA reaction. RPA reaction procedure was at 37° C. for 30 min. After RPA was completed, the reaction was quenched at 80° C. for 10 min, which were directly used for Cas12a reaction.

3. Cas12a reaction: In a 20-μL reaction system was added with 0.5 μM crRNA purified from Step 1, 0.25 μM Cas12a, 1 μL of RPA products, 0.5 μM fluorescent probe (HEX-N12-BHQ1), NEB buffer 3.1 and 0.5 μL of RNA enzyme inhibitor. The reaction was carried out at 37° C. for 15 min.

Figures 21A, 21B:
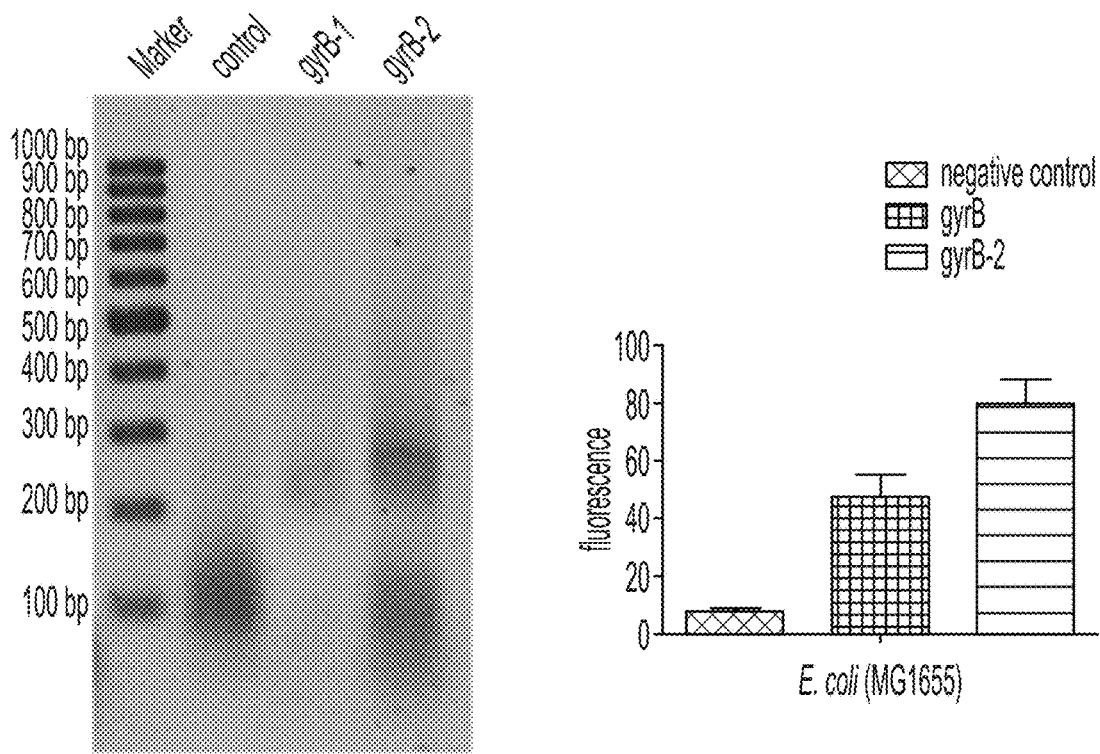
FIG. 21 shows the detection of *E. coli* with the combination of RPA and HOLMES in the system. (A) Amplification of the *E. coli* gyrB gene with RPA. Two groups of primers (i.e. gyrB-1 and gyrB-2) were used to amplify the gyrB gene, which is the informative gene of *E. coli*. (B) Detection of the RPA amplification products with HOLMES detection system. Negative control: The sample was sterilized water, and the gyrB gene was amplified or the result thereof was detected with gyrB-1 amplification primers. gyrB-1: The sample was the *E. coli* to be detected, and gyrB gene was amplified or the result thereof was detected with the first group of gyrB amplification primers. gyrB-2: The sample was the *E. coli* to be detected, and gyrB gene was amplified or the result thereof was detected with the second group of gyrB amplification primers.

4. Fluorescence detection: 20 μL of inactivated reaction liquid was added into a 96-well plate and detected with a microplate reader with the excitation at 535 nm and emission at 556 nm. The result is shown in FIG. 21.

Example 14. Cas12b had Collateral Cleavage Activity

1. Preparation of Guide RNA (sgRNA)

First, the plasmid pUC18-guide RNA-T1 with pUC18 as the plasmid backbone was constructed by inserting T7 promoter and the template DNA sequence for transcribing guide RNA into pUC18 (note: the guide RNA transcribed from the template was targeted to the sequence named T1 in the research). The method is as follow: PUC18 plasmid was used as the template with pUC18-1-F and pUC18-1-R as primers for the first round of PCR amplification, and the PCR products were ligated using T4 DNA ligase before being transformed into DH10b. The correct clone was obtained by sequencing, which was named as pUC18-guide RNA-T1-pre. The pUC18-guide RNA-T1-pre was then used as the template for the second round of PCR amplification with pUC18-2-F and pUC18-2-R as primers. In a similar way, the PCR products were ligated and transformed into DH10b, and finally, a correctly sequenced plasmid pUC18-guide RNA-T1 is obtained.

Then, guide RNA was synthetized, using T7 high-yield transcription kit (Thermo), with the plasmid PUC18-guide RNA-T1 as the template. The reaction was performed overnight at 37° C. (12-16 h).

At last, DNase I was added into the transcription system (2 μL of DNase 1 added per 50 μL of the transcription system) and the system was put in 37° C. water bath for 30 min to remove plasmid DNA. The RNA was then purified with an RNA purification and concentration kit, quantitated with NanoDrop 2000C, diluted to a concentration of 10 μM and stored at −80° C. in a refrigerator for later use.

2. Preparation of Target DNA:

(1) If the target DNA is single stranded, a 66-bp oligonucleotide was directly synthesized as the target DNA (target-T1-R), in which the 20-bp target sequence (T1) recognized by guide RNA is contained.

(2) If the target DNA is double stranded, two complementary 66-bp oligonucleotides (i.e. target-T1-F and target-T1-R) were directly synthesized, in which the 20-bp target sequence (T1) recognized by guide RNA is contained. The two oligonucleotides were annealed to obtain target DNA. Specifically, 1 μM of paired oligonucleotides were annealed in 1×PCR buffer (Transgen Biotech) with a volume of 20-μL, following the annealing procedure: initial denaturation at 95° C. for 5 min, and then cooling down from 95° C. to 20° C. using thermocycler (decrease by 1° C. per min).

3. Cas12b Reaction:

(1) Annealing of guide RNA: guide RNA was diluted to an appropriate concentration (10 μM) and annealed in a PCR instrument, following the annealing procedure: denaturation at 75° C. for 5 min, and then cooling down from 75° C. to 20° C. (decrease by 1° C. per min).

(2) Incubation of guide RNA and C2c1: the annealed guide RNA and the C2c1 of equal molar concentrations were mixed and placed at 30° C. for 20-30 min.

(3) Cas12b reaction: In a 20-μL reaction system, a mixture of guide RNA and C2c1 (the concentration of both is 250 μM or 500 μM) incubated in Step (2), target DNA (final concentration of 50 nM), FAM-labelled oligonucleotides (target-DNMT1-3-R-FAM-5') or fluorescence quenching probe (HEX-N12-BHQ1, final concentration of 500 nM), 2 μL of 10×NEB Buffer 3.1 and 0.5 μL of RNA enzyme inhibitor (40 U/μL) were added. After mixing well, they were allowed to react at 48° C. for 30 min. Afterwards, they were heated at 98° C. for 5 min in a PCR instrument for inactivation.

Figure 22:
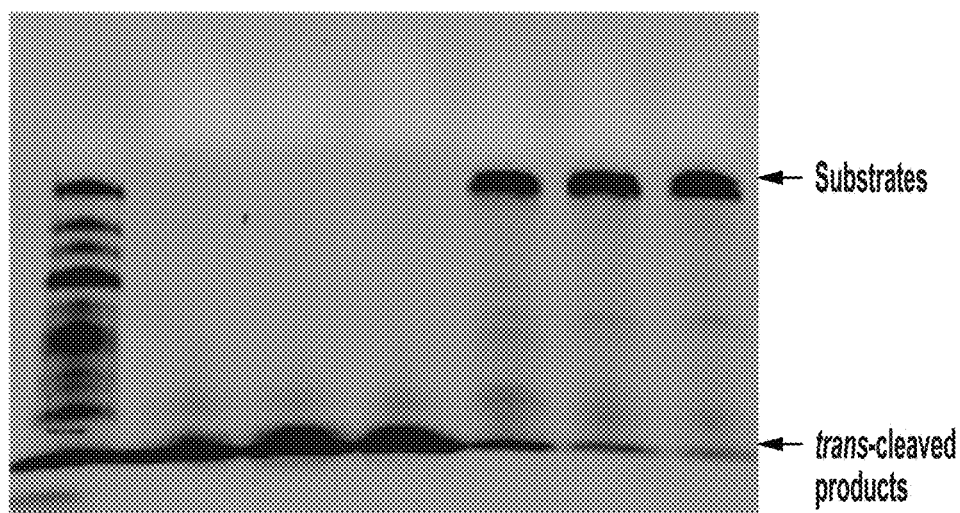
FIG. 22 shows the detection of the collateral ssDNA cleavage activity of Cas12b with ssDNA as target DNA. After the collateral cleavage reaction, the reactants were subject to denatured gel electrophoresis separation with 12% urea and detected with the fluorescence imaging system. The number in the brackets stood for the final concentration, in nM, of reactants. The 50 nM ssDNA of 66 nts was used as the target DNA, and 50 nM 5'-end FAM-labelled ssDNA was used as the ssDNA probe. As shown in the figure, with the addition of Cas12b, guide RNA and target DNA, FAM-labelled ssDNA was cleaved into fragments, demonstrating that Cas12b had collateral ssDNA cleavage activity.

4. Detection of Cas12b for Trans-Cleavage Activity by the Urea Denaturing Gel Electrophoresis Method:

20 μL of inactivated reaction liquid was electrophoretically separated by the urea denaturing gel electrophoresis method, followed by being imaged with the fluorescence imaging system ImageQuant LAS 4000 mini (GE Healthcare). The result is shown in FIG. 22.

Figure 23:
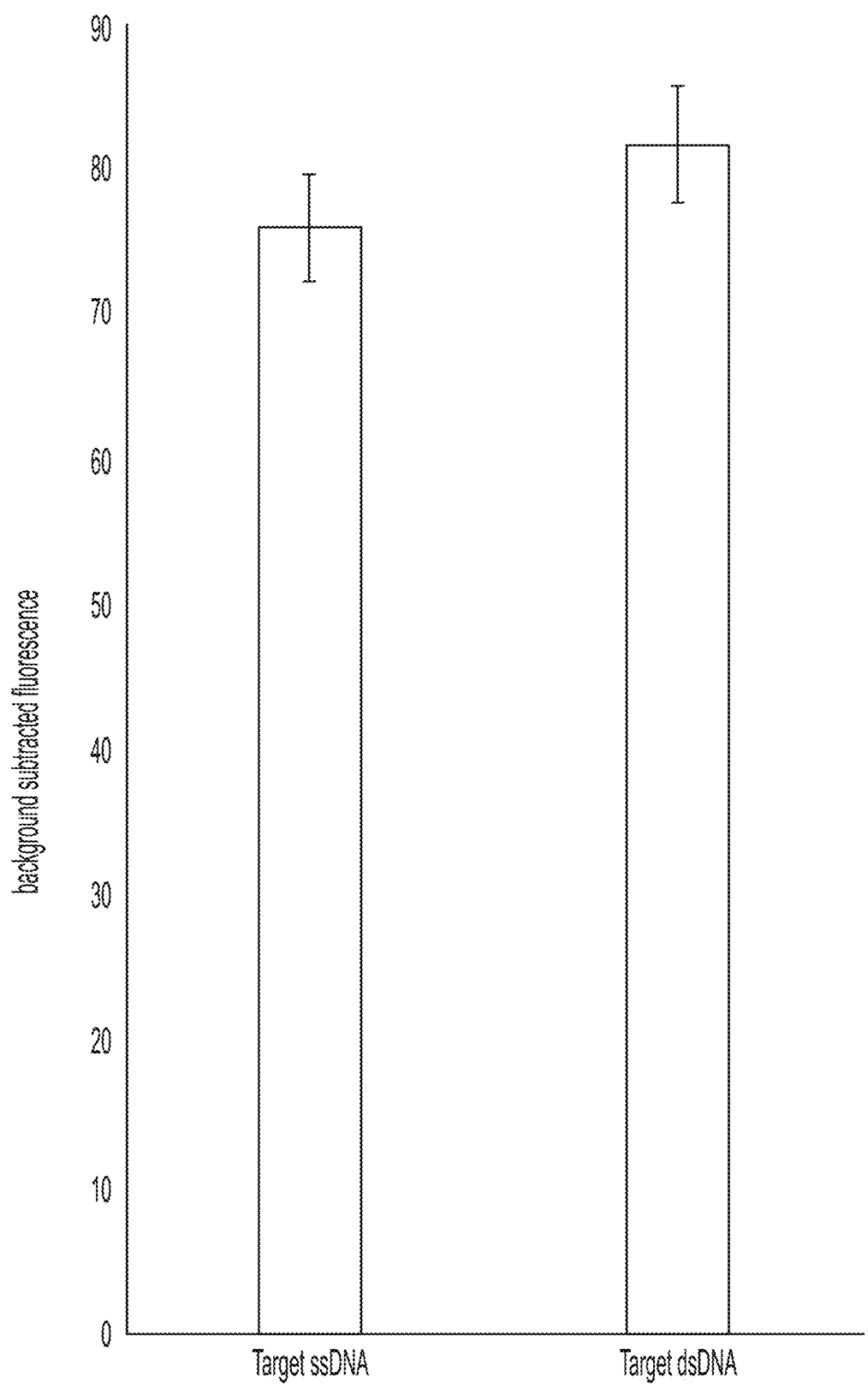
FIG. 23 shows the detection of the collateral ssDNA cleavage activity of Cas with ssDNA or dsDNA as target DNA. After collateral cleavage reaction was completed, the reactants were detected with a fluorescence microplate reader. The amount of Cas12b and guide RNA was 500 nM. 50 nM ssDNA (66-nt) or dsDNA (66-nt) was used as the target DNA. 500 nM ssDNA probe containing fluorescence reporter and quencher group (HEX-N12-BHQ1) was used as the ssDNA probe. As shown in the figure, upon the addition of Cas12b and guide RNA, no matter ssDNA template or dsDNA template, the collateral ssDNA cleavage activity could be detected.

5. Detection of Cas12b for Trans-Cleavage Activity by a Fluorescence Microplate Reader:

20 μL of inactivated reaction liquid was added into a 96-well plate and detected with a microplate reader with the excitation at 535 nm and emission at 556 nm. The result is as shown in FIG. 23.

Example 15. Sensitivity Test of the Trans Reaction (Trans-Cleavage) of Cas12b

Based on the detection of the fluorescence intensity excited by the fluorescence probe (HEX-N12-BHQ1), the target DNA concentration required for Cas12b to perform trans-cleavage activity could be determined, which is the sensitivity of Cas12b trans-cleavage reaction.

1. Preparation of Guide RNA:

First, the 20 bases of the target DNA targeting T1 in the guide RNA were substituted with the guide RNA targeting DNMT1-3 to obtain another plasmid pUC18-guide RNA-DNMT1-3 by PCR, with pUC18-guide RNA-T1 as the template as well as with the guide RNA-DNMT1-3-F and the guide RNA-DNMT1-3-R as primers.

Second, guide RNA was synthesized using the T7 high-yield transcription kit (Thermo), with the plasmid PUC18-guide RNA-DNMT1-3 as the template, the reaction was performed at 37° C. overnight (12-16 h).

At last, DNase I was added into the transcription system (2 µL of DNase I per 50 µL of the transcription system), and was put in a 37° C. water bath for 30 min to remove plasmid DNA, the RNA was then purified with an RNA purification and concentration kit, and then quantitated with NanoDrop 2000C, and stored at −80° C. in a refrigerator for later use.

2. Preparation of Target DNA

For the target DNA, the first method was a reaction system directly added with the Cas12b without amplification, as follows:

(1) if the target DNA is single stranded, a 50-bp oligonucleotide was directly synthesized as the target DNA (DNMT1-3(TTC PAM)-R), in which the 20-bp target sequence (DNMT1-3) recognized by guide RNA is contained.

(2) if the target DNA is double stranded, two complementary 50-bp oligonucleotides (i.e. DNMT1-3 (TTC PAM)-F and DNMT1-3 (TTC PAM)-R)) were directly synthesized, in which the 20-bp target sequence (DNMT1-3) recognized by guide RNA is contained. The two oligonucleotides were annealed to obtain short target DNA. Specifically, the paired oligonucleotides (2 µM) were annealed in 1×PCR buffer (Transgen Biotech) of the total volume 20 µL, followed by performing the annealing procedure: initial denaturation at 95° C. for 5 min, and then cooling down from 95° C. to 20° C. in a thermocycler (decrease by 1° C. per min).

(3) the single stranded or double stranded target DNA was serially diluted to 2 µM, 0.2 µM, 0.02 µM, 0.002 µM and 0.0002 µM for later use.

The second method is that a fragment with the target sequence (DNMT1-3) was inserted into a plasmid vector and amplified by LAMP reaction.

(1) The fragment with the target sequence (DNMT1-3) was inserted into the pEasy-Blunt Zero Cloning Vector using the pEasy-Blunt Zero Cloning Kit of Transgen company and verified by sequencing to obtain correct cloning.

(2) LAMP Amplification Reaction

The above plasmids were used as the template for LAMP amplification reaction, and the templates were added with 0 nM, 1 nM, 0.1 nM (diluted to $10^{-11}$ nM at 10 fold gradient). The total volume of each reaction system was 25-µL, the primers used is 1.6 µM LAMP-DNM-FIP and LAMP-DNM-BIP primers, 0.2 µM LAMP-DNM-F3 and LAMP-DNM-B3 primers, and 0.4 µM LAMP-DNM-LoopF and LAMP-DNM-LoopB, the kit used in the LAMP reaction was WarmStart® LAMP Kit (NEB). LAMP reaction program was at 65° C. for 30 min. After LAMP was completed, quenching at 80° C. for 10 min, and then directly used for Cas12b reaction.

3. Cas 12b Reaction (1) Annealing of guide RNA: guide RNA was diluted to an appropriate concentration (5 µM), and placed in a PCR instrument for annealing. The annealing procedure: denaturation at 75° C. for 5 min, and then cooling down from 75° C. to 20° C. (decrease by 1° C. per min).

(2) Incubation of guide RNA and Cas12b: the annealed guide RNA and the Cas12b of equal molar concentration were mixed and placed at 30° C. for 20-30 min.

(3) Cas 12b reaction: in a 20-µL reaction system, a mixture of guide RNA and Cas12b (the concentration of both is 250 µM) incubated in Step (2), 1 µL of target DNA or 1 µL of LAMP products, fluorescence probe (HEX-N12-BHQ1) (final concentration 500 nM), as well as 2 µL of 10×NEB buffer 3.1 and 0.5 µL of RNA enzyme inhibitor (40 U/µL) were added. After mixing well, they were allowed to react at 48° C. for 30 min. Afterwards, they were heated at 98° C. for 5 min in a PCR instrument to quench.

Figure 24:
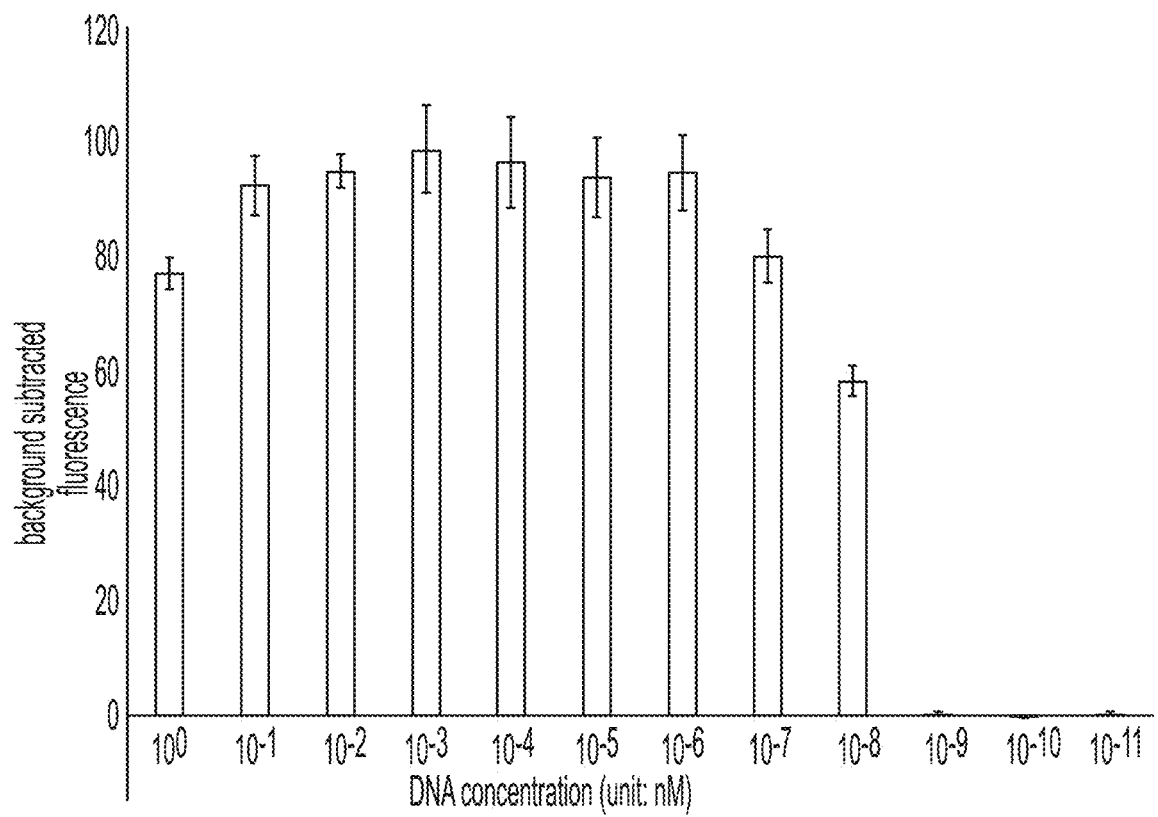
FIG. 24 shows the collateral ssDNA trans-cleavage activity generated by Cas12b with the combination of LAMP amplification for low-concentration target DNA.

4. Detection of Cas 12b Trans-Cleavage Activity by a Fluorescence Microplate Reader:

20 µL of reaction liquid inactivated was added into a 96-well plate and detected with a microplate reader with the excitation at 535 nm and emission at 556 nm. Upon combining with LAMP amplication, the Cas12b could produce significant collateral ssDNA trans-cleavage activity for as low as 10 aM target DNA. As is shown in FIG. 24.

Figure 1B:
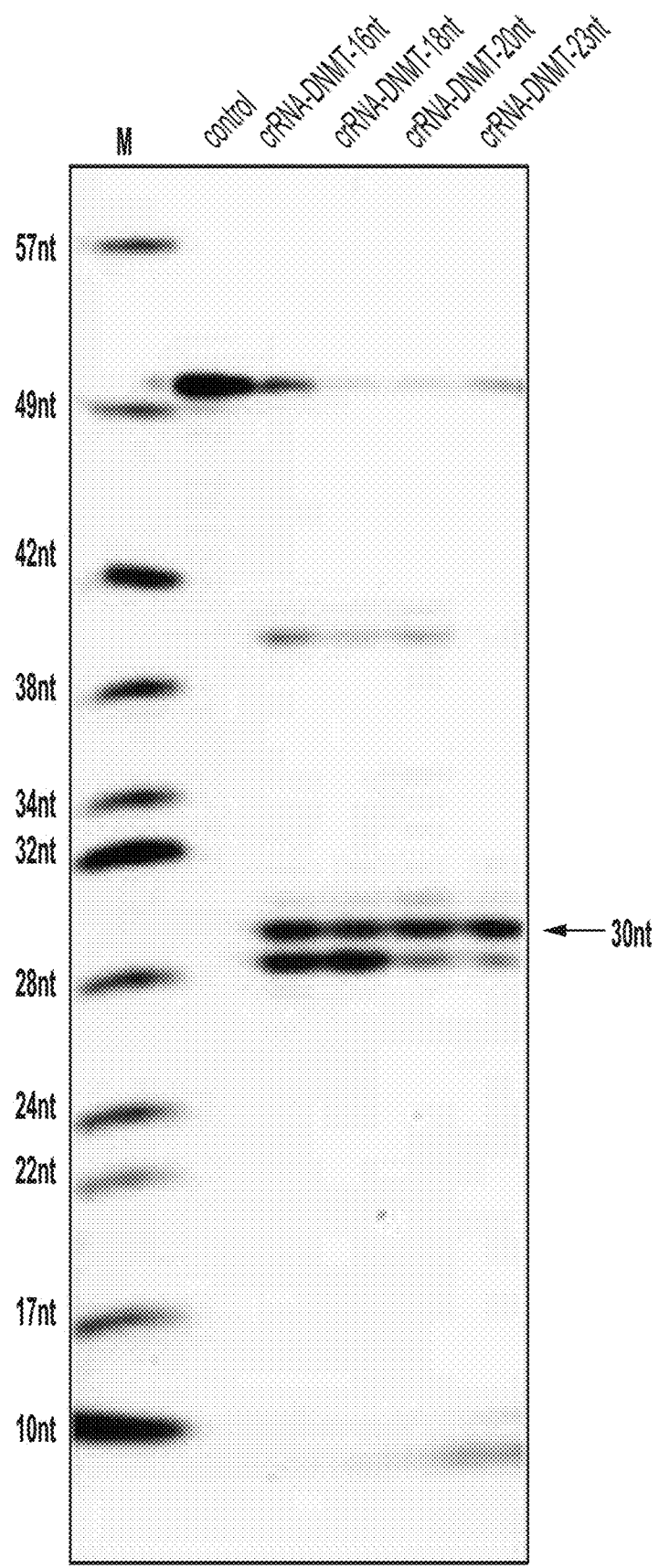
Figure 1C:
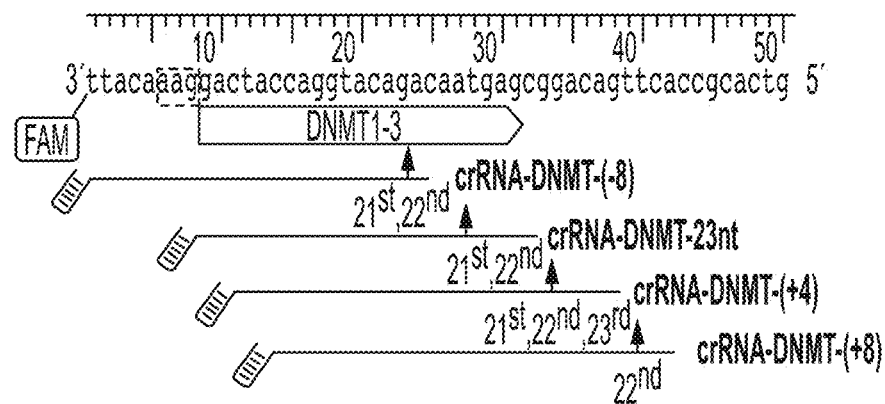
Figure 1D:
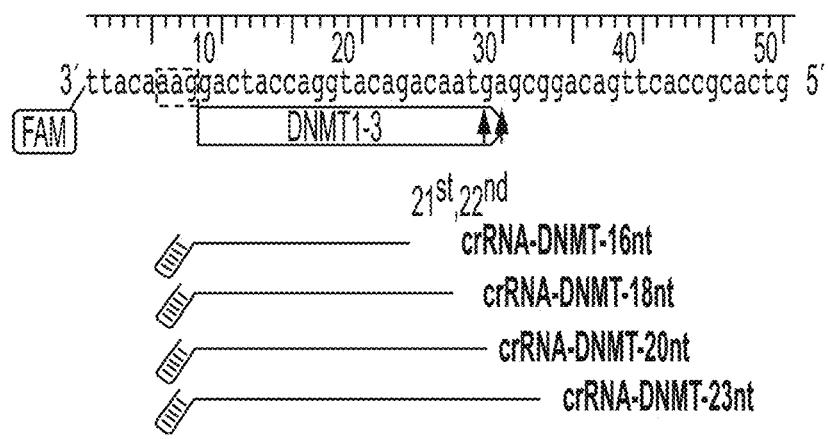
Figure 1E:
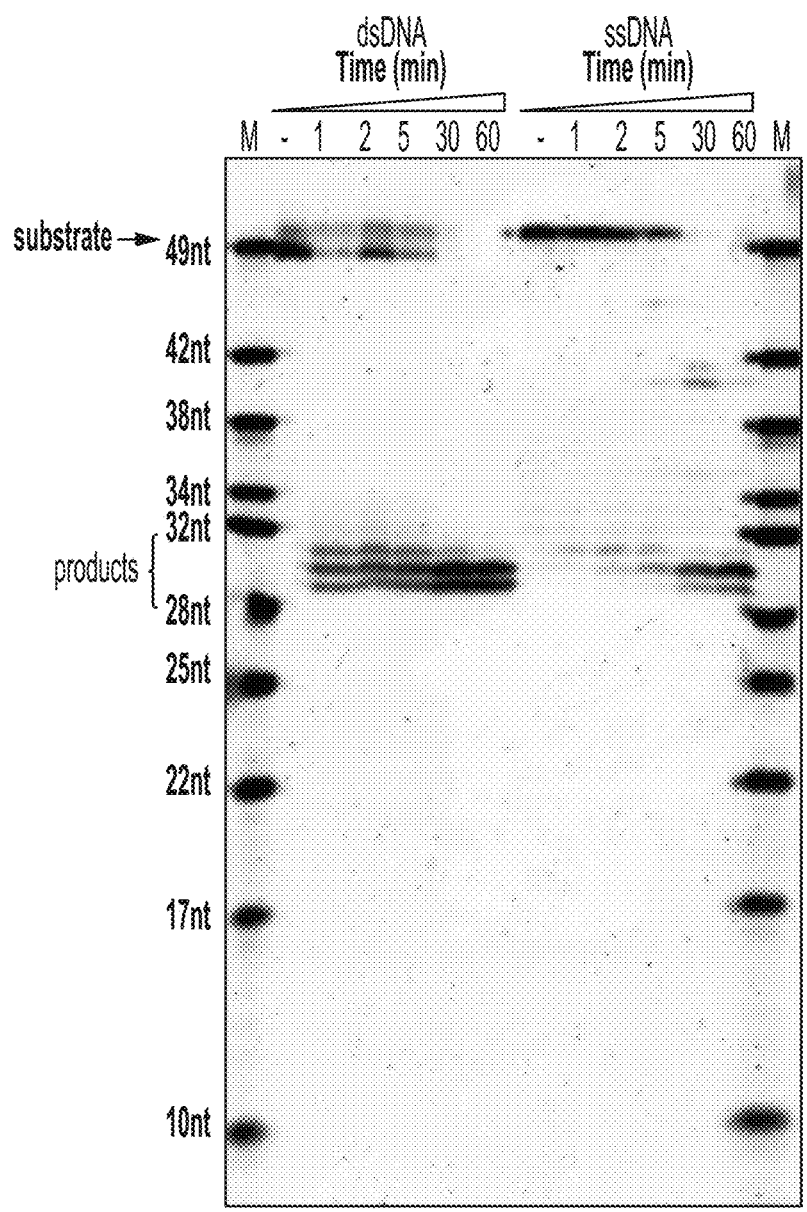
Figure 1F:
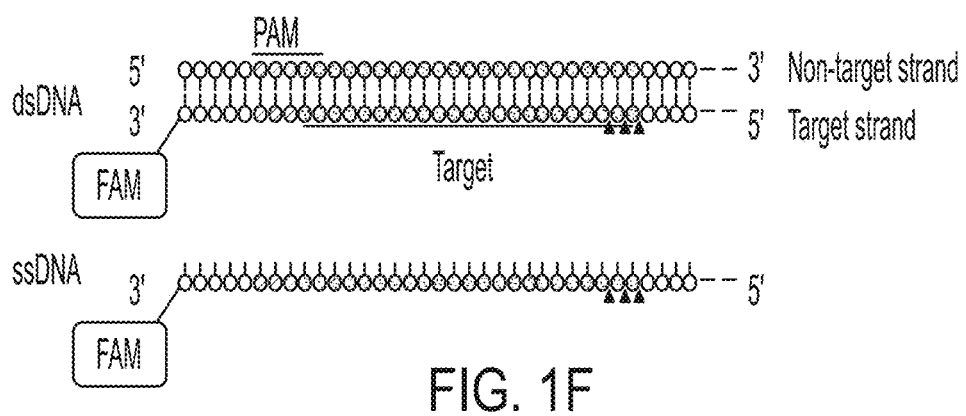
Figure 1G:
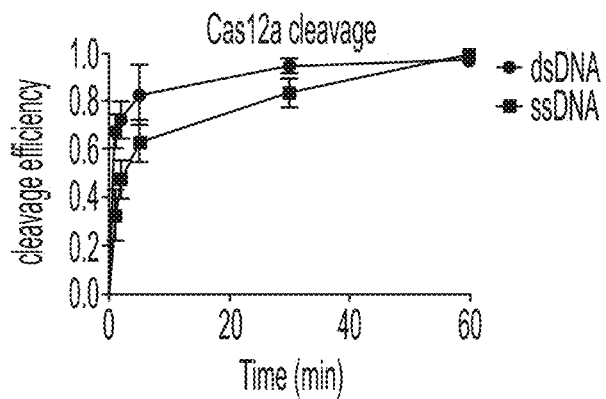
Figure 2A:
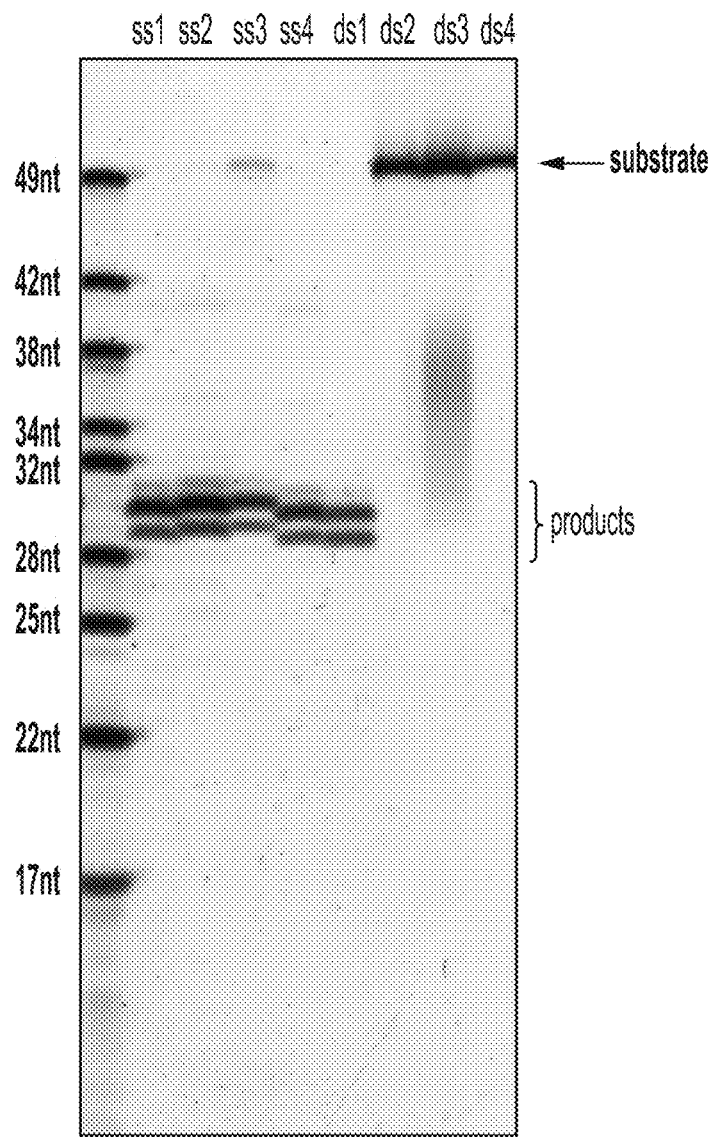
FIG. 2 shows Cas12a cleaves target single-stranded DNA independent of PAM sequence required for cleaving double strands.
FIG. 2B discloses SEQ ID NOS 3, 11, 13, 12, 1, 3, 14, 11, 16, 13, 15, and 12, respectively, in order of appearance.
Figure 2B:
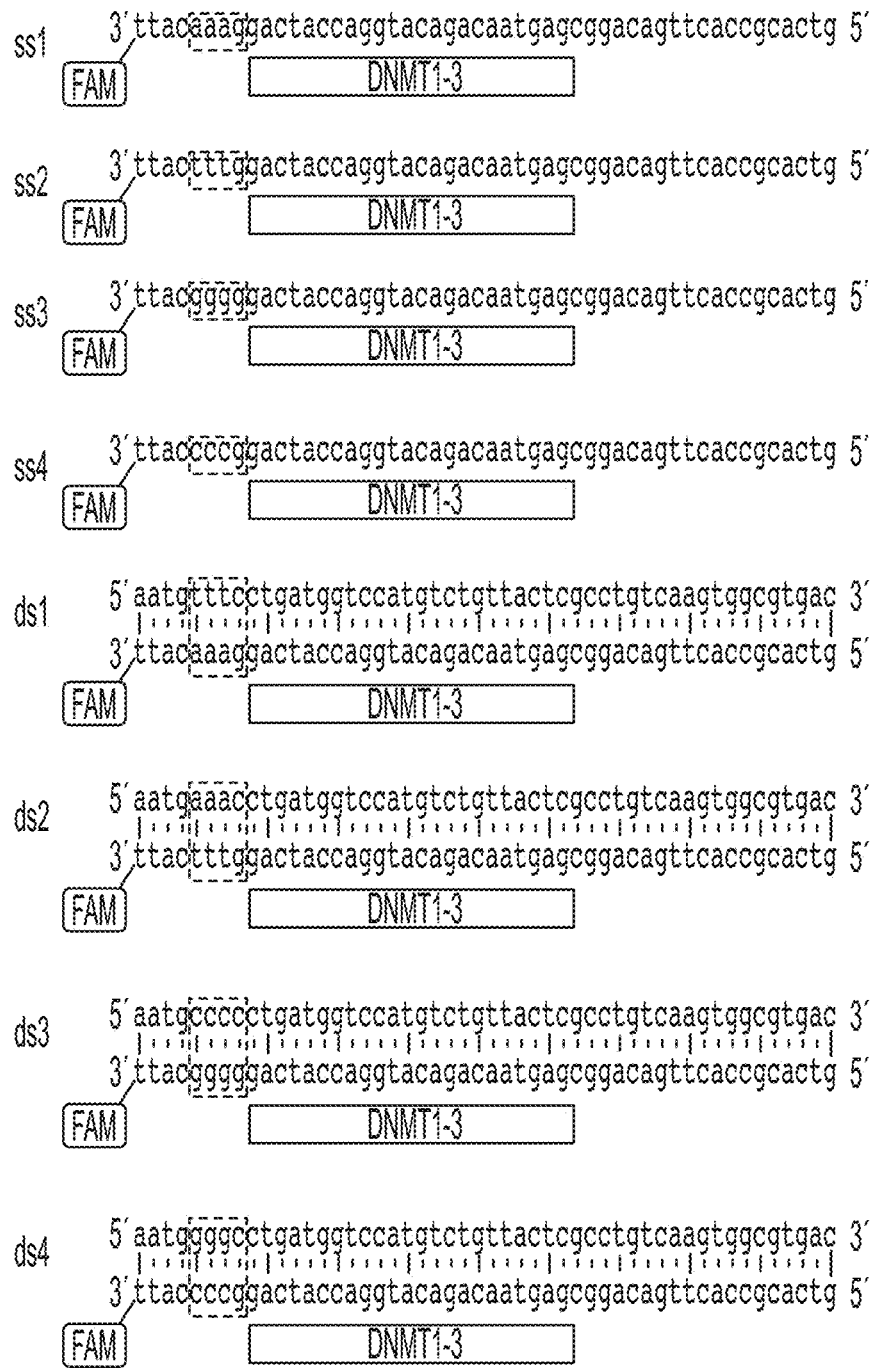

The cis cleavage property of Cas12a to cleave target ssDNA:

First, in order to test the ssDNA cleavage property of Cas12a, several crRNAs (Table 1) targeting the short ssDNA (DMNT1-3) were designed with 5(6)-carboxyfluorescein (FAM) labelled at the 3' end. After cleavage of FnCas 12a, the reaction product was analyzed by denatured urea polyacrylamide gel electrophoresis (urea PAGE). Single-stranded DNA cleavage by Cas12a was found to be programmable, i.e., the cleavage site is from the first base in the 3' end of the target sequence paired with the crRNA guide sequence to near the 22nd base (from 21st to 23rd bases) of the target sequence counted in the 5' end, as shown in FIGS. 1A and 1C. The dsDNA cleavage of Cas12a requires a PAM sequence, whereas ssDNA cleavage does not require a PAM sequence (FIG. 1A, 1B and FIG. 2), which is similar to Cas9-mediated ssDNA cleavage. However, the Cas12a-mediated ssDNA cleavage activity is dependent on the stem-loop structure in crRNA, as shown in FIG. 1A, while Cas9 still exhibits weak cleavage activity against ssDNA with only 20-nt complementary RNA sequences. The stem-loop structure of crRNA is important for stabilizing the structure of Cas12a, which is responsible for the necessity of stem-loop structure of crRNA for ssDNA cleavage of Cas12a. It is further tested whether the ssDNA cleavage site by Cas12a can passed through a shorter guide sequence crRNA, such that the cleavage is outside the recognition site. When the length of the guide sequence is 16 nt, 18 nt or 20 nt, all of these crRNAs resulted in cleavage by Cpf1 near the 22nd base, as shown in FIGS. 1B and 1D, meaning that the cleavage site is 4 nt, 2 nt or 0 nt outside the recognition site. Next, the cleavage efficiency of Cas12a for different substrates was tested using dsDNA and ssDNA substrates, respectively, as shown in FIG. 1F. Similar to the case of Cas9 cleavage, ssDNA cleavage is slower than dsDNA cleavage, as shown in FIG. 1E to 1G. These results indicate that the mechanism of Cas12a's ssDNA recognition and cleavage may be different from dsDNA, which is a less efficient PAM-independent recognition cleavage mode; the PAM sequence accelerates target dsDNA recognition and/or cleavage by Cas12a.

Figure 3A:
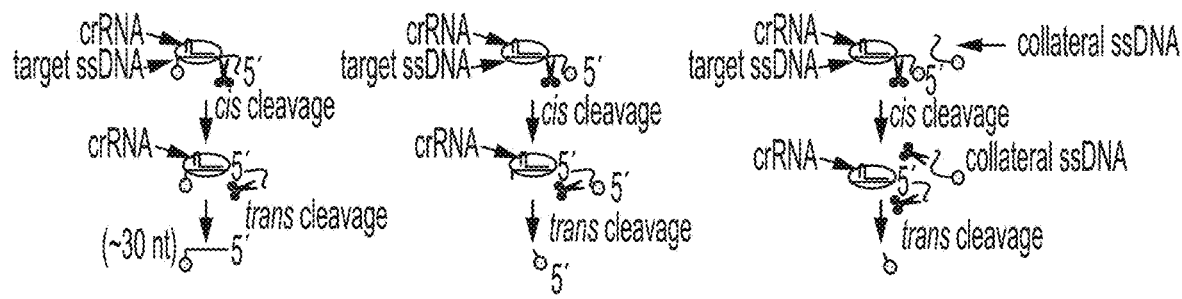
FIG. 3 shows the trans-cleavage characteristics of the Cas12a cleaving single-stranded DNA.
Figure 3B:
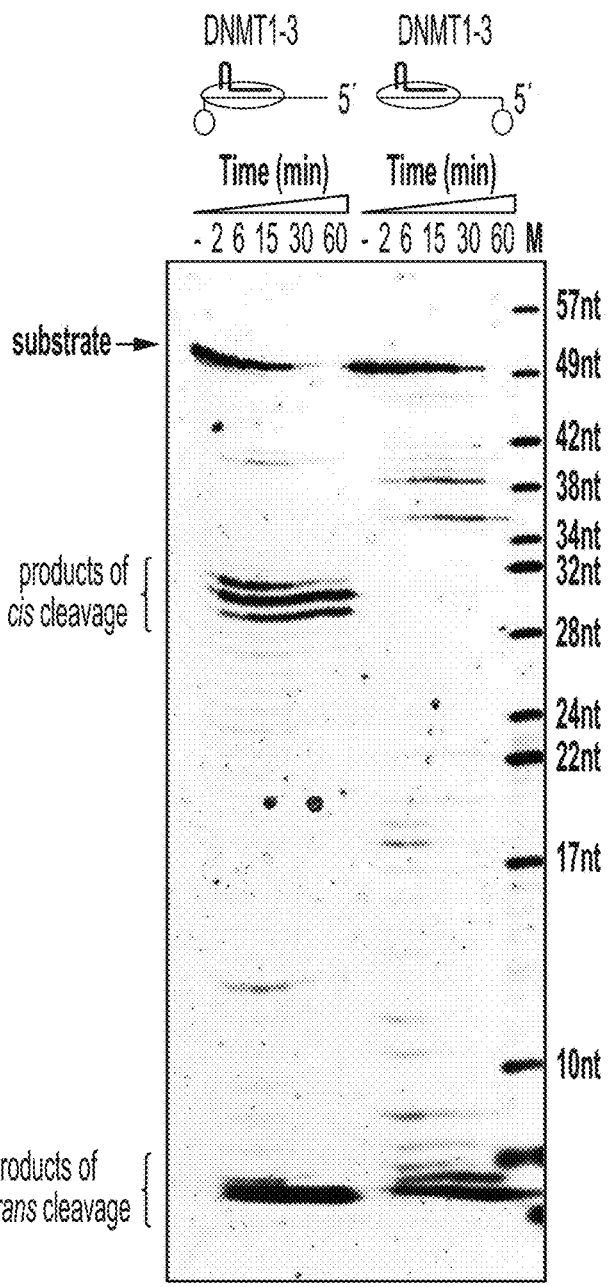
Figure 3C:
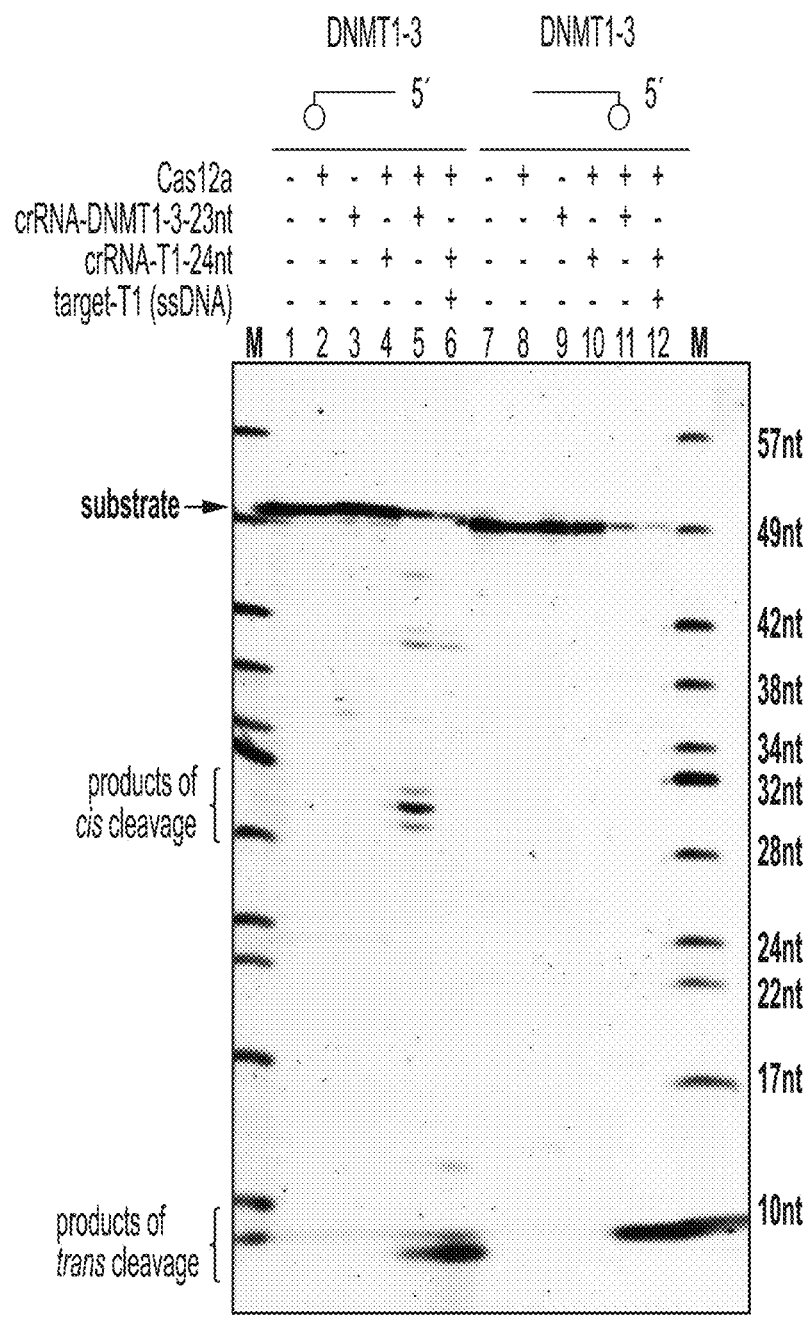
Figure 3D:
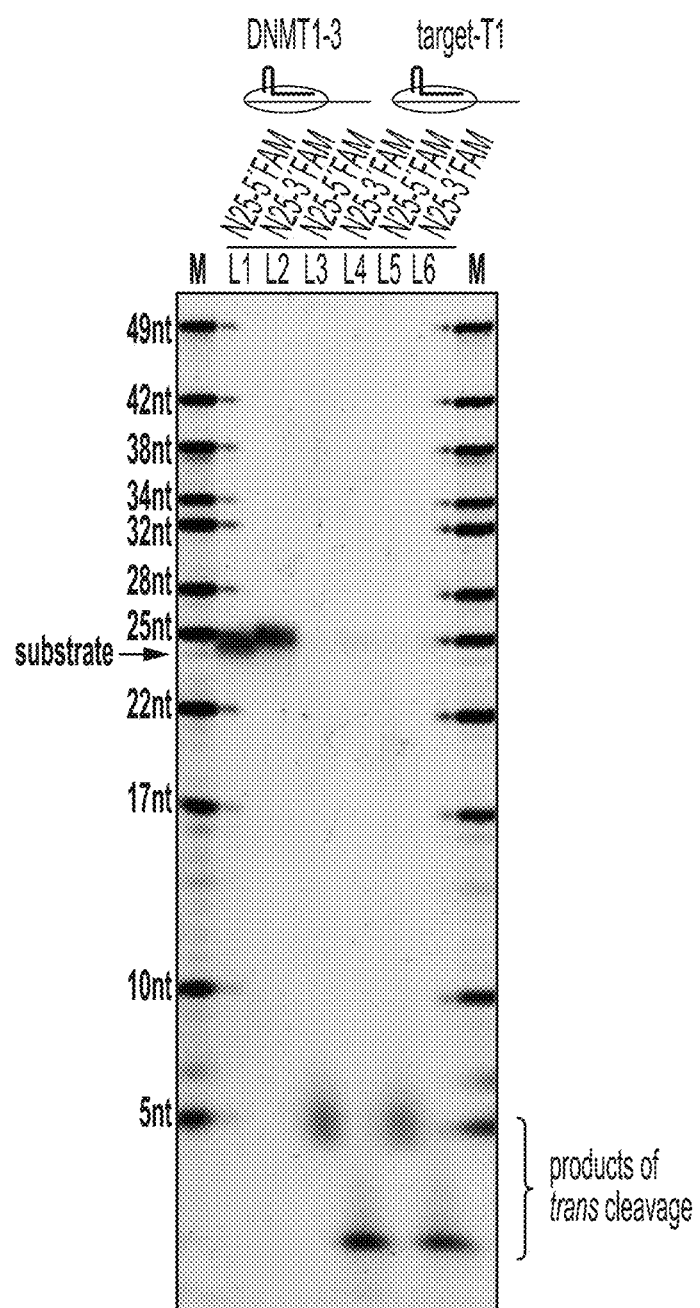

The trans cleavage property of Cas12a to cleave ssDNA:

When the target ssDNA is labelled at the 3' end, Cas12 cleaves around the 22nd base, as shown in FIG. 1. However, when the labelling was at the 5' end, no cleavage product band of the predicted size was observed, but a short (<6 nt) FAM-labelled product was produced, as shown in FIG. 3B. Through detailed experiments, once the ternary complex Cas12a/crRNA/target ssDNA is formed, the 5'-end labelled target ssDNA (DNMT1-3) (Table 1) is cleaved and a short FAM-labelled product is produced, as shown in FIG. 3C. In addition, the ternary complex also cleaves ssDNA that does not have any complementary sequence to the crRNA in any other reaction system (i.e., collateral ssDNA), as shown in FIGS. 3C and 3D. This cleavage phenomenon is a trans cleavage, which is distinguished from a programmable cis cleavage. Trans cleavage was also observed when the target ssDNA was labelled at the 3'-end, but many cis-cleaved products were left, as shown in FIG. 3B, which may be due to the formation of complex Cas12a/crRNA/target ssDNA, which protected the labelled 3'-end of the target ssDNA from being exposed in the active nuclease site of the ternary complex, and these cleavage processes can be shown in FIG. 3A.

Figure 4A:
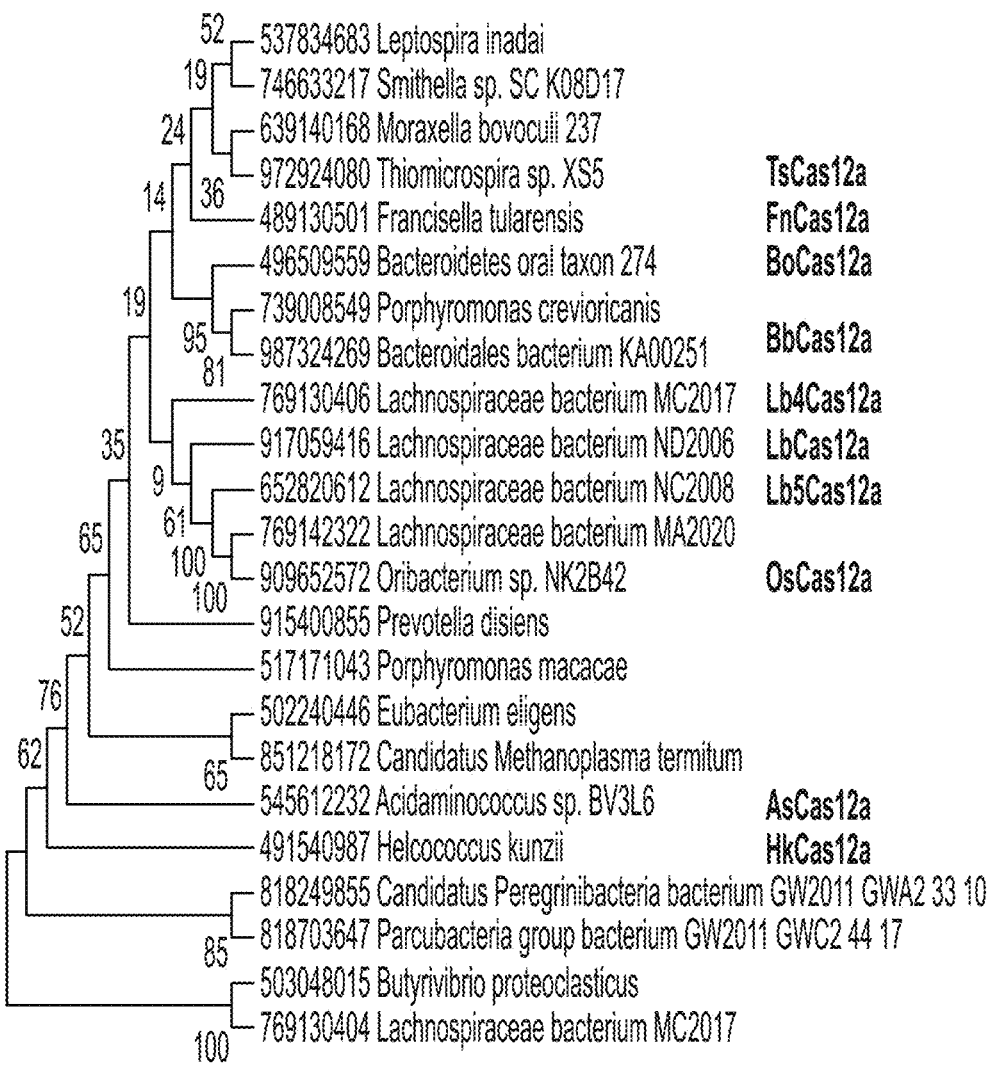
FIG. 4 shows 10 different sources of Cas12a tested, all of which have cis- and trans-cleavage activity for single-stranded DNA.
Figure 4B:
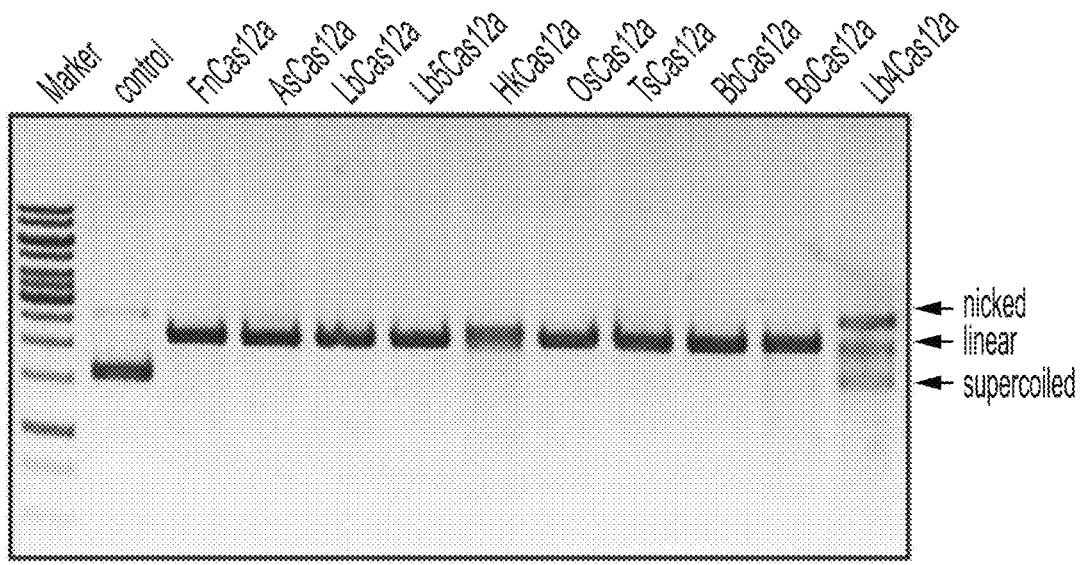
Figure 4C:
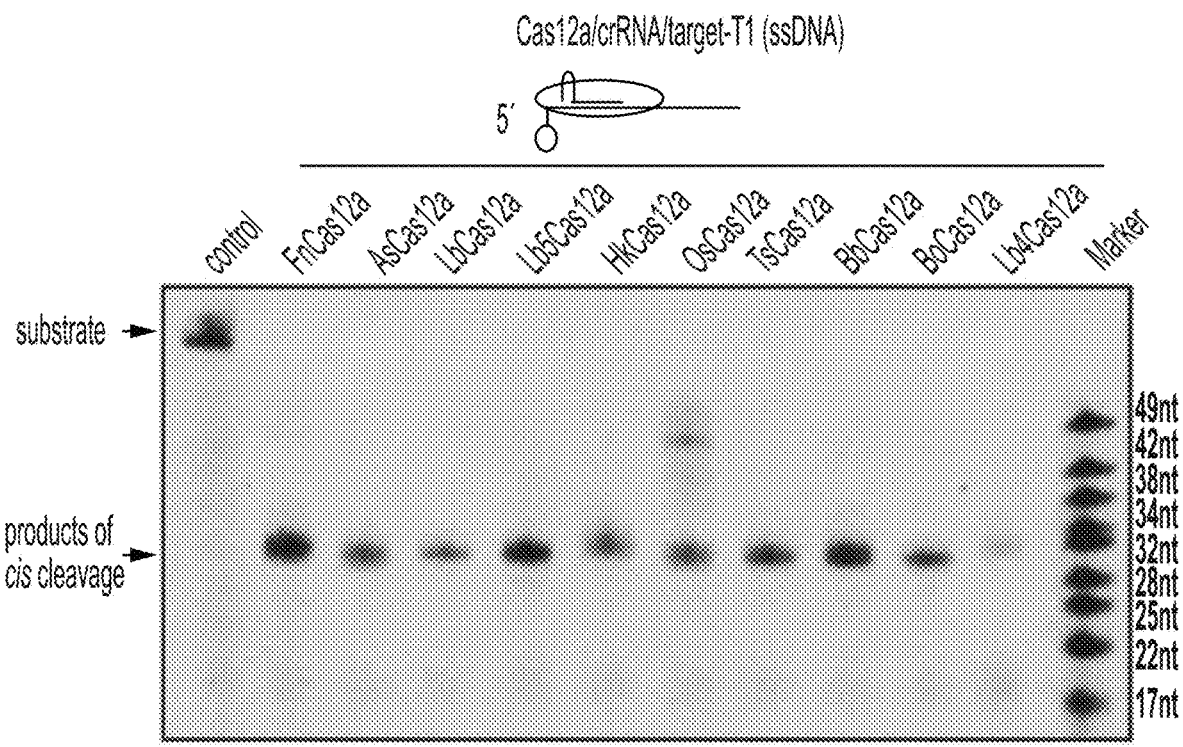
Figure 4D:
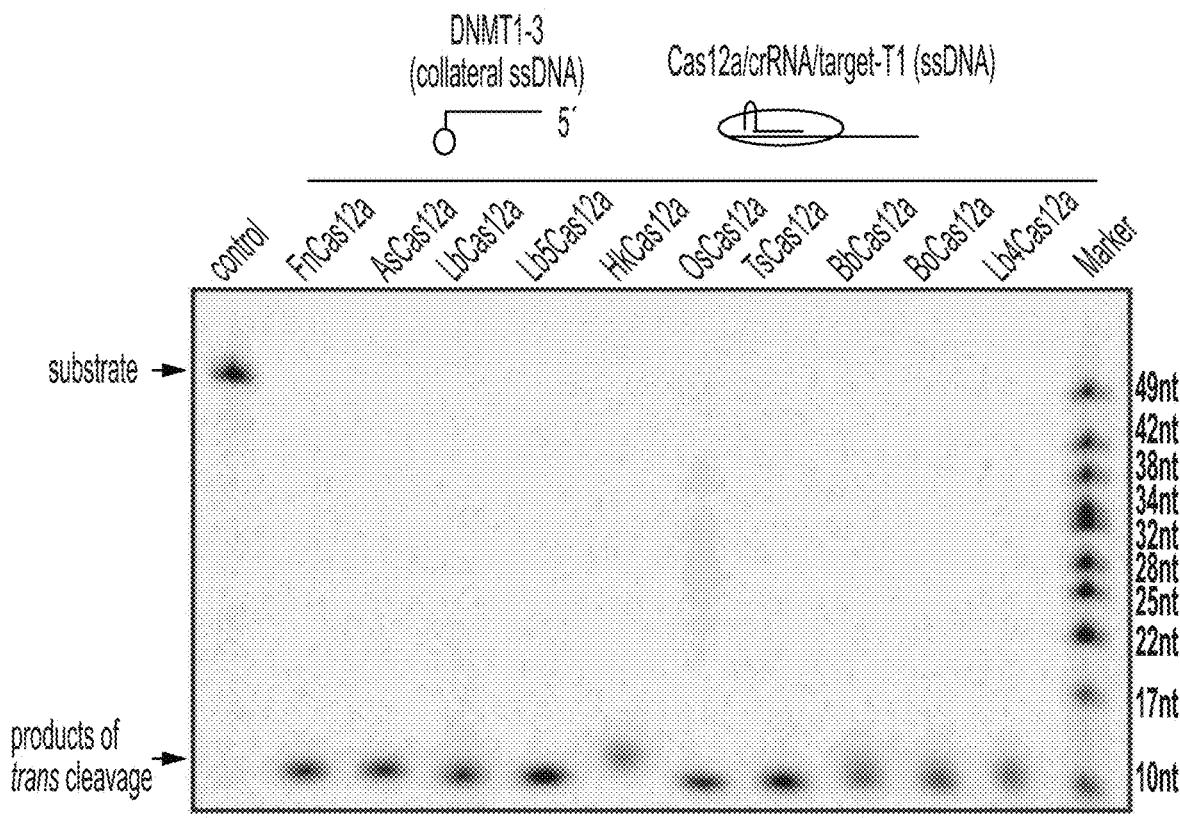

In addition to FnCas12a tested above, nine Cas12as from other species source were also tested (Table 2 and FIG. 4A). Except for Lb4Cas12a, all Cas12a have high endonuclease activity on plasmid DNA (as shown in FIG. 4B), and all Cas12a ternary complexes show both cis and trans cleavage activity on ssDNA (as shown in FIGS. 4C and 4D). This suggests that cis and trans activity of Cas12a against ssDNA is a common phenomenon.

Key Sites and Mechanisms of the Cis and Trans Cleavage of ssDNA by Cas12a

Figure 5A:
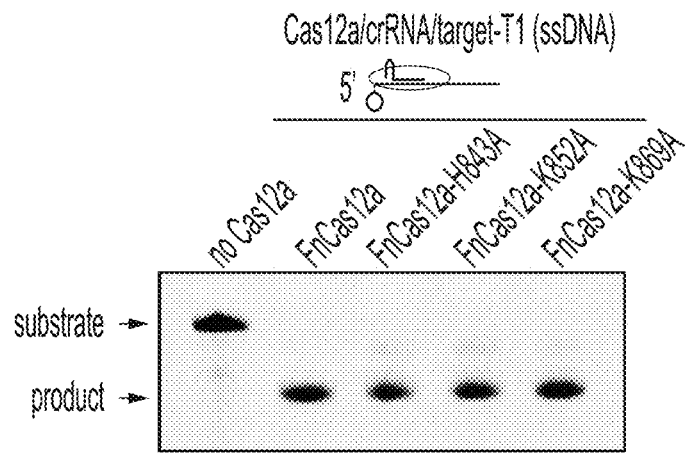
FIG. 5 shows through Cas12a single-point mutation experiment, the sites in Cas12a that may be related to the cis- and trans-cleavage activity of single-stranded DNA were identified.

To determine key amino acid residues in Cas12a for cis and trans activity on ssDNA, several candidate residues of Cas12a were mutated for the activity testing. First, three single amino acid mutants of FnCas12a (H843A, K852A and K869A) were purified and tested, the residues of which are related to the RNase activity. The results of the ssDNA trans-activity studies showed that wild-type FnCas12a and three mutants showed no significant difference in cis and trans cleavage activity against ssDNA, as shown in FIGS. 5A and 5C.

Figure 5B:
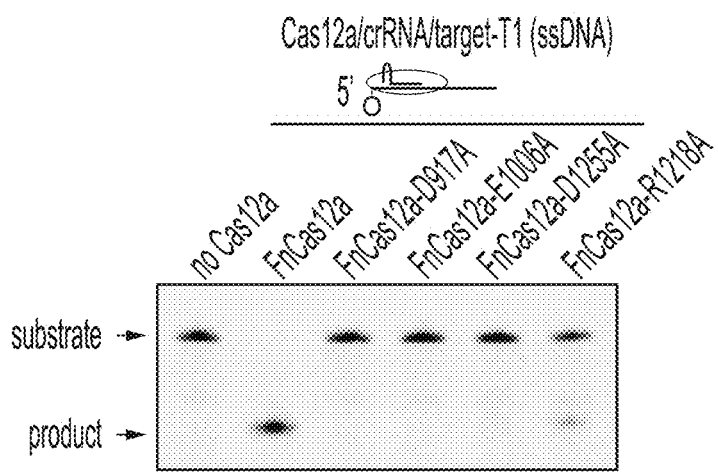
Figure 5C:
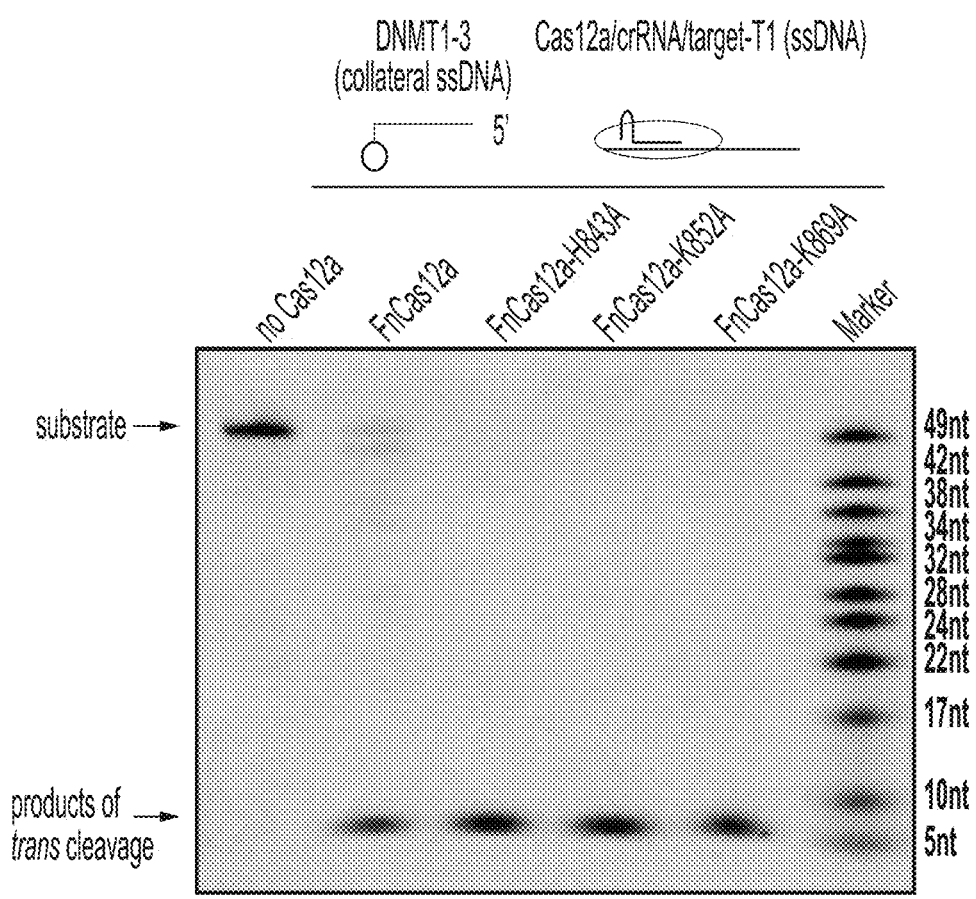
Figure 5D:
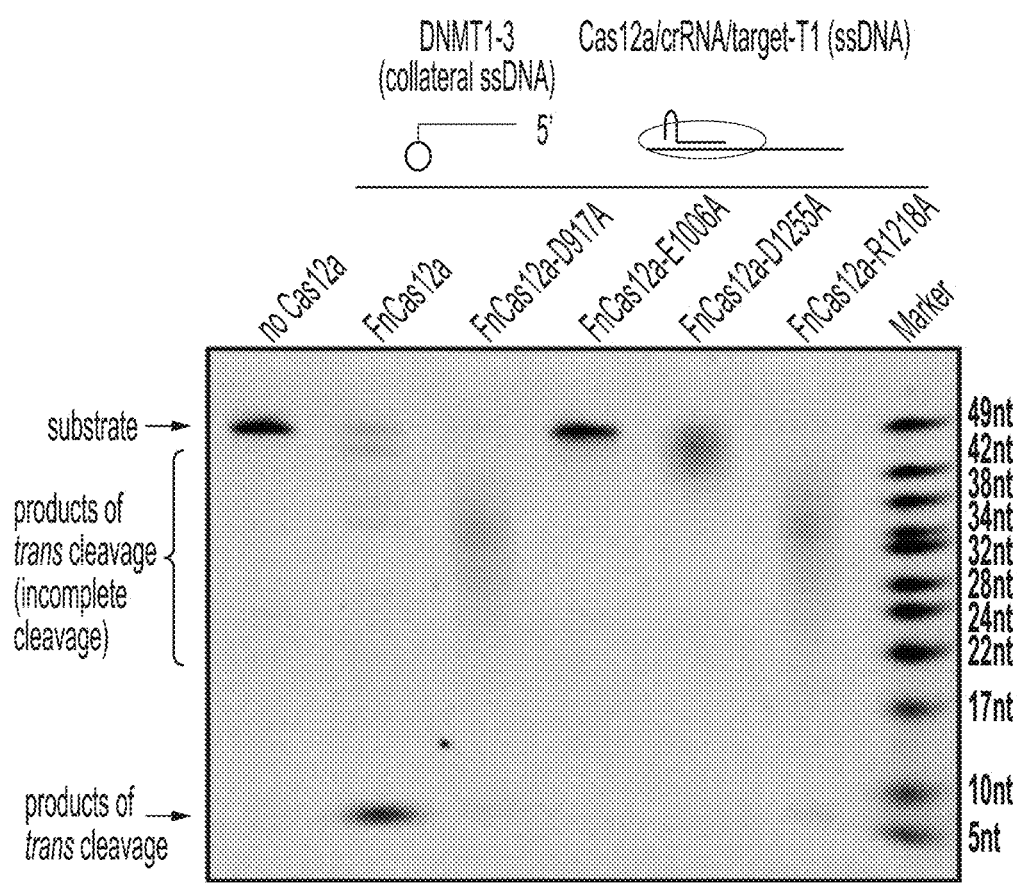

Next, when the endonuclease activity site in FnCas12a is mutated, i.e., the RuvC domain (D917A, E1006A or D1255A) and the Nuc domain (R1218A) site, the ssDNA cis and trans-cleavage activity of these mutant Cas12a were affected as shown in FIGS. 5B and 5D. These results indicate that the key sites of Cas12a responsible for target dsDNA cleavage are closely related to the cis and trans cleavage activities of ssDNA.

Figure 6:
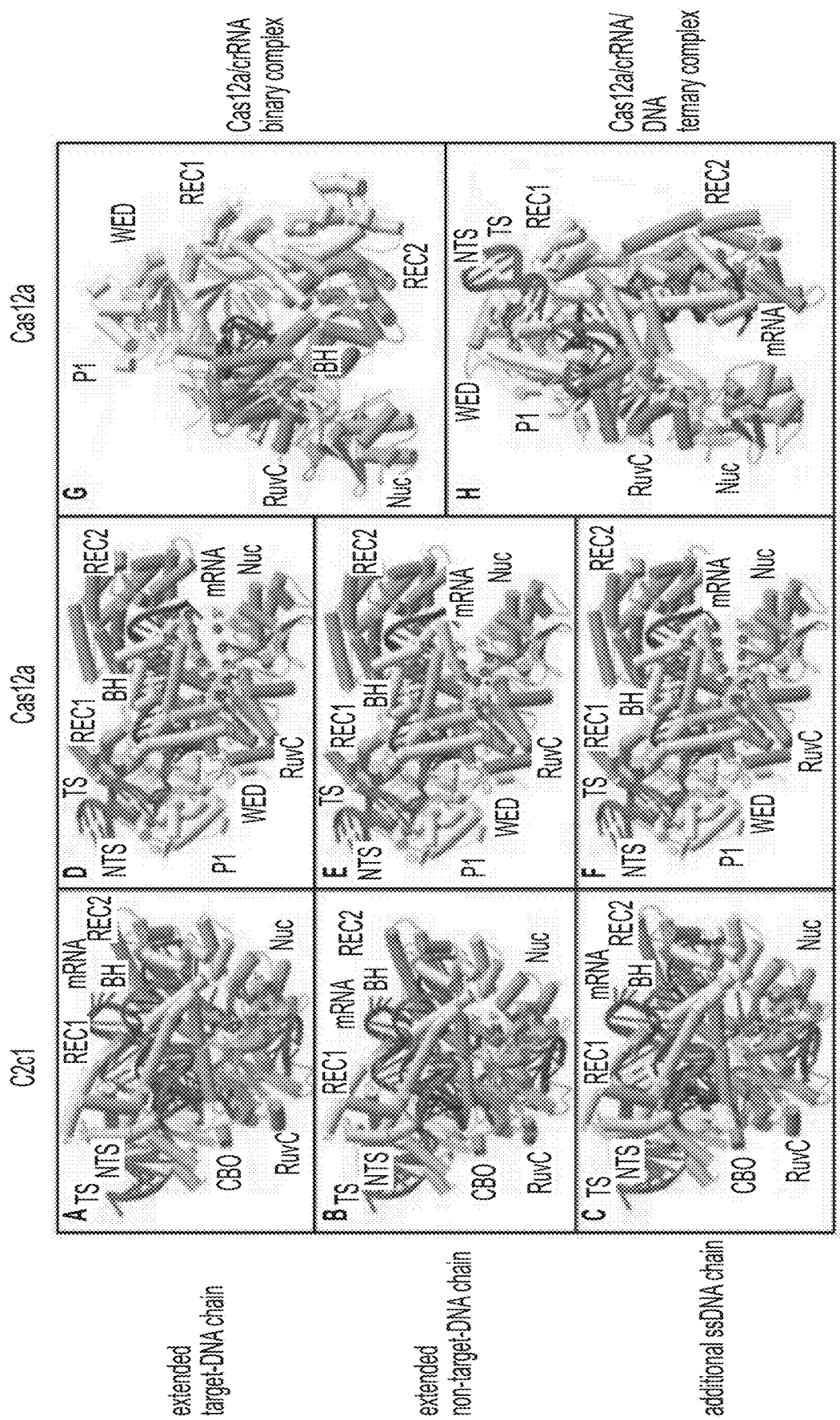
FIG. 6 shows the structures of Cas12a and Cas12b (i.e., C2c1) monomers and their complexes with guide RNA and target DNA.

A recent structural study of Cas12b (i.e. C2c1), including with extended target DNA or extended non-target DNA complexes, revealed that both strands were located within the RuvC pocket, as shown in FIGS. 6A and 6B. By comparing the endonuclease catalyzed residues of Cas12b (i.e. C2c1) and Cas12a, it is found that these sites most likely to play a similar role in the cleavage and function of Cas12b (i.e. C2c1) and Cas12a. The results of the in vitro single amino acid mutation experiment show that it is consistent with the above hypothesis, that is, Cas12a is likely to cleave both strands by only one RuvC catalytic pocket.

Trans cleavage activity of the Cas12a complex: In the structure of the Cas12b (i.e. C2c1) complex with additional ssDNA, sequence-independent ssDNA is also located on the surface of the catalytic pocket, as shown in FIG. 6C, which is similar to the collateral ssDNA substrate for Cas12a. Combining single amino acid mutation experiments, it is proposed that target DNA, non-target DNA and collateral ssDNA were all cleaved in a single RuvC pocket in Cas12a, as shown in FIGS. 6D, 6E and 6F. The reason why the ternary Cas12a complex has collateral ssDNA trans cleavage activity but the monomeric or binary complex does not have collateral ssDNA trans cleavage activity can be explained by comparing monomeric, binary, and ternary complex structures. The monomeric Cas12a structure is disordered. The binary complex Cas12a/crRNA is a triangular structure, as shown in FIG. 6G, while the ternary complex Cas12a/crRNA/target DNA is converted into a bilobal structure, thereby exposing the catalytic pocket to achieve trans cleavage of the collateral ssDNA (as shown in FIG. 6H).

Establishment of Nucleic Acid Probing Methods

Using the characteristics of Cas12a, a method for specifically detecting nucleic acid molecules has been developed, which is called HOLMES (one Hour Low-cost Multipurpose Efficient Simple assay). As the name of the technology, it is characterized as a one hour, low cost, multi-purpose, efficient, and simple test method.

In the whole reaction system, it can be divided into two large steps. One is the amplification of the template nucleic acid, and the other is the specific nucleic acid detection of the Cas12a protein. Here, PCR is used for amplification of nucleic acids, but in practice, any amplification method can be combined with nucleic acid detection of the second step, such as isothermal amplification method RPA or the like. The initial nucleic acid is not limited to double-stranded DNA, and may be single-stranded DNA; even RNA can be detected by reverse transcription, and thus the method is applicable to various types of nucleic acid molecules. For the nucleic acid detection stage, three components are the key to the experiment, namely Cas12a, crRNA and the nucleic acid probe. In addition to the 10 Cas12a mentioned in the examples (these 10 proteins are randomly selected), other Cas12a proteins are equally suitable for this method. In addition, other types of Cas proteins (such as C2c1 protein) are also suitable for the scope of the present invention. According to experimental results, *Alicyclobacillus acidoterrestris* Cas12b (i.e. C2c1) also has a collateral single-stranded DNA trans cleavage activity similar to Cas12a, its complex with crRNA/target DNA can also cleave collateral single-stranded DNA.

The crRNA as a guiding role is more stable in the system after being engineered by artificial modification or the like. In the selection of nucleic acid probes, HEX and BHQ1 labelled short single stranded DNA is selected in the present invention, and any other detectable labeling method is theoretically applicable as long as producing a detectable difference after the nucleic acid probe is cleaved. Alternatively, the nucleic acid probe can also be designed to be fluorescent after binding to the compound to probe whether the probe is cut off.

In addition, it should be understood that, after reading the above teachings of the present invention, those skilled in the art may make various modifications and changes to the present invention, these equivalent forms also fall within the scope defined by the claims appended hereto.

TABLE 1

| Cas12a property experiment related cleavage substrate sequence | | |
|---|---|---|
| Oligo name | Sequence (5'-3') | SEQ ID No.: |
| target-DNMT1-3-F | aatgtttcctgatggtccatgtctgttactcgcctgtcaagtggcgtgac | 1 |
| target-DNMT1-3-R | gtcacgccacttgacaggcgagtaacagacatggaccatcaggaaacatt | 2 |

TABLE 1-continued

Cas12a property experiment related cleavage substrate sequence

| Oligo name | Sequence (5'-3') | SEQ ID No.: |
|---|---|---|
| target-DNMT1-3-R-FAM-3' | gtcacgccacttgacaggcgagtaacagacatggaccatcagg aaacatt-FAM | 3 |
| target-DNMT1-3-R-FAM-5' | FAM-gtcacgccacttgacaggcgagtaacagacatggaccatcagg aaacatt | 4 |
| target-T1-F | tttctgtttgttatcgcaactttctactgaattcaagctttactctagaa agaggagaaaggatcc | 5 |
| target-T1-R | ggatcctttctcctctttctagagtaaagcttgaattcagtagaaagt tgcgataacaaacagaaa | 6 |
| target-T1-F-FAM | FAM-tttctgtttgttatcgcaactttctactgaattcaagctttactctagaa agaggagaaaggatcc | 7 |
| target-T1-R-FAM | ggatcctttctcctctttctagagtaaagcttgaattcagtagaaagt tgcgataacaaacagaaa-FAM | 8 |
| target-T1-FAM-3'-F | tttctgtttgttatcgcaactttctactgaattcaagctttactctagaa agaggagaaaggatcc-FAM | 9 |
| target-T1-FAM-5'-R | FAM-ggatcctttctcctctttctagagtaaagcttgaattcagtagaaagt tgcgataacaaacagaaa | 10 |
| target-DNMT1-3-R-TTT-FAM-3' | gtcacgccacttgacaggcgagtaacagacatggaccatcagg TTTcatt-FAM | 11 |
| target-DNMT1-3-R-CCC-FAM-3' | gtcacgccacttgacaggcgagtaacagacatggaccatcagg CCCcatt-FAM | 12 |
| target-DNMT1-3-R-GGG-FAM-3' | gtcacgccacttgacaggcgagtaacagacatggaccatcagg GGGcatt-FAM | 13 |
| target-DNMT1-3-F-AAA | aatgAAAcctgatggtccatgtctgttactcgcctgtcaagtgg cgtgac | 14 |
| target-DNMT1-3-F-GGG | aatgGGGcctgatggtccatgtctgttactcgcctgtcaagtgg cgtgac | 15 |
| target-DNMT1-3-F-CCC | aatgCCCcctgatggtccatgtctgttactcgcctgtcaagtgg cgtgac | 16 |
| target-T1-1-R | acaaacagaaa | 17 |
| target-T1-6-R | cgataacaaacagaaa | 18 |
| target-T1-12-R | aagttgcgataacaaacagaaa | 19 |
| target-T1-18-R | agtagaaagttgcgataacaaacagaaa | 20 |
| target-T1-24-R | gaattcagtagaaagttgcgataacaaacagaaa | 21 |
| target-T1-24-only-R | gaattcagtagaaagttgcgataa | 22 |
| target-T1-18-only-R | agtagaaagttgcgataa | 23 |
| target-T1-12-only-R | aagttgcgataa | 24 |
| target-T1-6-only-R | cgataa | 25 |
| N25-5FAM | FAM-NNNNNNNNNNNNNNNNNNNNNNNNN | 26 |
| N25-3FAM | NNNNNNNNNNNNNNNNNNNNNNNNN-FAM | 27 |

TABLE 2

Names and GI numbers of Cas12a protein and Cas12b (i.e. C2c1) protein

| Name | GI number | Species |
|---|---|---|
| FnCas12a | 489130501 | Francisella tularensis |
| AsCas12a | 545612232 | Acidaminococcus sp. BV3L6 |
| LbCas12a | 917059416 | Lachnospiraceae bacterium ND2006 |
| Lb5Cas12a | 652820612 | Lachnospiraceae bacterium NC2008 |
| HkCas12a | 491540987 | Helcococcus kunzii ATCC 51366 |
| OsCas12a | 909652572 | Oribacterium sp. NK2B42 |
| TsCas12a | 972924080 | Thiomicrospira sp. XS5 |
| BbCas12a | 987324269 | Bacteroidales bacterium KA00251 |
| BoCas12a | 496509559 | Bacteroidetes oral taxon 274 str. F0058 |
| Lb4Cas12a | 769130406 | Lachnospiraceae bacterium MC2017 |
| C2c1 | 1076761101 | Alicyclobacillus acidoterrestris |

TABLE 3

Plasmid information

| Plasmids or Strains | Relevant properties or genotypes | Sources |
|---|---|---|
| Plasmids | | |
| pET28a-TEV | pET28a with the thrombin cleavage site changed to the TEV protease cleavage site | (Carneiro, Silva et al. 2006) |
| pET28a-TEV-FnCas12a | pET28a-TEV carrying FnCas12a | (Li, Zhao et al. 2016) |
| pET28a-TEV-AsCas12a | pET28a-TEV carrying AsCas12a | (Li, Zhao et al. 2016) |
| pET28a-TEV-LbCas12a | pET28a-TEV carrying LbCas12a | (Lei, Li et al. 2017) |
| pET28a-TEV-Lb5Cas12a | pET28a-TEV carrying Lb5Cas12a | the present invention |
| pET28a-TEV-HkCas12a | pET28a-TEV carrying HkCas12a | the present invention |
| pET28a-TEV-OsCas12a | pET28a-TEV carrying OsCas12a | the present invention |
| pET28a-TEV-TsCas12a | pET28a-TEV carrying TsCas12a | the present invention |
| pET28a-TEV-BbCas12a | pET28a-TEV carrying BbCas12a | the present invention |
| pET28a-TEV-BoCas12a | pET28a-TEV carrying BoCas12a | the present invention |
| pET28a-TEV-Lb4Cas12a | pET28a-TEV carrying Lb4Cas12a | the present invention |
| pET28a-TEV-FnCas12a-K869A | pET28a-TEV carrying FnCas12a-K869A | the present invention |
| pET28a-TEV-FnCas12a-K852A | pET28a-TEV carrying FnCas12a-K852A | the present invention |
| pET28a-TEV-FnCas12a-H843A | pET28a-TEV carrying FnCas12a-H843A | the present invention |
| pET28a-TEV-FnCas12a-R1218A | pET28a-TEV carrying FnCas12a-R1218A | the present invention |
| pET28a-TEV-FnCas12a-E1006A | pET28a-TEV carrying FnCas12a-E1006A | the present invention |
| pET28a-TEV-FnCas12a-D917A | pET28a-TEV carrying FnCas12a-D917A | the present invention |
| pET28a-TEV-FnCas12a-D1255A | pET28a-TEV carrying FnCas12a-D1255A | the present invention |
| pET28a-TEV-C2c1 | pET28a-TEV carrying C2c1 | the present invention |

TABLE 4

Primers used in the HOLMES method test

| Oligo name | Sequence (5'-3') | SEQ ID No.: |
|---|---|---|
| target-T1-R | ggatcctttctcctctttctagagtaaagcttgaattcagtagaaagttgcgataacaaacagaaa | 28 |
| M13F-47 | cacaattccacacaacatacgagccgga | 29 |
| M13R-48 | tgtagccgtagttaggccaccacttca | 30 |
| Target-T1-F | agttttgttatcgcaactttctactgaattc | 31 |
| Target-T1-F-1A | agttttgAtatcgcaactttctactgaattc | 32 |
| Target-T1-F-2A | agttttgtAatcgcaactttctactgaattc | 33 |
| Target-T1-F-3T | agttttgttTtcgcaactttctactgaattc | 34 |
| Target-T1-F-4A | agttttgttaAcgcaactttctactgaattc | 35 |
| Target-T1-F-5G | agttttgttatGgcaactttctactgaattc | 36 |
| Target-T1-F-6C | agttttgttatcCcaactttctactgaattc | 37 |
| Target-T1-F-7G | agttttgttatcgGaactttctactgaattc | 38 |

TABLE 4-continued

Primers used in the HOLMES method test

| Oligo name | Sequence (5'-3') | SEQ ID No.: |
|---|---|---|
| Target-T1-F-8T | agttttgttatcgcTactttctactgaattc | 39 |
| Target-T1-F-9T | agttttgttatcgcaTctttctactgaattc | 40 |
| Target-T1-F-10G | agttttgttatcgcaaGtttctactgaattc | 41 |
| Target-T1-AAAN-F | aaaagttatcgcaactttctactgaattc | 42 |
| Target-T1-F-11A | agttttgttatcgcaacAttctactgaattcggtcatag | 43 |
| Target-T1-F-12A | agttttgttatcgcaactAtctactgaattcggtcatag | 44 |
| Target-T1-F-13A | agttttgttatcgcaacttActactgaattcggtcatag | 45 |
| Target-T1-F-14G | agttttgttatcgcaactttGtactgaattcggtcatag | 46 |
| Target-T1-F-15A | agttttgttatcgcaactttcAactgaattcggtcatag | 47 |
| Target-T1-F-16T | agttttgttatcgcaactttctTctgaattcggtcatag | 48 |
| Target-T1-F-17G | agttttgttatcgcaactttctaGtgaattcggtcatag | 49 |
| Target-T1-F-18A | agttttgttatcgcaactttctacAgaattcggtcatag | 50 |
| Target-T1-PAM1A-F | agtttAgttatcgcaactttctactgaattc | 51 |
| Target-T1-PAM2A-F | agttAtgttatcgcaactttctactgaattc | 52 |
| Target-T1-PAM3A-F | agtAttgttatcgcaactttctactgaattc | 53 |
| gyrB-F | AGTTGTCGTTCCTCAACTCCGGCGTTTC | 54 |
| gyrB-R | TCGACGCCAATACCGTCTTTTTCAGTGG | 55 |
| 1-5082-F | CTGCCTTTGCTTCTACCTTTGCCTGT | 56 |
| 1-5082-F-T | TTGCTTCTACCTTTGCCTGTTCTGG | 57 |
| 1-5082-R | TTTTCTGGCTGGGGATGGCCGATGG | 58 |
| 2-rs1467558-F | AGCAATAACACTAATATTGATTCCTTCAGATATGGACTCCTTTCATAGTA | 59 |
| 2-rs1467558-F-T | TTGATTCCTTCAGATATGGACTCCTTTCATAGTATAACG | 60 |
| 2-rs1467558-R | TGAGCATCGTTATTCTTACGCGTTGTCATTGAAAGAG | 61 |
| 3-rs2952768-F | AGCCTGGGCAACGAGTGAAACTCTG | 62 |
| 3-rs2952768-R | ACAGGAGGGACAAAGGCCTAAGTGTCC | 63 |
| 3-rs2952768-R-C | CATCATAGGATTGGGAAAAGGACATTTCAGTCATTCAG | 64 |
| 4-rs4363657-F | AGAGTCCTTCTTTCTCAATTTTTCAGAATAATTTAGTACTTTGGGTAC | 65 |
| 4-rs4363657-R | CAGTACTGAAAAAACCTGCCTATCAATAAAAGCCCTAGAC | 66 |
| 5-rs601338-F | GCTTCACCGGCTACCTTTGCTCCT | 67 |
| 5-rs601338-R | TTCACCTGCAGGCCCCGCAGG | 68 |
| 34-TP53-T24-F | CCTGACTTTCAACTCTGTCTCCTTCCTCTTTTTACAGTA | 69 |
| 34-TP53-T24-R | TGCTGTGACTGCTTGTAGATGGCCATGG | 70 |
| 41-rs10124290-F | AGTTTCCAGACCTCAGTGCACAAGATACTTTTCTAC | 71 |
| 41-rs1014290-F-G | ACCTCAGTGCACAAGATACTTTTCTACGTCATCCAC | 72 |

TABLE 4-continued

Primers used in the HOLMES method test

| Oligo name | Sequence (5'-3') | SEQ ID No.: |
|---|---|---|
| 41-rs1014290-R | AGCTCCAGTGGATGGAAGATCTTTGAGATCCAG | 73 |
| 42-rs6449213-F | AGTCAAAGAGATTCATGCCTGGGACTTTAATCACATTTAT | 74 |
| 42-rs6449213-F-C | ATGCCTGGGACTTTAATCACATTTATCGGAAGG | 75 |
| 42-rs6449213-R | CAAATCTGTCTCCACCTCTCAGCTCACCTTG | 76 |
| 43-rs737267-F | TTCTTGAACCCAAACTCACCTGGCATTTAAACTG | 77 |
| 43-rs737267-F-A | AAACTCACCTGGCATTTAAACTGACTCTGTAAG | 78 |
| 43-rs737267-F-T | AAACTCACCTGGCATTTAAACTGTCTCTGTAAG | 79 |
| 43-rs737267-R | TGCCGAGGCTGAGTTCAGCTACTCTCC | 80 |
| 44-rs1260326-F | ACACAGCACCGTGGGTCAGACCTTGC | 81 |
| 44-rs1260326-F-C | TGGGTCAGACTTTGCCGGTGAGAGTC | 82 |
| 44-rs1260326-F-T | TGGGTCAGACTTTGCTGGTGAGAGTC | 83 |
| 44-rs1260326-R | AGCAGTGGCCATGTGATGCTGATGATG | 84 |
| 45-rs642803-F | CCCCGGCTCTGTTGGCTTTGAGAATTG | 85 |
| 45-rs642803-F-C | CTCTGTTGGCTTTGAGAATTGCCTGTCTGTGTC | 86 |
| 45-rs642803-F-T | CTCTGTTGGCTTTGAGAATTGTCTGTCTGTGTC | 87 |
| 45-rs642803-R | ACCGATACCTGGCAGCCCTTGGATG | 88 |
| HEX-N12-BHQ1 | HEX-NNNNNNNNNNNN-BHQ1 | 89 |

TABLE 5

Template sequences for transcription of crRNA

| Oligo name | Sequence (5'-3') | SEQ ID No.: |
|---|---|---|
| T7-crRNA-F | GAAATTAATACGACTCACTATAGGG | 90 |
| T7-T1-24-R | gaattcagtagaaagttgcgataaATCTACAACAGTAGAAATTCCCTATAGTGAGTCGTATTAATTTC | 91 |
| T7-T1-15-R | agaaagttgcgataaATCTACAACAGTAGAAATTCCCTATAGTGAGTCGTATTAATTTC | 92 |
| T7-T1-16-R | tagaaagttgcgataaATCTACAACAGTAGAAATTCCCTATAGTGAGTCGTATTAATTTC | 93 |
| T7-T1-17-R | gtagaaagttgcgataaATCTACAACAGTAGAAATTCCCTATAGTGAGTCGTATTAATTTC | 94 |
| T7-T1-18-R | agtagaaagttgcgataaATCTACAACAGTAGAAATTCCCTATAGTGAGTCGTATTAATTTC | 95 |
| T7-crRNA-DNMT-23 nt-R | GAGTAACAGACATGGACCATCAGATCTACAACAGTAGAAATTCCCTATAGTGAGTCGTATTAATTTC | 96 |
| T7-crRNA-DNMT-(-8)-R | gacatggaccatcaggaaacattATCTACAACAGTAGAAATTCCCTATAGTGAGTCGTATTAATTTC | 97 |

TABLE 5-continued

Template sequences for transcription of crRNA

| Oligo name | Sequence (5'-3') | SEQ ID No.: |
| --- | --- | --- |
| T7-crRNA-DNMT-(+4)-R | aggcgagtaacagacatggaccaATCTACAACAGTAGAAATTCCCTATAGTGAGTCGTATTAATTTC | 98 |
| T7-crRNA-DNMT-(+8)-R | tgacaggcgagtaacagacatggATCTACAACAGTAGAAATTCCCTATAGTGAGTCGTATTAATTTC | 99 |
| T7-crRNA-DNMT-16 nt-R | agacatggaccatcagATCTACAACAGTAGAAATTCCCTATAGTGAGTCGTATTAATTTC | 100 |
| T7-crRNA-DNMT-18 nt-R | acagacatggaccatcagATCTACAACAGTAGAAATTCCCTATAGTGAGTCGTATTAATTTC | 101 |
| T7-crRNA-DNMT-20 nt-R | taacagacatggaccatcagATCTACAACAGTAGAAATTCCCTATAGTGAGTCGTATTAATTTC | 102 |
| T7-DNMT-(-8)-no loop-R | gacatggaccatcaggaaacattCCCTATAGTGAGTCGTATTAATTTC | 103 |
| T7-DNMT-(+4)-no loop-R | aggcgagtaacagacatggaccaCCCTATAGTGAGTCGTATTAATTTC | 104 |
| T7-DNMT-(+8)-no loop-R | tgacaggcgagtaacagacatggCCCTATAGTGAGTCGTATTAATTTC | 105 |
| T7-crRNA-rs5082-T | CCTCTTCCCAGAACAGGATCTACAACAGTAGAAATTCCCTATAGTGAGTCGTATTAATTTC | 106 |
| T7-crRNA-rs5082-G | CCTCTTCCCAGCACAGGATCTACAACAGTAGAAATTCCCTATAGTGAGTCGTATTAATTTC | 107 |
| T7-crRNA-rs1467558-T | CTGAAGCGTTATACTATATCTACAACAGTAGAAATTCCCTATAGTGAGTCGTATTAATTTC | 108 |
| T7-crRNA-rs1467558-C | CTGAAGCGTTGTACTATATCTACAACAGTAGAAATTCCCTATAGTGAGTCGTATTAATTTC | 109 |
| T7-crRNA-rs2952768-T-16 nt | TTTTATCTGAATGATTATCTACAACAGTAGAAATTCCCTATAGTGAGTCGTATTAATTTC | 110 |
| T7-crRNA-rs2952768-C-16 nt | TTTTATCTGAATGACTATCTACAACAGTAGAAATTCCCTATAGTGAGTCGTATTAATTTC | 111 |
| T7-crRNA-rs4363657-T | AAAAAAGAGTGAGTACCATCTACAACAGTAGAAATTCCCTATAGTGAGTCGTATTAATTTC | 112 |
| T7-crRNA-rs4363657-C | AAAAAAGAGTGGGTACCATCTACAACAGTAGAAATTCCCTATAGTGAGTCGTATTAATTTC | 113 |
| T7-crRNA-rs601338-G | GGTAGAAGGTCCAGGAGATCTACAACAGTAGAAATTCCCTATAGTGAGTCGTATTAATTTC | 114 |
| T7-crRNA-rs601338-A | GGTAGAAGGTCTAGGAGATCTACAACAGTAGAAATTCCCTATAGTGAGTCGTATTAATTTC | 115 |
| T7-crRNA-34-TP53-T24-C-16 nt | GGGCAGGGGAGTACTGATCTACAACAGTAGAAATTCCCTATAGTGAGTCGTATTAATTTC | 116 |
| T7-crRNA-34-TP53-T24-G-16 nt | GGGCAGGGGACTACTGATCTACAACAGTAGAAATTCCCTATAGTGAGTCGTATTAATTTC | 117 |
| T7-crRNA-41-rs1014290-A-15 nt | TCAGTGGATGATGTAATCTACAACAGTAGAAATTCCCTATAGTGAGTCGTATTAATTTC | 118 |
| T7-crRNA-41-rs1014290-G-15 nt | TCAGTGGATGACGTAATCTACAACAGTAGAAATTCCCTATAGTGAGTCGTATTAATTTC | 119 |
| T7-crRNA-42-rs6449213-C | GGAAATTCTCCTTCCGAATCTACAACAGTAGAAATTCCCTATAGTGAGTCGTATTAATTTC | 120 |

TABLE 5-continued

Template sequences for transcription of crRNA

| Oligo name | Sequence (5'-3') | SEQ ID No.: |
|---|---|---|
| T7-crRNA-42-rs6449213-T | GGAAATTCTCCTTCCAAATCTACAACAGTAGAAATTCCCTATAGTGAGTCGTATTAATTTC | 121 |
| T7-crRNA-43-rs737267-A-16 nt | TCTTACAGAGTCAGTTATCTACAACAGTAGAAATTCCCTATAGTGAGTCGTATTAATTTC | 122 |
| T7-crRNA-43-rs737267-G-16 nt | TCTTACAGAGCCAGTTATCTACAACAGTAGAAATTCCCTATAGTGAGTCGTATTAATTTC | 123 |
| T7-crRNA-43-rs737267-T | GTCTTACAGAGACAGTTATCTACAACAGTAGAAATTCCCTATAGTGAGTCGTATTAATTTC | 124 |
| T7-crRNA-44-rs1260326-C-15 nt | CTGGACTCTCACCGGATCTACAACAGTAGAAATTCCCTATAGTGAGTCGTATTAATTTC | 125 |
| T7-crRNA-44-rs1260326-T-15 nt | CTGGACTCTCACCGATCTACAACAGTAGAAATTCCCTATAGTGAGTCGTATTAATTTC | 126 |
| T7-crRNA-45-rs642803-C | CACAGACAGGCAATTCTATCTACAACAGTAGAAATTCCCTATAGTGAGTCGTATTAATTTC | 127 |
| T7-crRNA-45-rs642803-T | CACAGACAGACAATTCTATCTACAACAGTAGAAATTCCCTATAGTGAGTCGTATTAATTTC | 128 |
| T7-crRNA- gyrB | TCGCGCTTGTCGCGCAGACGAATGATCTACAACAGTAGAAATTCCCTATAGTGAGTCGTATTAATTTC | 129 |

Primers used in the detection of DNA LAMP amplification in combination with Cas12a:

TABLE 6

Primers for amplifying gyrB-1

| name | sequence | SEQ ID No.: |
|---|---|---|
| LAMP-gyrB-1-F3 | CATGGTGCGTTTCTGGCC | 130 |
| LAMP-gyrB-1-B3 | CGGCGTTTTGTTCTTGTTCA | 131 |
| LAMP-gyrB-1-FIP | ACAACTCACGCAGACGTTTCGCAACCTTCACCAATGTGACCG | 132 |
| LAMP-gyrB-1-BIP | GTTCCTCAACTCCGGCGTTTCCGATGCCGCCTTCATAGTGG | 133 |
| LAMP-gyrB-1-LoopF | CAGAATTTCATATTCGAACT | 134 |
| LAMP-gyrB-1-LoopB | GACGGCAAAGAAGACCACTT | 135 |

TABLE 7

Primers for amplifying gyrB-2

| name | sequence | SEQ ID No.: |
|---|---|---|
| LAMP-gyrB-2-F3 | CGACGGCAAAGAAGACCA | 136 |
| LAMP-gyrB-2-B3 | AGCCTGCCAGGTGAGTAC | 137 |
| LAMP-gyrB-2-FIP | CGGGTGGATCGGCGTTTTGTTCACTATGAAGGCGGCATCA | 138 |
| LAMP-gyrB-2-BIP | GTATTGGCGTCGAAGTGGCGTTCGCTGCGGAATGTTGTTG | 139 |
| LAMP-gyrB-2-LoopF | TTGTTCAGATATTCAACGAACG | 140 |
| LAMP-gyrB-2-LoopB | GTGGAACGATGGCTTCCAGG | 141 |

TABLE 8

Primers for amplifying the rs1467558 site

| name | sequence | SEQ ID No.: |
|---|---|---|
| LAMP-rs1467558-F3 | CAGCTGTAGACCATAAGCC | 142 |
| LAMP-rs1467558-B3 | GTGGCTGAGCATCGTTAT | 143 |
| LAMP-rs1467558-FIP | ACTATGAAAGGAGTCCATATCTGAAGGAATTCAGGTAGTGGTTTGGGA | 144 |
| LAMP-rs1467558-BIP | GCTTCAGCCTACTGCAAATCCTACGCGTTGTCATTGAAAG | 145 |
| LAMP-rs1467558-LoopF | TCAATATTAGTGTTATTGCTTG | 146 |
| LAMP-rs1467558-LoopB | TGGTGGAAGATTTGGACAGGAC | 147 |

TABLE 9

Primers for amplifying the rs5082 site

| name | sequence | SEQ ID No.: |
|---|---|---|
| LAMP-rs5082-F3 | GCTGGAAAGGTCAAGGGAC | 148 |
| LAMP-rs5082-B3 | GGGGTTTGTTGCACAGTCC | 149 |
| LAMP-rs5082-FIP | CAAAGGTAGAAGCAAAGGCAGGAG GTTTGCCCAAGGTCACACAG | 150 |
| LAMP-rs5082-BIP | CTGGGAAGAGGGAGGGCTCAGTGT TGCCACACTTTCACTGG | 151 |
| LAMP-rs5082-LoopF | GTGAGCGGGTGGGGTGCT | 152 |
| LAMP-rs5082-LoopB | TCTAAGTCTTCCAGCACGGGATC | 153 |

TABLE 10

Primers used in the detection of RPA amplification in combination with Cas12

| name | sequence | SEQ ID No.: |
|---|---|---|
| RPA-gyrB-1-F | ATATGAAATTCTGGCGAAACGTCTGCGTGA GTTG | 154 |
| RPA-gyrB-2-F | AAACGTCTGCGTGAGTTGTCGTTCCTCAAC TCC | 155 |
| RPA-gyrB-R | ACTTCGACGCCAATACCGTCTTTTTCAGTG GAG | 156 |

TABLE 1

Primers used in determination Cas12b for trans cleavage activity:

| Oligo name | Sequence (5'-3') | SEQ ID No.: |
|---|---|---|
| pUC18-1-F | ATCTGAGAAGTGGCACTTATCGCAACTTTCTA CTGAGGTCATAGCTGTTTCCTGTGTGA | 157 |
| pUC18-1-R | GTCCTCTAGACCCCTATAGTGAGTCGTATTAA TTTCATGATTACGAATTCGAGCTCGGT | 158 |
| pUC18-2-F | CCACTTTCCAGGTGGCAAAGCCCGTTGAGCTT CTCAAATCTGAGAAGTGGCACTTATC | 159 |
| pUC18-2-R | TGGAAAGTGGCCATTGGCACACCCGTTGAAA AATTCTGTCCTCTAGACCCCTATAGTGA | 160 |
| T7-crRNA-F | GAAATTAATACGACTCACTATAGGG | 161 |
| ZL-sgRNA-T1-R | TCAGTAGAAAGTTGCGATAAGTGC | 162 |
| ZLsgRNA-DNMT1-3-R | AACAGACATGGACCATCAGGGTG | 163 |
| target-T1-F | TTTCTGTTTGTTATCGCAACTTTCTACTGAATT CAAGCTTTACTCTAGAAAGAGGAGAAAGGAT CC | 164 |
| target-T1-R | GGATCCTTTCTCCTCTTTCTAGAGTAAAGCTT GAATTCAGTAGAAAGTTGCGATAACAAACAG AAA | 165 |
| target-DNMT1-3-R-FAM-5' | GTCACGCCACTTGACAGGCGAGTAACAGACA TGGACCATCAGGAAACATT | 166 |
| target-T1-R | GGATCCTTTCTCCTCTTTCTAGAGTAAAGCTT GAATTCAGTAGAAAGTTGCGATAACAAACAG AAA | 167 |
| target-T1-F | TTTCTGTTTGTTATCGCAACTTTCTACTGAATT CAAGCTTTACTCTAGAAAGAGGAGAAAGGAT CC | 168 |

TABLE 12

Primers used in the sensitivity test of the trans reaction of Cas12b:

| Oligo name | Sequence (5'-3') | SEQ ID No.: |
|---|---|---|
| sgRNA-DNMT1-3-F | CCTGATGGTCCATGTCTGTTGGTCATAG CTGTTTCCTGTGTG | 169 |
| sgRNA-DNMT1-3-R | TGGACCATCAGGGTGCCACTTCTCAGAT TGAGAAG | 170 |
| T7-crRNA-F | GAAATTAATACGACTCACTATAGGG | 171 |
| ZLsgRNA-DNMT1-3-R | AACAGACATGGACCATCAGGGTG | 172 |
| DNMT1-3(TTC PAM)-F | AATGTTCCCTGATGGTCCATGTCTGTTA CTCGCCTGTCAAGTGGCGTGAC | 173 |
| DNMT1-3(TTC PAM)-R | GTCACGCCACTTGACAGGCGAGTAACA GACATGGACCATCAGGGAACATT | 174 |
| LAMP-DNM-F3 | gtgaacgttcccttagcact | 175 |
| LAMP-DNM-B3 | gggagggcagaactagtcc | 176 |
| LAMP-DNM-FIP | cgccacttgacaggcgagtaactgccacttattgggtcagc | 177 |
| LAMP-DNM-BIP | gcgtgttccccagagtgacttagcagcttcctcctcctt | 178 |

TABLE 12-continued

Primers used in the sensitivity test of the trans reaction of Cas12b:

| Oligo name | Sequence (5'-3') | SEQ ID No.: |
|---|---|---|
| LAMP-DNM-LoopF | aggaaacattaacgtactgatg | 179 |
| LAMP-DNM-LoopB | ttccttttatttcccttcagc | 180 |
| DNMT1-3(TTC PAM)-R | GTCACGCCACTTGACAGGCGAGTAACA GACATGGACCATCAGGGAACATT | 181 |
| DNMT1-3(TTC PAM)-F | AATGTTCCCTGATGGTCCATGTCTGTTA CTCGCCTGTCAAGTGGCGTGAC | 182 |

TABLE 13

Other sequences involved in the present invention

| Name | Sequence | SEQ ID No.: |
|---|---|---|
| AacCas12b sgRNA sequence | GTCTAGAGGACAGAATTTTTCAACGGGTGTG CCAATGGCCACTTTCCAGGTGGCAAAGCCCG TTGAGCTTCTCAAATCTGAGAAGTGGCACcctg atggtccatgtctgtt | 183 |
| Guide sequence targetingtarget DNMT-1-3 | cctgatggtccatgtctgtt | 184 |
| Single-stranded target sequence | gtcacgccacttgacaggcgagtaacagacatggaccatcagggaacatt | 185 |
| Double-stranded target sequence: | gtcacgccacttgacaggcgagtaacagacatggaccatcagggaacatt | 186 |
| amino acid sequence of AacCas12b protein | MAVKSIKVKLRLDDMPEIRAGLWKLHKEVNA GVRYYTEWLSLLRQENLYRRSPNGDGEQECDK TAEECKAELLERLRARQVENGHRGPAGSDDEL LQLARQLYELLVPQAIGAKGDAQQIARKFLSPL ADKDAVGGLGIAKAGNKPRWVRMREAGEPG WEEEKEKAETRKSADRTADVLRALADFGLKPL MRVYTDSEMSSVEWKPLRKGQAVRTWDRDMF QQAIERMMSWESWNQRVGQEYAKLVEQKNRF EQKNFVGQEHLVHLVNQLQQDMKEASPGLESK EQTAHYVTGRALRGSDKVFEKWGKLAPDAPFD LYDAEIKNVQRRNTRRFGSHDLFAKLAEPEYQ ALWREDASFLTRYAVYNSILRKLNHAKMFATF TLPDATAHPIWTRFDKLGGNLHQYTFLFNEFGE RRHAIRFHKLLKVENGVAREVDDVTVPISMSEQ LDNLLPRDPNEPIALYFRDYGAEQHFTGEFGGA KIQCRRDQLAHMHRRRGARDVYLNVSVRVQS QSEARGERRPPYAAVFRLVGDNHRAFVHFDKL SDYLAEHPDDGKLGSEGLLSGLRVMSVDLGLR TSASISVFRVARKDELKPNSKGRVPFFFPIKGND NLVAVHERSQLLKLPGETESKDLRAIREERQRT LRQLRTQLAYLRLLVRCGSEDVGRRERSWAKL IEQPVDAANHMTPDWREAFENELQKLKSLHGI CSDKEWMDAVYESVRRVWRHMGKQVRDWR KDVRSGERPKIRGYAKDVVGGNSIEQIEYLERQ YKFLKSWSFFGKVSGQVIRAEKGSRFAITLREHI DHAKEDRLKKLADRIIMEALGYVYALDERGKG KWVAKYPPCQLILLEELSEYQFNNDRPPSENNQ LMQWSHRGVFQELINQAQVHDLLVGTMYAAF SSRFDARTGAPGIRCRRVPARCTQEHNPEPFPW WLNKFVVEHTLDACPLRADDLIPTGEGEIFVSPF SAEEGDFHQIHADLNAAQNLQQRLWSDFDISQI RLRCDWGEVDGELVLIPRLTGKRTADSYSNKV FYTNTGVTYYERERGKKRRKVFAQEKLSEEEA ELLVEADEAREKSVVLMRDPSGIINRGNWTRQ KEFWSMVNQRIEGYLVKQIRSRVPLQDSACENT GDI* | 187 |

All publications mentioned in the present invention are incorporated by reference as if each individual publication was cited as a reference in the present application. It should be understood that, after reading the above teachings of the present invention, those skilled in the art can make various modifications and changes to the present invention. These equivalent forms are also within the scope defined by the claims appended hereto.

What is claimed is:

1. A method for detecting target nucleic acid molecules comprising a target sequence, the method comprising steps of:

1) Adding (a) a guide RNA comprising a target site that specifically hybridizes with the target sequence;

(b) a Cas12 protein having collateral cleavage activity, wherein the collateral cleavage activity of the Cas 12 protein is activated when specific hybridization of the guide RNA and the target sequence occurs;

(c) a detectably labeled nucleic acid probe susceptible to the collateral cleavage activity of the Cas12 protein; and (d) a buffer into a system containing the target nucleic acid molecules to be detected, and 2) then detecting cleavage of the nucleic acid probe.

2. The method of claim 1, wherein the target nucleic acid molecules to be detected have been amplified.

3. The method of claim 2, wherein the target nucleic acid molecules have been amplified by an amplification method selected from the group consisting of: PCR amplification, LAMP amplification, RPA amplification, ligase chain reaction, branched DNA amplification, NASBA, SDA, transcription-mediated amplification, rolling circle amplification, HDA, SPIA, NEAR, TMA and SMAP2.

4. The method of claim 2, wherein the target nucleic acid molecules are amplified using primers comprising a protospacer adjacent motif (PAM) sequence.

5. The method of claim 4, wherein the amplification product comprises a PAM sequence upstream or downstream of the target site of the guide RNA.

6. The method of claim 5, wherein the PAM site is -20nt to +20nt upstream or downstream of the target site of the guide RNA.

7. The method of claim 1, wherein detecting cleavage of the nucleic acid probe comprises a fluorescence detection method.

8. The method of claim 7, wherein the fluorescence detection method comprises a detection method using a microplate reader or a fluorescence spectrophotometer.

9. The method of claim 1, wherein the detectably labeled nucleic acid probe comprises a fluorescent group at the 5' end and a quenching group at the 3' end.

10. The method of claim 9, wherein the fluorescent group is HEX and the quenching group is BHQ1.

11. The method of claim 1, wherein the Cas12 protein is selected from the group consisting of: FnCas12a, AsCas12a, LbCas12a, Lb5Cas12a, HkCas12a, OsCas12a, TsCas12a, BbCas12a, BoCas12a, Lb4Cas12a; LbCas12a and C2c1.

12. The method of claim 1, wherein the target nucleic acid molecules comprise a sequence found in a pathogen.

13. The method of claim 1, wherein the target nucleic acid molecules comprise a sequence found in a human cancer.

14. A detection system comprising:
(a) target nucleic acid molecules comprising a target sequence of interest;
(b) a Cas12 protein having collateral cleavage activity;
(c) a guide RNA comprising a target site that specifically hybridizes with the target sequence of interest, wherein the collateral cleavage activity is activated when the specific hybridization occurs;
(d) a detectably labeled nucleic acid probe susceptible to the collateral cleavage activity of the Cas12 protein; and
(e) buffer.

15. The detection system of claim 14, wherein the Cas12 protein is selected from the group consisting of: FnCas12a, AsCas12a, LbCas12a, Lb5Cas12a, HkCas12a, OsCas12a, TsCas12a, BbCas12a, BoCas12a, Lb4Cas12a and C2c1.

16. The detection system of claim 14, wherein the target nucleic acid molecules to be detected have been amplified by an amplification method.

17. The detection system of claim 16, wherein the target nucleic acid molecules have been amplified by an amplification method selected from the group consisting of: PCR amplification, LAMP amplification, RPA amplification, ligase chain reaction, branched DNA amplification, NASBA, SDA, transcription-mediated amplification, rolling circle amplification, HDA, SPIA, NEAR, TMA and SMAP2.

18. The detection system of claim 16, wherein the target nucleic acid molecules are amplified using primers comprising a protospacer adjacent motif (PAM) sequence.

19. The detection system of claim 18, wherein the amplification product comprises a PAM sequence upstream or downstream of a target site of the guide RNA.

20. The detection system of claim 19, wherein the PAM site is −20nt to +20nt upstream or downstream of the target site of the guide RNA.

21. The detection system of claim 14, wherein the target nucleic acid molecules comprise a sequence found in a pathogen.

22. The detection system of claim 14, wherein the target nucleic acid molecules comprise a sequence found in a human cancer.

23. The detection system of claim 14, wherein the detectably labeled nucleic acid probe comprises a fluorescent group at the 5' end and a quenching group at the 3' end.

24. The detection system of claim 23, wherein the fluorescent is HEX and the quenching group is BHQ1.

25. A kit for detecting target nucleic acid molecules comprising a target sequence, characterized in that the kit comprises:
i) a first container and a Cas12 protein located in the first container, wherein the Cas12 protein has collateral cleavage activity;
ii) a second container and a guide RNA located in the second container, wherein the guide RNA that specifically hybridizes with the target sequence, wherein the collateral cleavage activity is activated when the specific hybridization occurs;
iii) a third container and a detectably labeled nucleic acid probe located in the third container, wherein the detectably labeled nucleic acid probe is susceptible to the collateral cleavage activity of the Cas12 protein; and
iv) a fourth container and a buffer located in the fourth container.

* * * * *